US009668728B2

(12) United States Patent
Williams et al.

(10) Patent No.: US 9,668,728 B2
(45) Date of Patent: Jun. 6, 2017

(54) SURGICAL STAPLING APPARATUS

(71) Applicant: Covidien LP, Mansfield, MA (US)

(72) Inventors: Justin Williams, Naugatuck, CT (US); Christopher Penna, Guilford, CT (US); Lee Ann Olson, Wallingford, CT (US); Stanislaw Marczyk, Stratford, CT (US); Kenneth M. Cappola, Monroe, CT (US); Thomas R. Hessler, Bethel, CT (US); Ernest Aranyi, Easton, CT (US); Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 766 days.

(21) Appl. No.: 13/923,651

(22) Filed: Jun. 21, 2013

(65) Prior Publication Data

US 2014/0263566 A1    Sep. 18, 2014

Related U.S. Application Data

(60) Provisional application No. 61/779,873, filed on Mar. 13, 2013.

(51) Int. Cl.
*A61B 17/068* (2006.01)
*A61B 17/10* (2006.01)
(Continued)

(52) U.S. Cl.
CPC .......... *A61B 17/068* (2013.01); *A61B 17/105* (2013.01); *A61B 17/07207* (2013.01);
(Continued)

(58) Field of Classification Search
CPC ............ A61B 17/068; A61B 17/07207; A61B 2017/07271; A61B 2017/07278; A61B 2017/2946; A61B 2017/00367
(Continued)

(56) References Cited

U.S. PATENT DOCUMENTS 3,079,606 A    3/1963    Bobrov et al.
3,490,675 A    1/1970    Green et al.
(Continued)

FOREIGN PATENT DOCUMENTS

AU    198654765    9/1986
DE    2744824    4/1978
(Continued)

OTHER PUBLICATIONS

European Office Action dated Feb. 24, 2016, issued in European Application No. 14 159 118.0.
(Continued)

*Primary Examiner* — Hemant M Desai
*Assistant Examiner* — Valentin Neacsu

(57) ABSTRACT

A surgical stapling apparatus (stapler) is provided. The stapler includes a housing, elongated member, and a reload. A cartridge is configured to selectively couple to a first jaw member of the reload and includes one or more resilient members thereon. An anvil operably supported on a second jaw member of the reload is configured to compress one or more fasteners ejected from the cartridge. The anvil includes one or more locking members thereon. A knife is configured to translate through the cartridge and anvil when the first and second jaw members are in a closed configuration. Engagement between the knife and the resilient member(s) causes the resilient member(s) to move from an initial configuration that allows the knife to travel distally past the locking member(s) to a final configuration that allows the locking member(s) to engage the knife.

15 Claims, 83 Drawing Sheets

(51) Int. Cl.
- *A61B 17/072* (2006.01)
- *A61B 17/00* (2006.01)
- *A61B 17/29* (2006.01)
- *A61B 90/00* (2016.01)

(52) U.S. Cl.
CPC ............ *A61B 2017/00473* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2090/0814* (2016.02)

(58) Field of Classification Search
USPC ......... 227/175.1, 175.2, 175.4, 176.1, 180.1; 606/219
See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A * | 1/1990 | Fox ..................... A61B 17/068 227/120 |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | deSalis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A * | 7/1992 | Schulze ........... A61B 17/07207 227/175.2 |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughetti et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |

(56) References Cited

U.S. PATENT DOCUMENTS

| | | |
|---|---|---|
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,779 A * | 6/1997 | Palmer ................ A61B 17/072 227/175.2 |
| 5,636,780 A | 6/1997 | Green et al. |
| 5,645,209 A | 7/1997 | Green et al. |
| 5,647,526 A | 7/1997 | Green et al. |
| 5,651,491 A * | 7/1997 | Heaton ............ A61B 17/07207 227/175.1 |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A * | 10/1997 | Bittner ............ A61B 17/07207 227/175.2 |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A * | 3/1999 | Bittner ............ A61B 17/07207 227/175.4 |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |

(56) References Cited

U.S. PATENT DOCUMENTS

| | | |
|---|---|---|
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Gerbi et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Ratcliff et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,945,444 B2 | 9/2005 | Gresham |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |

(56) References Cited

U.S. PATENT DOCUMENTS

| | | |
|---|---|---|
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Gillum et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,930 B2 | 5/2010 | McKenna et al. |
| 7,721,931 B2 | 5/2010 | Shelton et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton et al. |
| 7,740,160 B2 | 6/2010 | Viola |
| 7,743,960 B2 | 6/2010 | Whitman |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |

(56) References Cited

U.S. PATENT DOCUMENTS

| | | |
|---|---|---|
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica et al. |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |

(56) References Cited

U.S. PATENT DOCUMENTS

| | | |
|---|---|---|
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,901 B2 | 8/2012 | Stopek |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV et al. |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,469,252 B2 | 6/2013 | Holcomb et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,496,152 B2 | 7/2013 | Viola |
| 8,496,156 B2 | 7/2013 | Sniffin |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,517,241 B2 | 8/2013 | Nicholas et al. |
| 8,517,244 B2 | 8/2013 | Shelton, IV et al. |
| 8,523,043 B2 | 9/2013 | Ullrich et al. |
| 2004/0108357 A1 | 6/2004 | Milliman |
| 2004/0199180 A1 | 10/2004 | Knodel et al. |
| 2004/0199181 A1 | 10/2004 | Knodel et al. |
| 2004/0232200 A1* | 11/2004 | Shelton ............ A61B 17/07207 227/176.1 |
| 2004/0232201 A1 | 11/2004 | Wenchell |
| 2004/0243151 A1 | 12/2004 | Demmy |
| 2004/0267310 A1 | 12/2004 | Racenet |

(56) References Cited

U.S. PATENT DOCUMENTS

| | | |
|---|---|---|
| 2005/0103819 A1 | 5/2005 | Racenet |
| 2005/0119669 A1 | 6/2005 | Demmy |
| 2005/0189397 A1 | 9/2005 | Jankowski |
| 2005/0216055 A1 | 9/2005 | Scirica et al. |
| 2006/0049229 A1 | 3/2006 | Milliman et al. |
| 2006/0180634 A1 | 8/2006 | Shelton, IV et al. |
| 2006/0289602 A1 | 12/2006 | Wales et al. |
| 2007/0027469 A1 | 2/2007 | Smith et al. |
| 2007/0073341 A1 | 3/2007 | Smith et al. |
| 2007/0084896 A1* | 4/2007 | Doll ................ A61B 17/07207 227/175.2 |
| 2007/0084897 A1 | 4/2007 | Shelton et al. |
| 2007/0084899 A1 | 4/2007 | Taylor |
| 2007/0102472 A1 | 5/2007 | Shelton, IV |
| 2007/0106317 A1 | 5/2007 | Shelton, IV |
| 2007/0119901 A1 | 5/2007 | Ehrenfels et al. |
| 2007/0145096 A1 | 6/2007 | Viola et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078808 A1 | 4/2008 | Hess et al. |
| 2008/0110961 A1 | 5/2008 | Voegele et al. |
| 2008/0149685 A1 | 6/2008 | Smith et al. |
| 2008/0167670 A1* | 7/2008 | Shelton ............ A61B 17/07207 606/167 |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0290135 A1* | 11/2008 | Mastri ............ A61B 17/07207 227/179.1 |
| 2008/0296344 A1 | 12/2008 | Cropper et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005808 A1 | 1/2009 | Hess et al. |
| 2009/0065549 A1 | 3/2009 | Viola |
| 2009/0078739 A1 | 3/2009 | Viola |
| 2009/0090763 A1 | 4/2009 | Zemlok et al. |
| 2009/0090766 A1 | 4/2009 | Knodel |
| 2009/0206131 A1* | 8/2009 | Weisenburgh, II ........ A61B 17/07207 227/175.2 |
| 2009/0206132 A1* | 8/2009 | Hueil ............ A61B 17/07207 227/175.2 |
| 2009/0206134 A1* | 8/2009 | Swayze ............ A61B 17/07207 227/176.1 |
| 2009/0206138 A1* | 8/2009 | Smith ............ A61B 17/07207 227/176.1 |
| 2009/0209946 A1 | 8/2009 | Swayze et al. |
| 2009/0209990 A1 | 8/2009 | Yates et al. |
| 2009/0236395 A1 | 9/2009 | Scirica |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277946 A1 | 11/2009 | Marczyk |
| 2009/0277949 A1 | 11/2009 | Viola et al. |
| 2009/0283568 A1 | 11/2009 | Racenet et al. |
| 2009/0302090 A1* | 12/2009 | Shah ................ A61B 17/07207 227/180.1 |
| 2009/0306708 A1* | 12/2009 | Shah ................ A61B 17/07207 606/219 |
| 2009/0308907 A1 | 12/2009 | Nalagatla et al. |
| 2010/0012703 A1 | 1/2010 | Calabrese et al. |
| 2010/0012704 A1 | 1/2010 | Racenet et al. |
| 2010/0069942 A1 | 3/2010 | Shelton, IV et al. |
| 2010/0072254 A1 | 3/2010 | Aranyi et al. |
| 2010/0076429 A1 | 3/2010 | Heinrich |
| 2010/0076459 A1 | 3/2010 | Farascioni |
| 2010/0089970 A1 | 4/2010 | Smith |
| 2010/0127041 A1 | 5/2010 | Morgan et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0147921 A1 | 6/2010 | Olson |
| 2010/0147922 A1 | 6/2010 | Olson |
| 2010/0155453 A1 | 6/2010 | Bombard et al. |
| 2010/0170931 A1 | 7/2010 | Viola |
| 2010/0193566 A1 | 8/2010 | Scheib et al. |
| 2010/0213241 A1* | 8/2010 | Bedi ................ A61B 17/07207 227/180.1 |
| 2010/0224668 A1 | 9/2010 | Fontayne et al. |
| 2010/0230468 A1 | 9/2010 | Viola |
| 2010/0237130 A1 | 9/2010 | Scirica |
| 2010/0243708 A1* | 9/2010 | Aranyi ............ A61B 17/07207 227/176.1 |
| 2010/0243709 A1 | 9/2010 | Hess et al. |
| 2010/0249802 A1 | 9/2010 | May et al. |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0294828 A1 | 11/2010 | Bindra et al. |
| 2010/0294829 A1* | 11/2010 | Giordano ............ A61B 19/026 227/176.1 |
| 2010/0301095 A1 | 12/2010 | Shelton, IV et al. |
| 2010/0305552 A1 | 12/2010 | Shelton, IV et al. |
| 2010/0308100 A1 | 12/2010 | Boudreaux |
| 2010/0320252 A1 | 12/2010 | Viola et al. |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036887 A1 | 2/2011 | Zemlok et al. |
| 2011/0036888 A1 | 2/2011 | Pribanic et al. |
| 2011/0036890 A1 | 2/2011 | Ma |
| 2011/0036891 A1 | 2/2011 | Zemlok et al. |
| 2011/0036892 A1 | 2/2011 | Marczyk et al. |
| 2011/0036895 A1 | 2/2011 | Marczyk et al. |
| 2011/0042439 A1 | 2/2011 | Johnson et al. |
| 2011/0042441 A1 | 2/2011 | Shelton, IV et al. |
| 2011/0062213 A1 | 3/2011 | Scirica et al. |
| 2011/0068145 A1 | 3/2011 | Bedi et al. |
| 2011/0068148 A1 | 3/2011 | Hall et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089221 A1 | 4/2011 | Masiakos et al. |
| 2011/0095067 A1 | 4/2011 | Ohdaira |
| 2011/0101067 A1 | 5/2011 | Johnson et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |

(56) References Cited

U.S. PATENT DOCUMENTS

| | | |
|---|---|---|
| 2011/0132961 A1 | 6/2011 | Whitman et al. |
| 2011/0132963 A1 | 6/2011 | Giordano et al. |
| 2011/0132964 A1* | 6/2011 | Weisenburgh, II ............... A61B 17/07207 227/176.1 |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163149 A1 | 7/2011 | Viola |
| 2011/0163150 A1 | 7/2011 | Farascioni |
| 2011/0168757 A1 | 7/2011 | Viola et al. |
| 2011/0168760 A1 | 7/2011 | Viola et al. |
| 2011/0174099 A1* | 7/2011 | Ross ............... A61B 17/072 74/89.32 |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0186614 A1 | 8/2011 | Kasvikis |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0240713 A1 | 10/2011 | Scirica et al. |
| 2011/0240714 A1 | 10/2011 | Whitman et al. |
| 2011/0253765 A1 | 10/2011 | Nicholas et al. |
| 2011/0257679 A1 | 10/2011 | Ishitsuki et al. |
| 2011/0272448 A1 | 11/2011 | Scirica et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1* | 12/2011 | Shelton, IV ... A61B 17/320092 227/180.1 |
| 2011/0295269 A1* | 12/2011 | Swensgard ......... A61B 17/068 606/130 |
| 2011/0295295 A1* | 12/2011 | Shelton, IV ......... A61B 17/072 606/170 |
| 2011/0309127 A1 | 12/2011 | Knodel et al. |
| 2011/0309128 A1 | 12/2011 | Okoniewski |
| 2012/0000962 A1* | 1/2012 | Racenet ........... A61B 17/07207 227/177.1 |
| 2012/0012636 A1 | 1/2012 | Beckman et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0055972 A1 | 3/2012 | Marczyk |
| 2012/0061446 A1 | 3/2012 | Knodel et al. |
| 2012/0061450 A1 | 3/2012 | Kostrzewski |
| 2012/0071866 A1 | 3/2012 | Kerr et al. |
| 2012/0074196 A1 | 3/2012 | Shelton, IV et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080476 A1 | 4/2012 | Whitman et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0138660 A1 | 6/2012 | Shelton, IV |
| 2012/0150176 A1 | 6/2012 | Weizman |
| 2012/0160892 A1 | 6/2012 | Scirica |
| 2012/0168484 A1 | 7/2012 | Scirica et al. |
| 2012/0168486 A1 | 7/2012 | Ingmanson et al. |
| 2012/0175399 A1 | 7/2012 | Shelton, IV et al. |
| 2012/0181322 A1 | 7/2012 | Whitman et al. |
| 2012/0187179 A1 | 7/2012 | Gleiman |
| 2012/0193390 A1 | 8/2012 | Racenet et al. |
| 2012/0193394 A1 | 8/2012 | Holcomb et al. |
| 2012/0193399 A1 | 8/2012 | Holcomb et al. |
| 2012/0199630 A1 | 8/2012 | Shelton, IV |
| 2012/0199631 A1* | 8/2012 | Shelton, IV ......... A61B 17/068 227/176.1 |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211542 A1 | 8/2012 | Racenet |
| 2012/0217282 A1 | 8/2012 | Beetel |
| 2012/0217283 A1 | 8/2012 | Cohen et al. |
| 2012/0223121 A1 | 9/2012 | Viola et al. |
| 2012/0223122 A1 | 9/2012 | Roy |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234899 A1 | 9/2012 | Scheib et al. |
| 2012/0234900 A1 | 9/2012 | Swayze |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255985 A1 | 10/2012 | Ma et al. |
| 2012/0255986 A1 | 10/2012 | Petty et al. |
| 2012/0273546 A1 | 11/2012 | Whitman et al. |
| 2012/0273547 A1 | 11/2012 | Hodgkinson et al. |
| 2012/0273550 A1 | 11/2012 | Scirica |

(56) References Cited

U.S. PATENT DOCUMENTS

| | | |
|---|---|---|
| 2012/0286019 A1 | 11/2012 | Hueil et al. |
| 2012/0286020 A1 | 11/2012 | Smith et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0318846 A1 | 12/2012 | Wazer et al. |
| 2012/0318847 A1 | 12/2012 | Zemlok et al. |
| 2012/0325891 A1 | 12/2012 | Farascioni et al. |
| 2012/0325893 A1 | 12/2012 | Pastorelli et al. |
| 2013/0001270 A1 | 1/2013 | Kostrzewski |
| 2013/0008937 A1 | 1/2013 | Viola |
| 2013/0012983 A1 | 1/2013 | Kleyman |
| 2013/0015231 A1 | 1/2013 | Kostrzewski |
| 2013/0015233 A1 | 1/2013 | Viola |
| 2013/0020374 A1 | 1/2013 | Ivanko |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0032627 A1 | 2/2013 | Viola |
| 2013/0032629 A1 | 2/2013 | Viola |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0037600 A1 | 2/2013 | Stopek |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068820 A1 | 3/2013 | Miller et al. |
| 2013/0068821 A1 | 3/2013 | Huitema et al. |
| 2013/0075443 A1 | 3/2013 | Giordano |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1* | 4/2013 | Kostrzewski .... A61B 17/07207 227/176.1 |
| 2013/0098968 A1 | 4/2013 | Aranyi et al. |
| 2013/0098969 A1 | 4/2013 | Scirica et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105549 A1 | 5/2013 | Holsten et al. |
| 2013/0105550 A1 | 5/2013 | Zemlok et al. |
| 2013/0105552 A1 | 5/2013 | Weir et al. |
| 2013/0105553 A1 | 5/2013 | Racenet et al. |
| 2013/0112729 A1 | 5/2013 | Beardsley et al. |
| 2013/0112730 A1 | 5/2013 | Whitman et al. |
| 2013/0112731 A1 | 5/2013 | Hodgkinson |
| 2013/0112732 A1 | 5/2013 | Aranyi et al. |
| 2013/0112733 A1 | 5/2013 | Aranyi et al. |
| 2013/0112734 A1 | 5/2013 | Aranyi et al. |
| 2013/0119109 A1 | 5/2013 | Farascioni et al. |
| 2013/0119110 A1 | 5/2013 | Scirica |
| 2013/0126581 A1 | 5/2013 | Yates et al. |
| 2013/0126582 A1 | 5/2013 | Shelton, IV et al. |
| 2013/0126583 A1 | 5/2013 | Hueil et al. |
| 2013/0126586 A1 | 5/2013 | Zhang et al. |
| 2013/0140342 A1 | 6/2013 | Milliman et al. |
| 2013/0140343 A1 | 6/2013 | Knodel |
| 2013/0144333 A1 | 6/2013 | Viola |
| 2013/0264370 A1* | 10/2013 | Chen ............... A61B 17/07207 227/175.2 |

FOREIGN PATENT DOCUMENTS

| | | |
|---|---|---|
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0600182 | 6/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 2 090 233 | 8/2009 |
| EP | 2 090 245 | 8/2009 |
| EP | 2 090 247 | 8/2009 |
| EP | 2 236 098 | 10/2010 |
| EP | 2 329 773 | 6/2011 |
| EP | 2 586 382 | 5/2013 |
| EP | 2 653 114 | 10/2013 |

(56) References Cited

FOREIGN PATENT DOCUMENTS

| | | |
|---|---|---|
| FR | 2542188 | 9/1984 |
| FR | 2660851 | 10/1991 |
| FR | 2681775 | 10/1991 |
| GB | 1352554 | 4/1971 |
| GB | 1552185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| JP | 51-149985 | 6/1975 |
| JP | 2001-872725 | 4/2001 |
| SU | 659146 | 4/1979 |
| SU | 728848 | 5/1980 |
| SU | 980703 | 12/1982 |
| SU | 990220 | 1/1983 |
| WO | WO 8302247 | 7/1983 |
| WO | WO 89/10094 | 11/1989 |
| WO | WO 9210976 | 9/1992 |
| WO | WO 9308754 | 5/1993 |
| WO | WO 9314706 | 8/1993 |
| WO | WO 2004/032760 | 4/2004 |

OTHER PUBLICATIONS

U.S. Appl. No. 13/923,557, filed Jun. 21, 2013, Williams et al.
U.S. Appl. No. 13/923,725, filed Jun. 21, 2013, Williams et al.
U.S. Appl. No. 13/923,832, filed Jun. 21, 2013, Williams et al.
U.S. Appl. No. 13/924,054, filed Jun. 21, 2013, Williams et al.
European Search Report dated Jul. 24, 2014 issued in European Appln. No. EP 14 15 9099.
European Search Report dated Jul. 25, 2014 issued in European Appln. No. EP 14 15 9037.
European Search Report dated Jul. 25, 2014 issued in European Appln. No. EP 14 15 9073.
European Search Report dated Jul. 25, 2014 issued in European Appln. No. EP 14 15 9075.
European Search Report dated Jul. 29, 2014 issued in European Appln. No. EP 14 15 9118.
European Office Action dated Nov. 16, 2015, issued in Ep Application No. 14 159 073.
European Office Action dated Jun. 22, 2015 (received Jul. 24, 2015), issued in European Application No. 14159075.
Chinese Office Action dated Mar. 14, 2017, issued in CN Application No. 2014100932839.
Chinese Office Action dated Mar. 14, 2017, issued in CN Application No. 201410093286.

\* cited by examiner

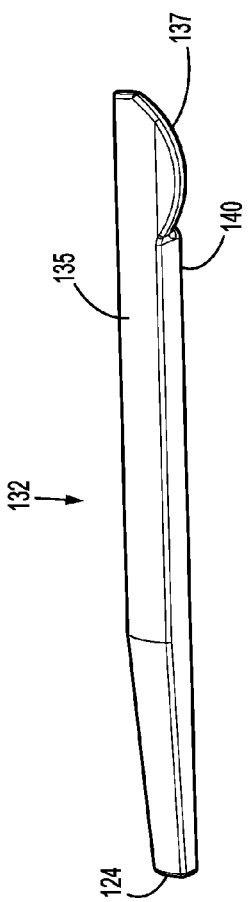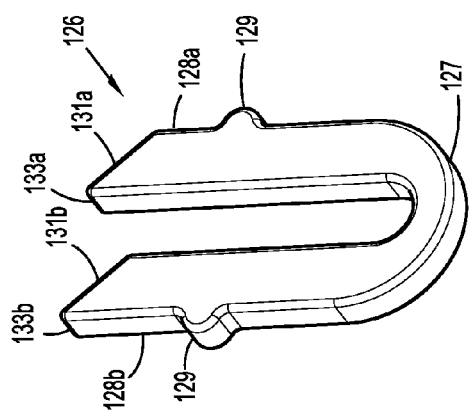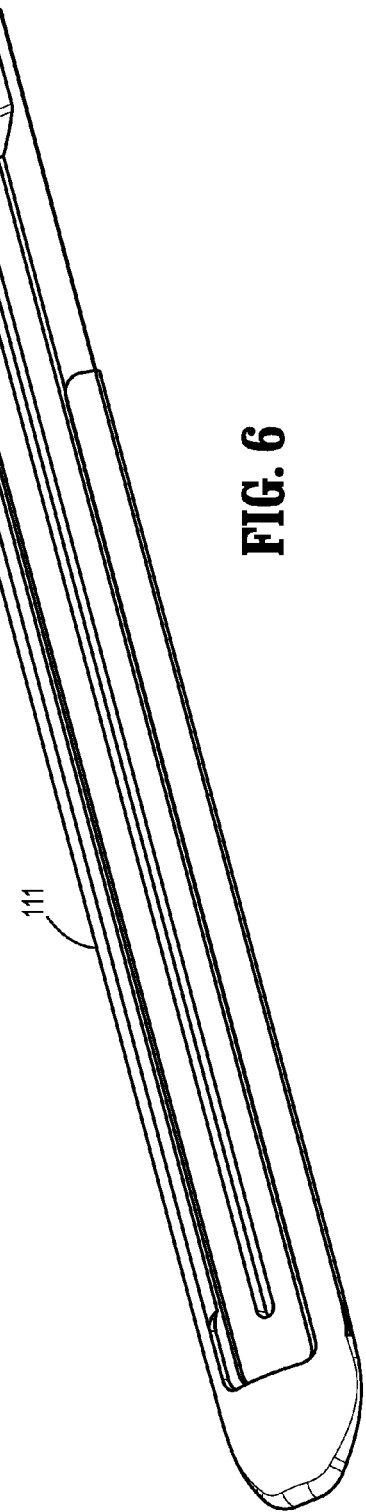

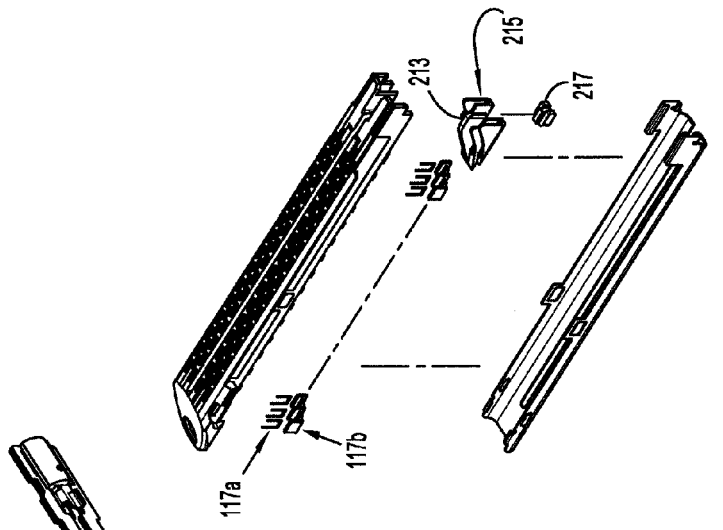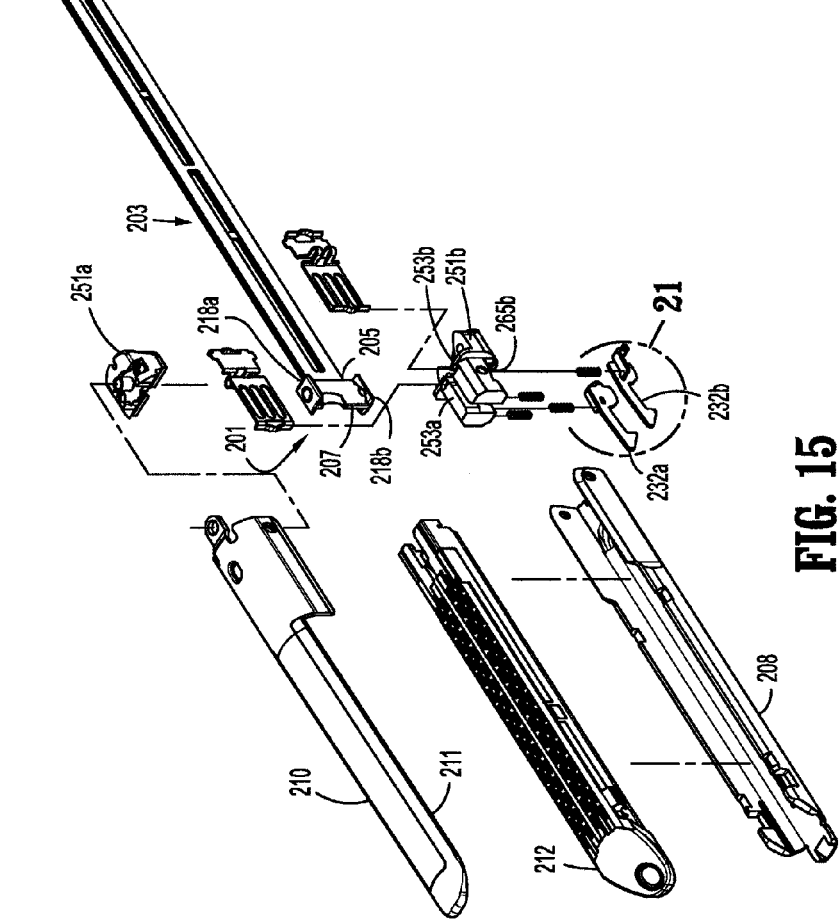

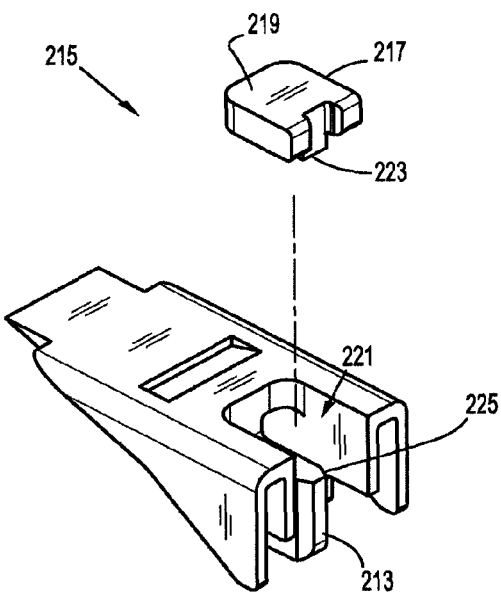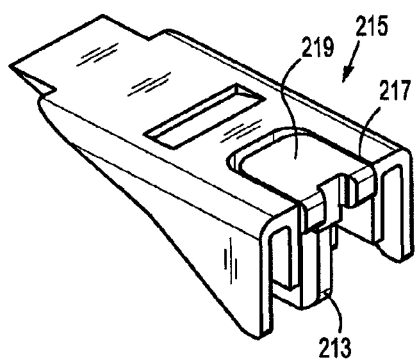
FIG. 17  FIG. 18
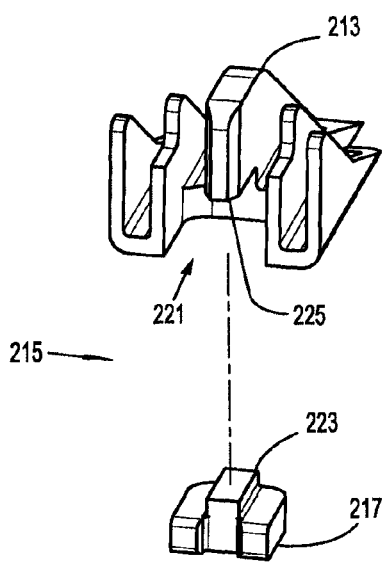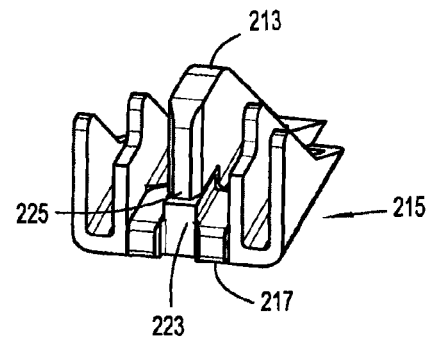
FIG. 19  FIG. 20

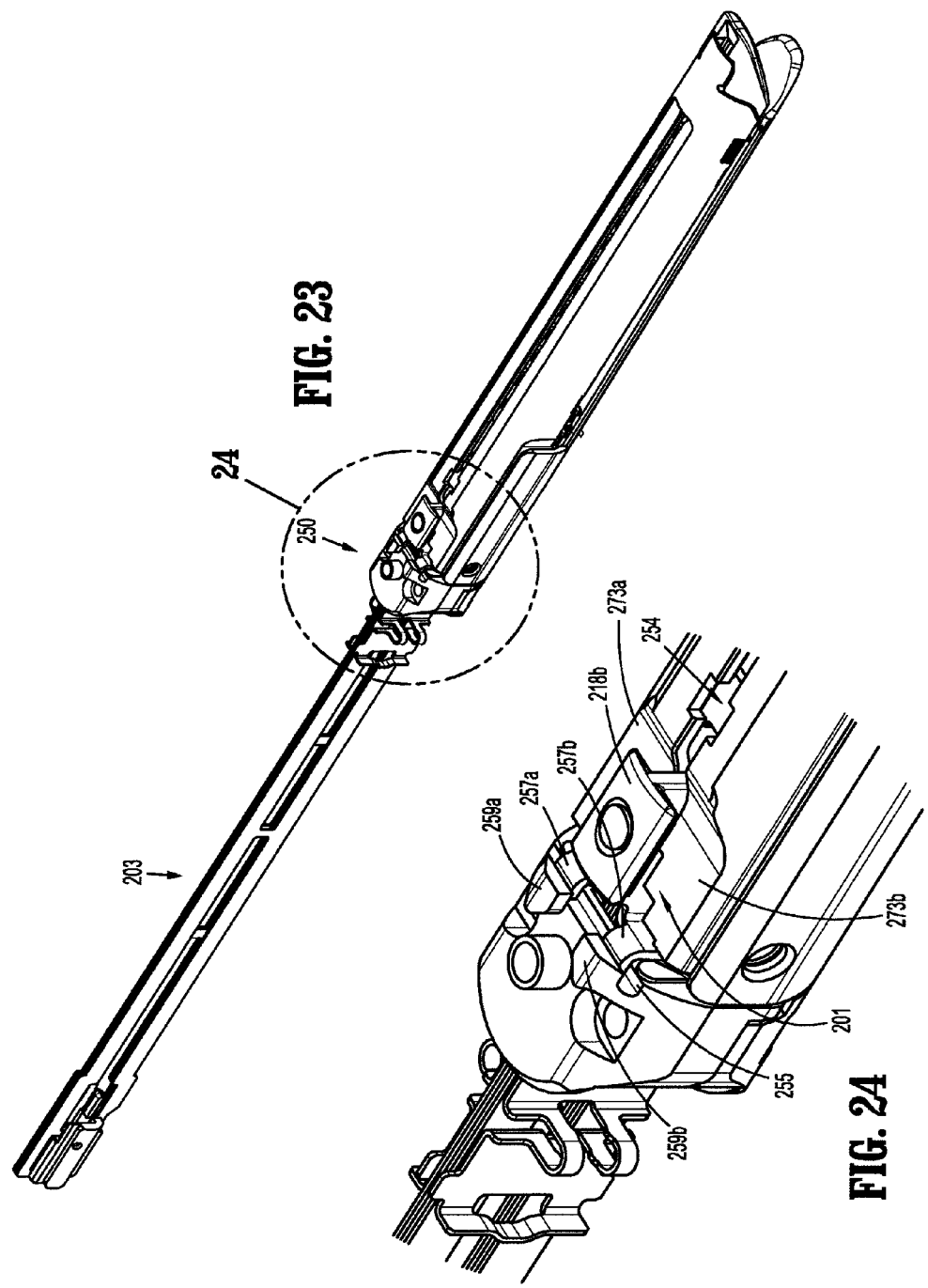

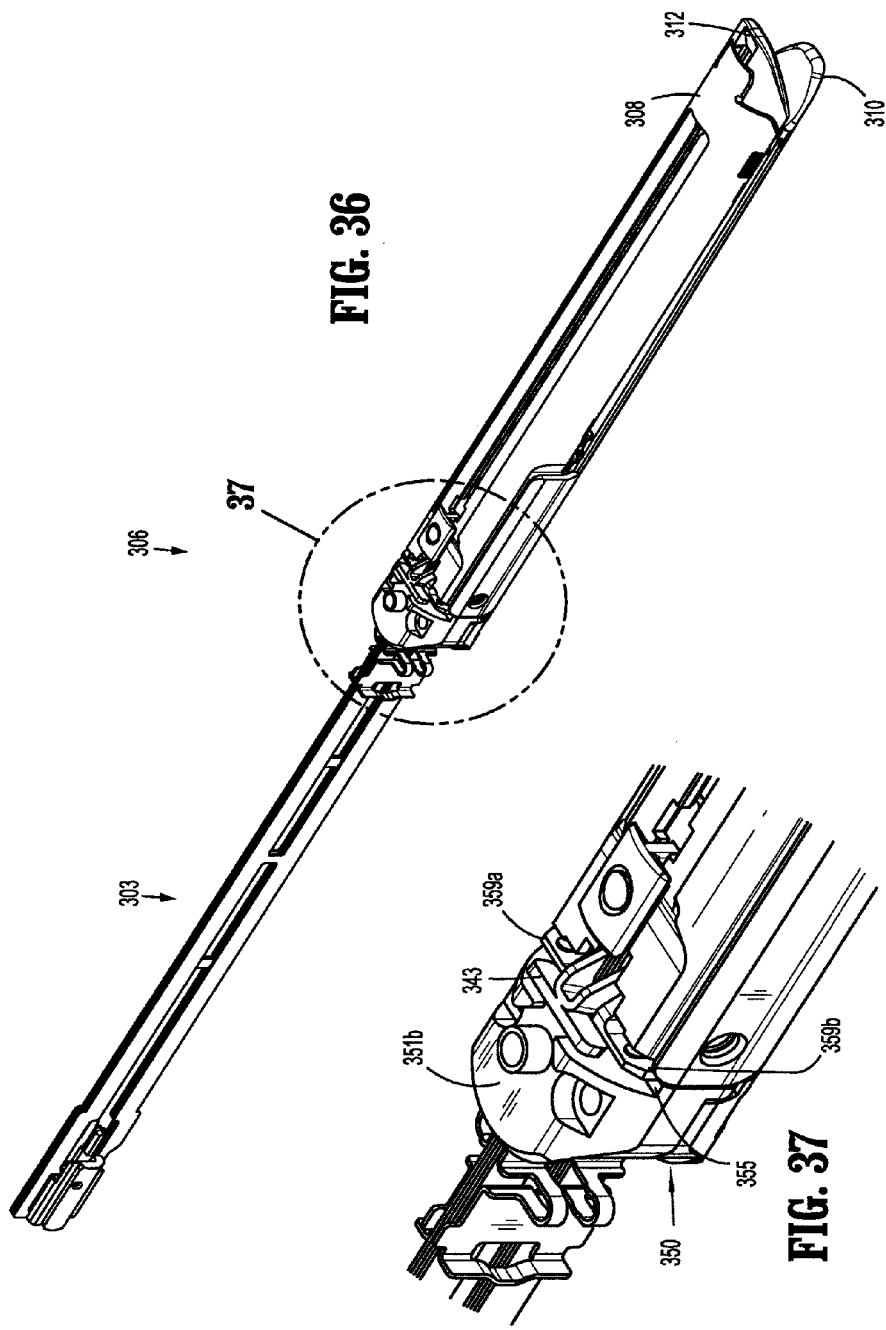

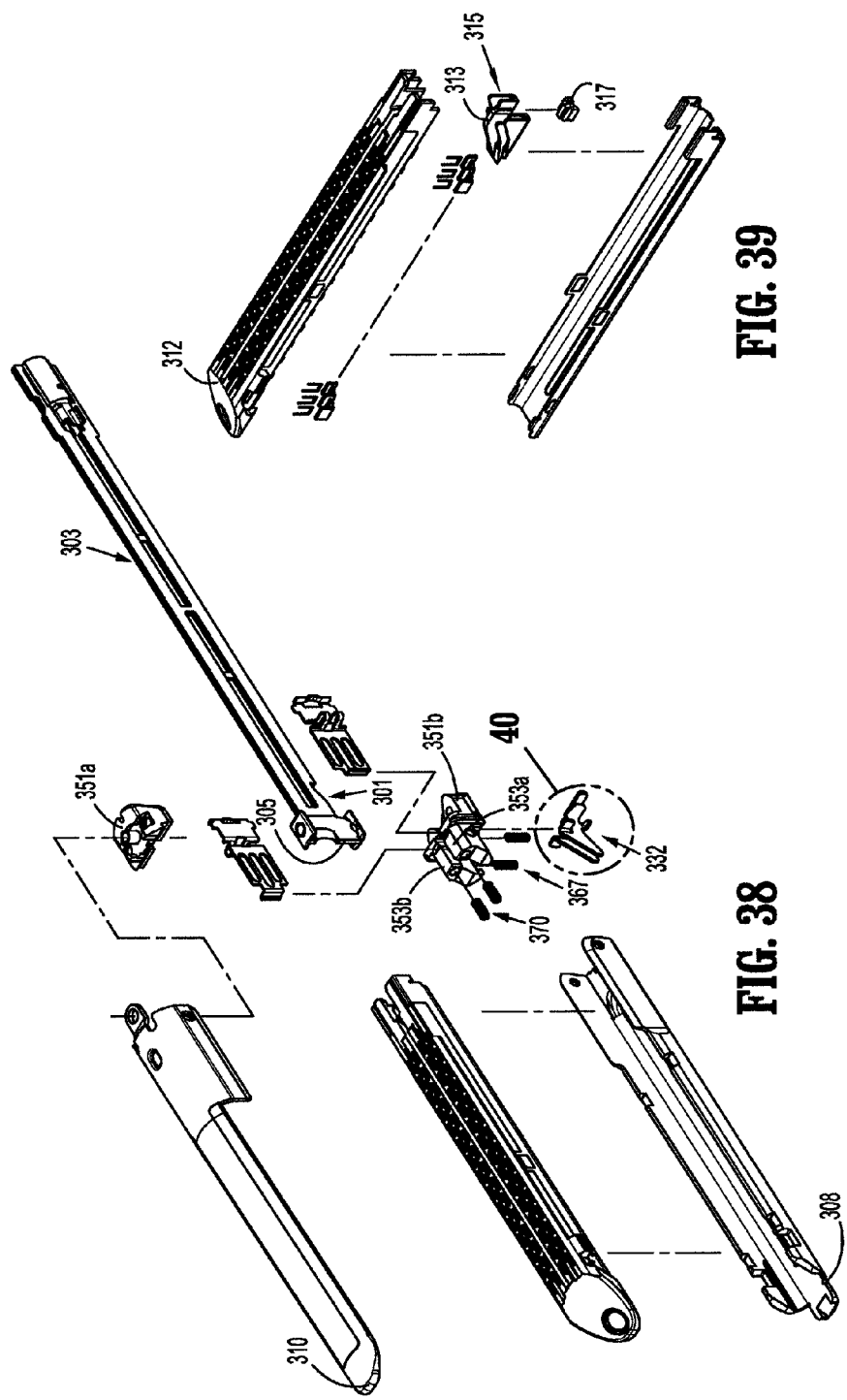

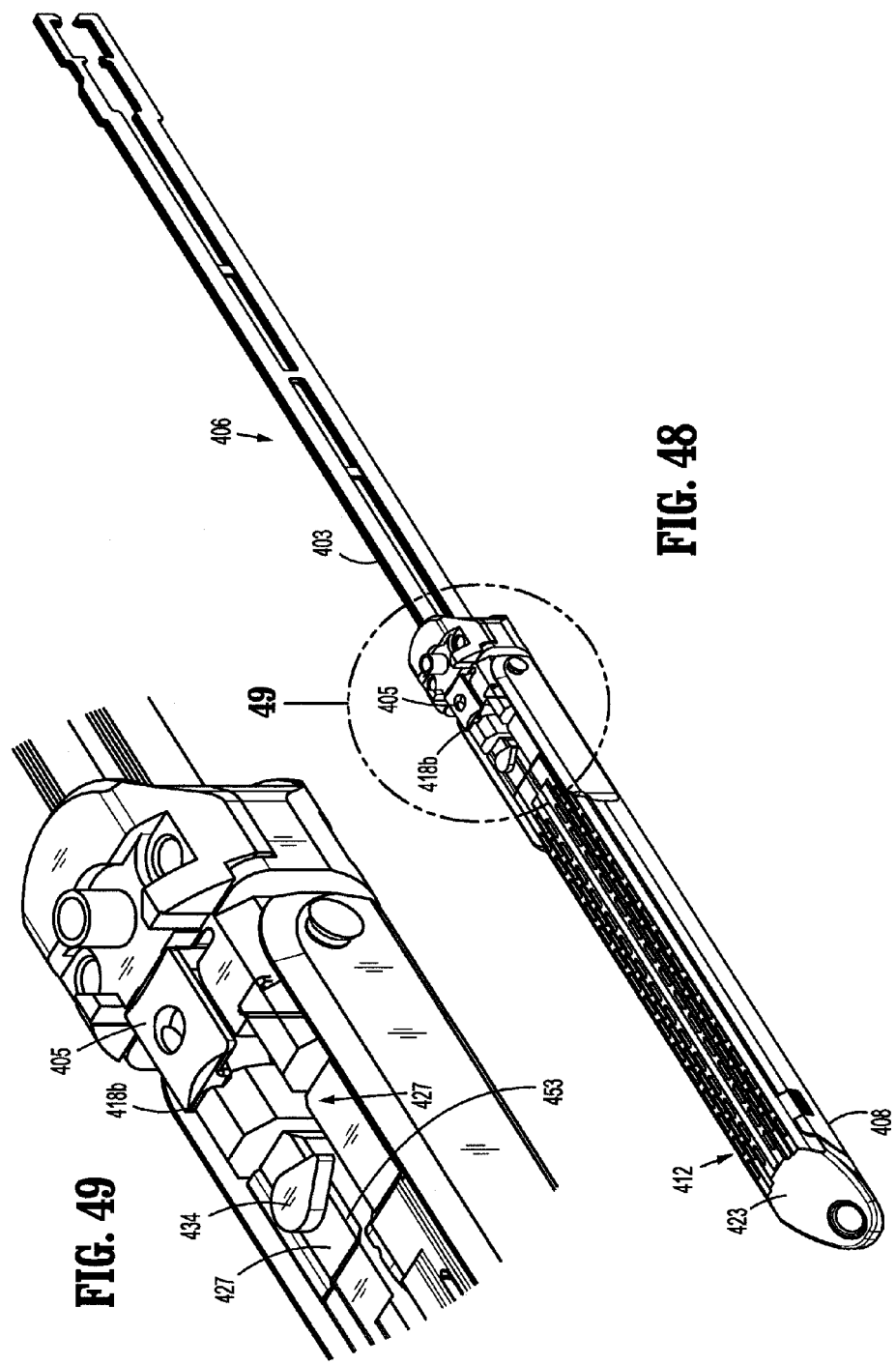

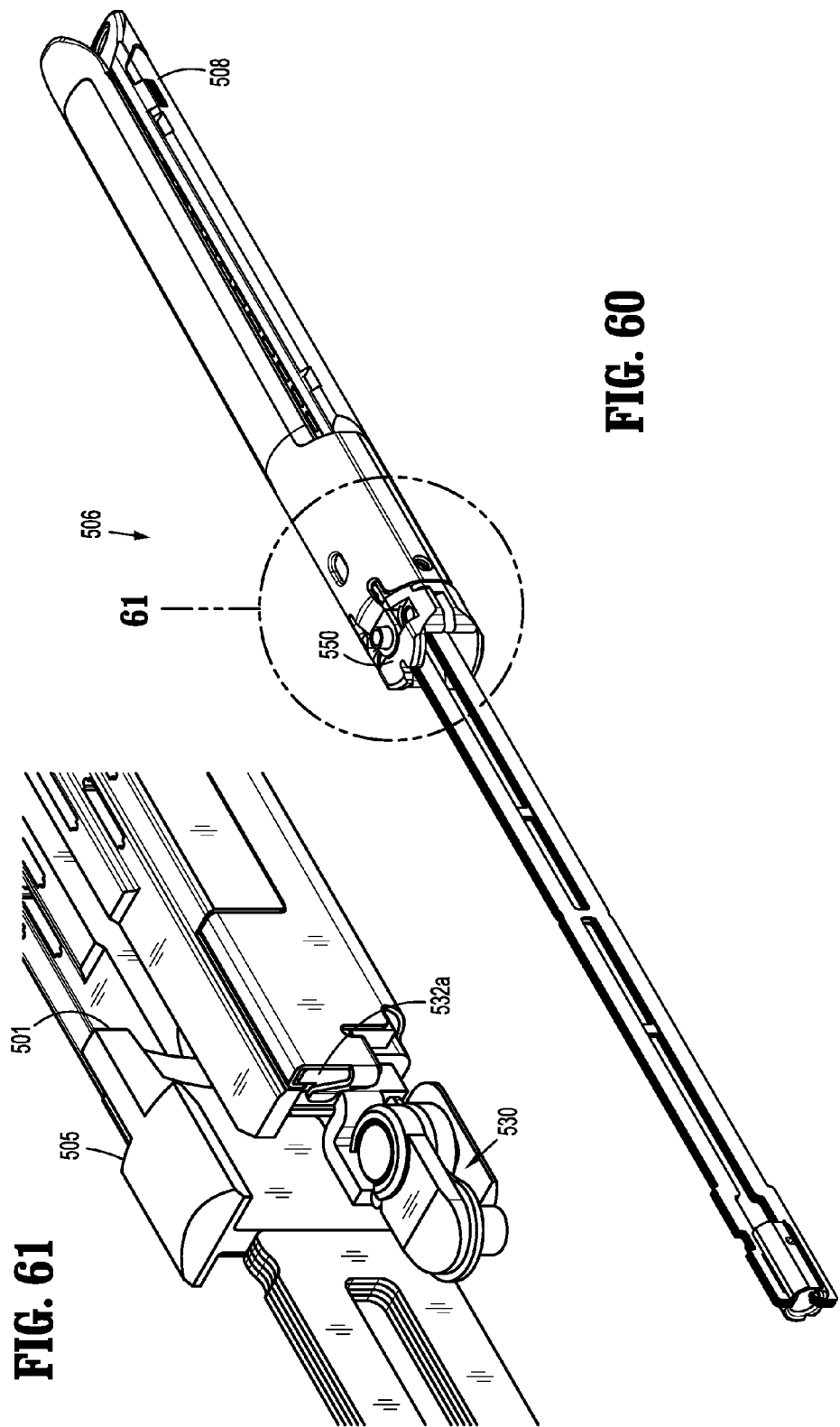

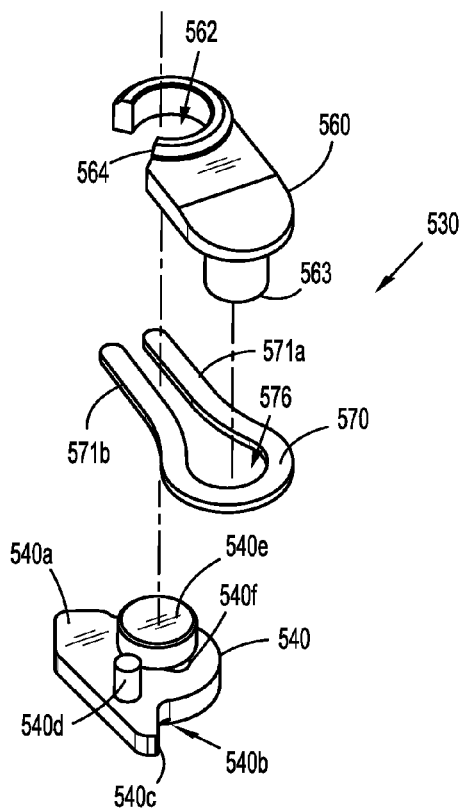
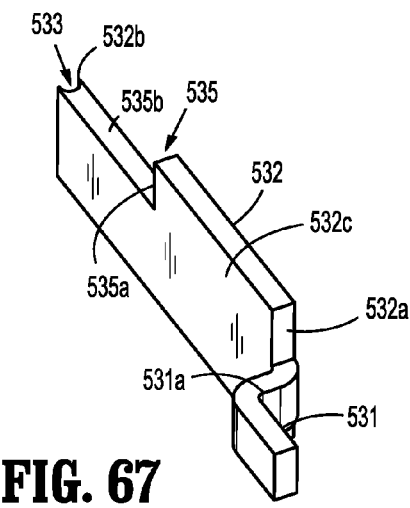
FIG. 67
FIG. 68
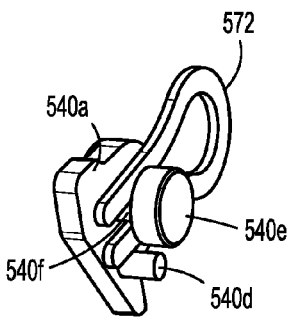
FIG. 69
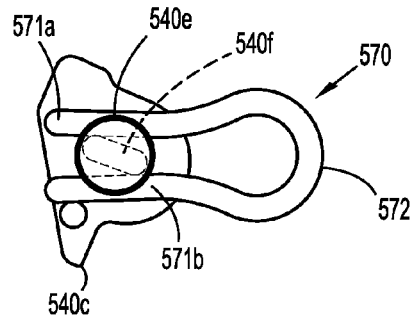
FIG. 70A
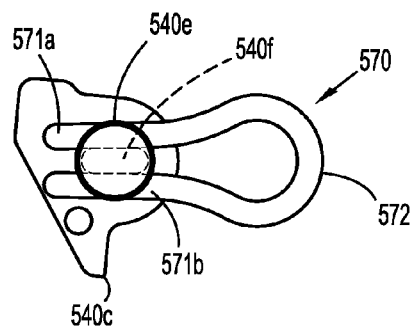
FIG. 70B
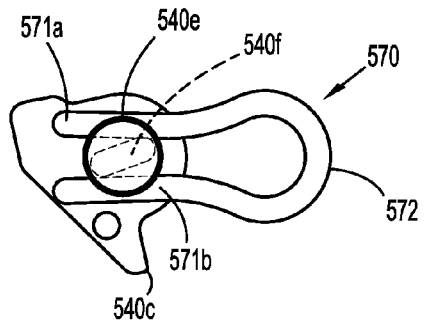
FIG. 70C

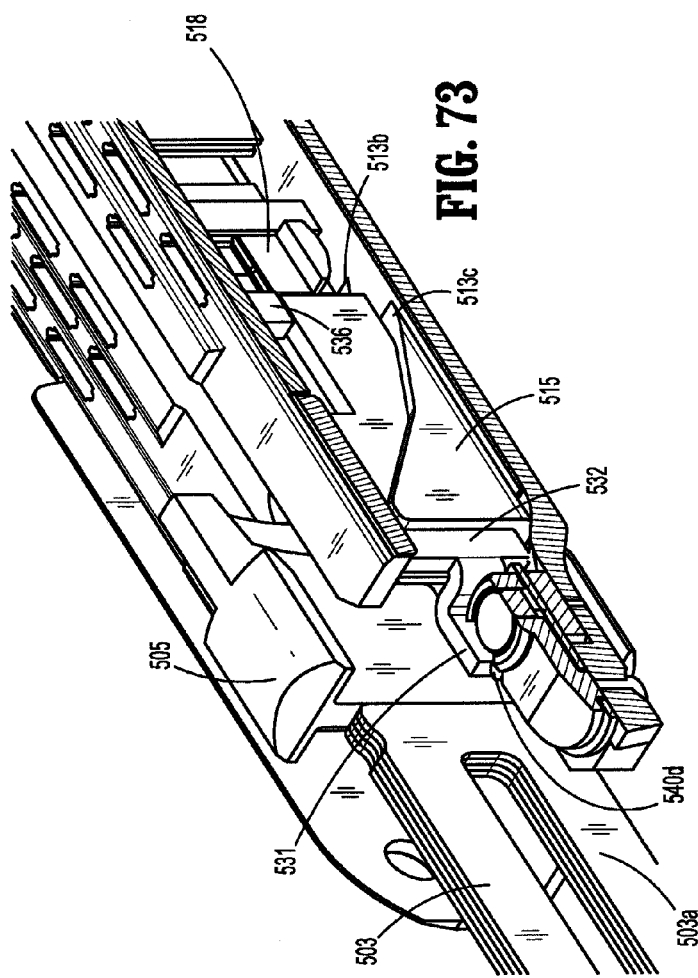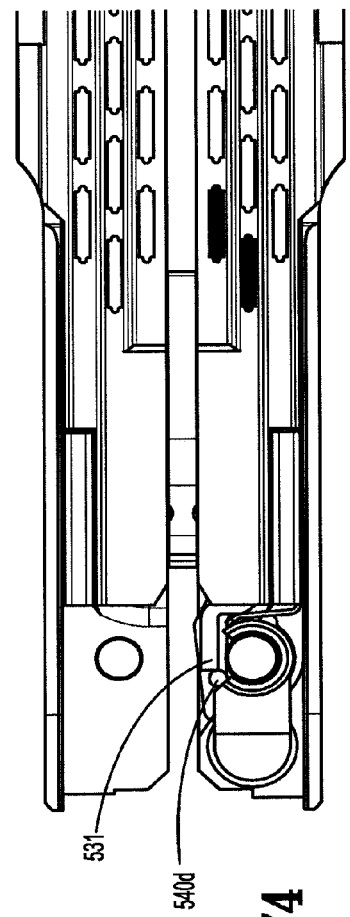

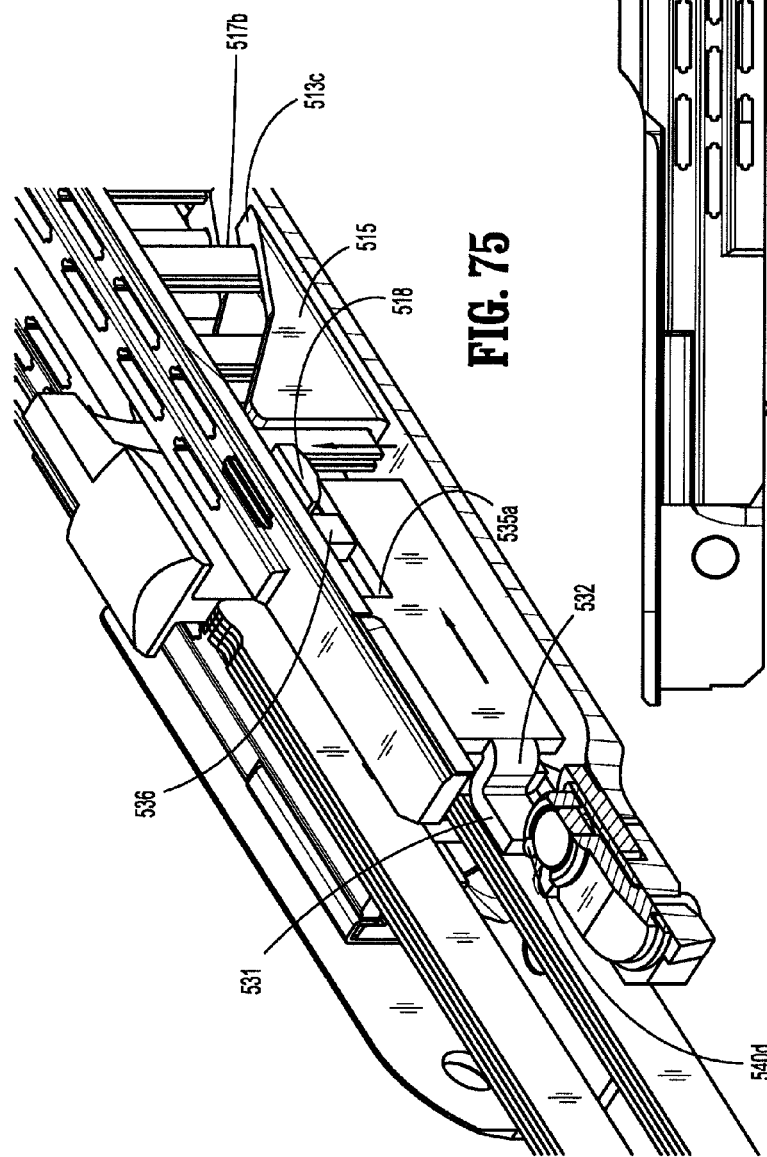
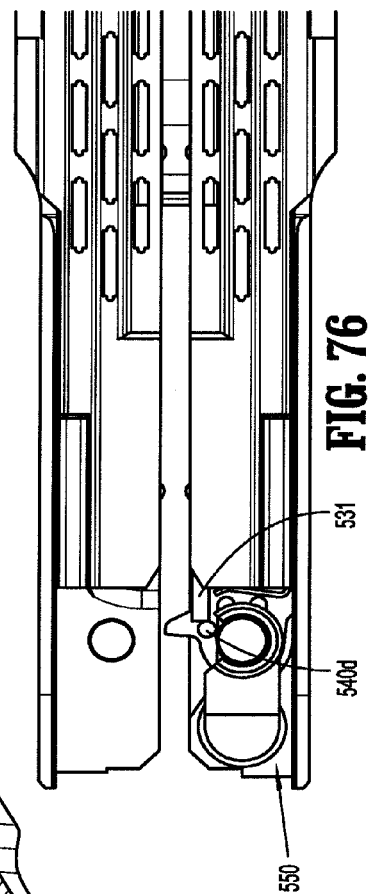

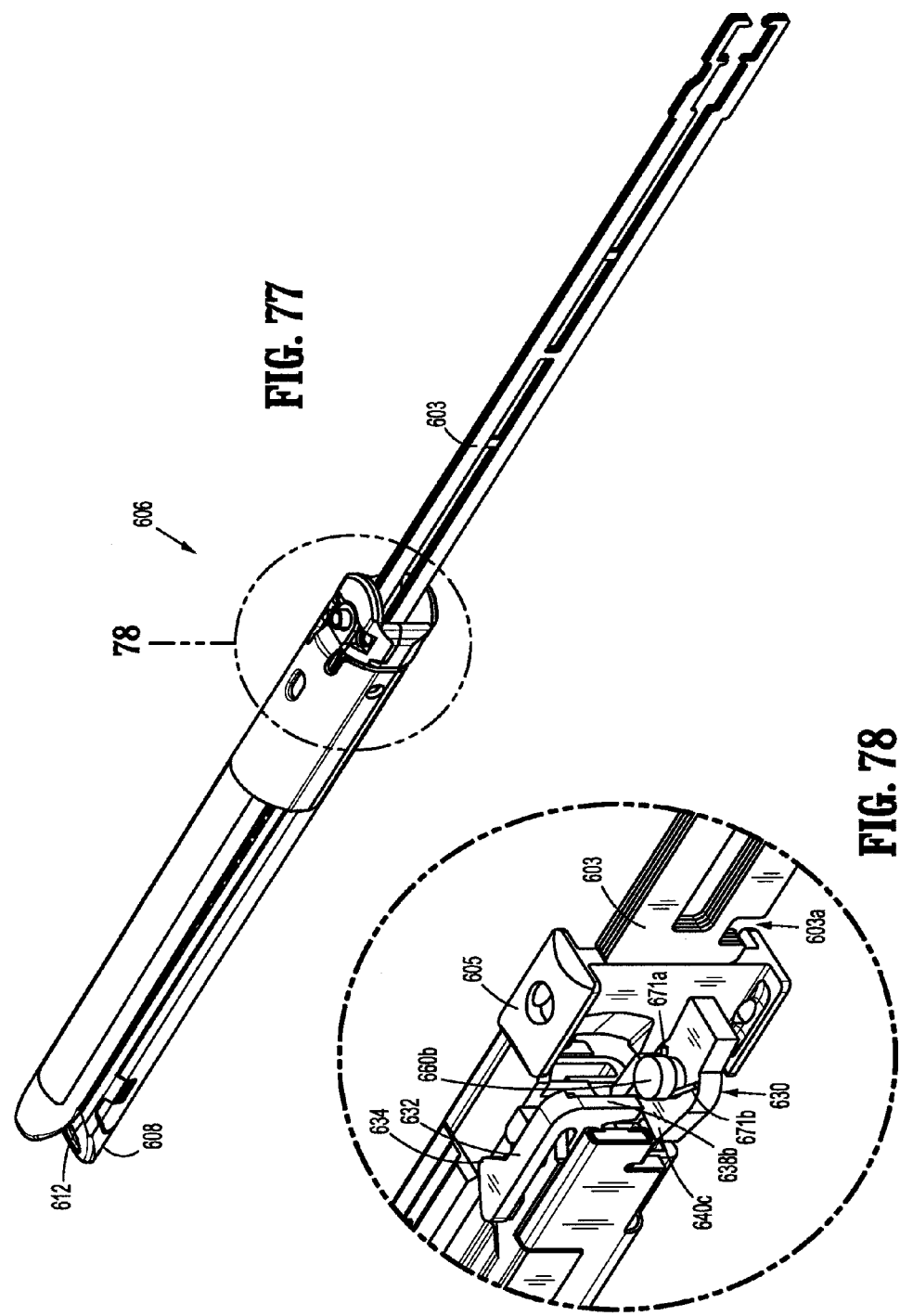

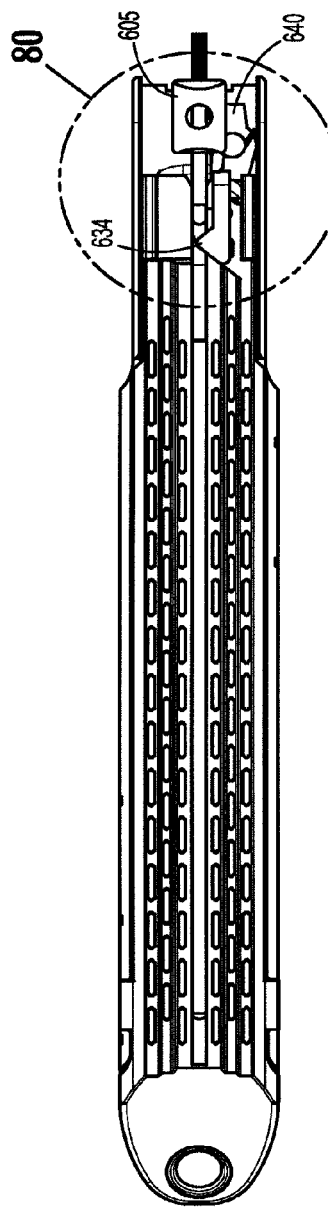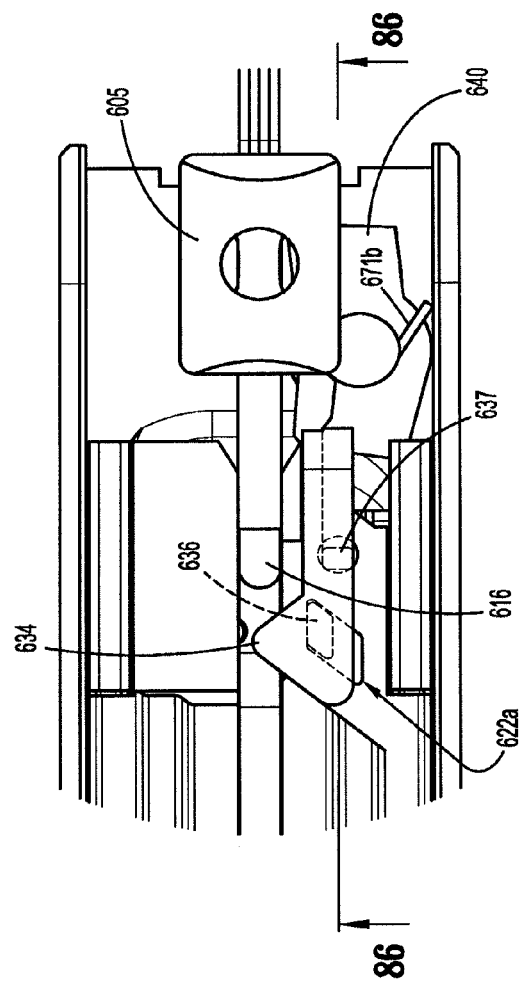
FIG. 79
FIG. 80

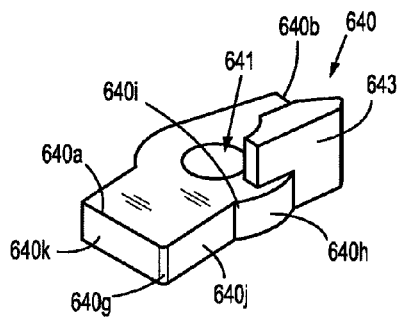
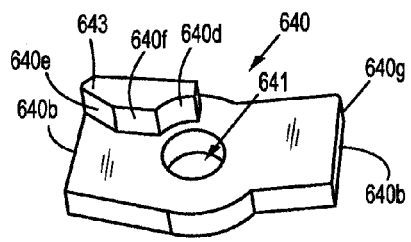
FIG. 82  FIG. 83
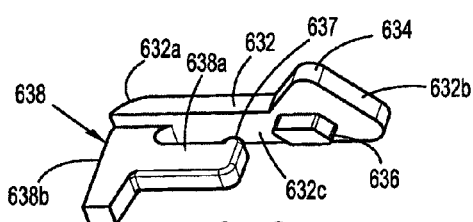
FIG. 84
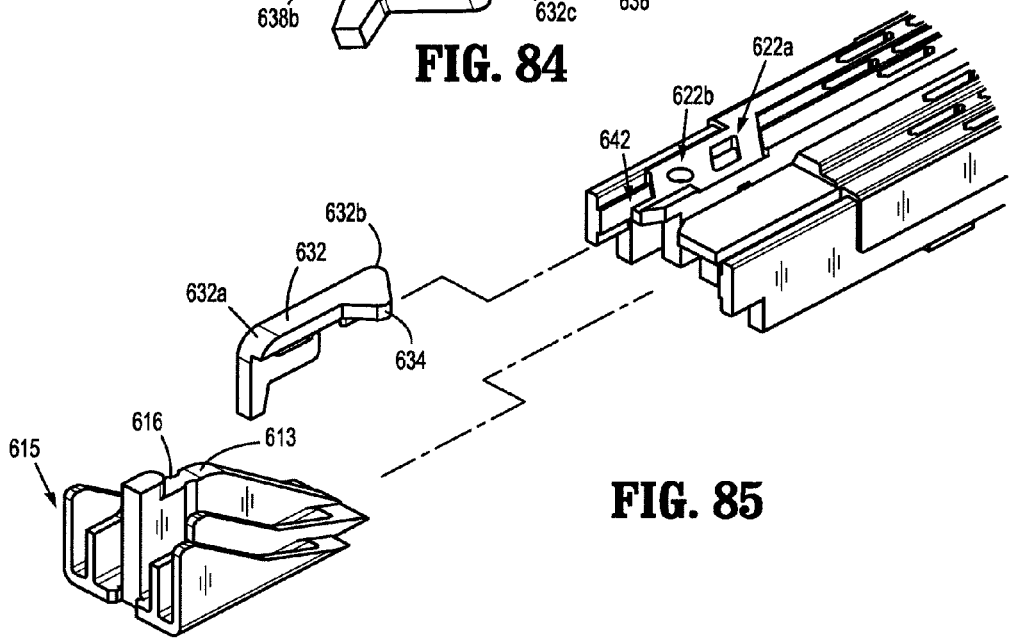
FIG. 85

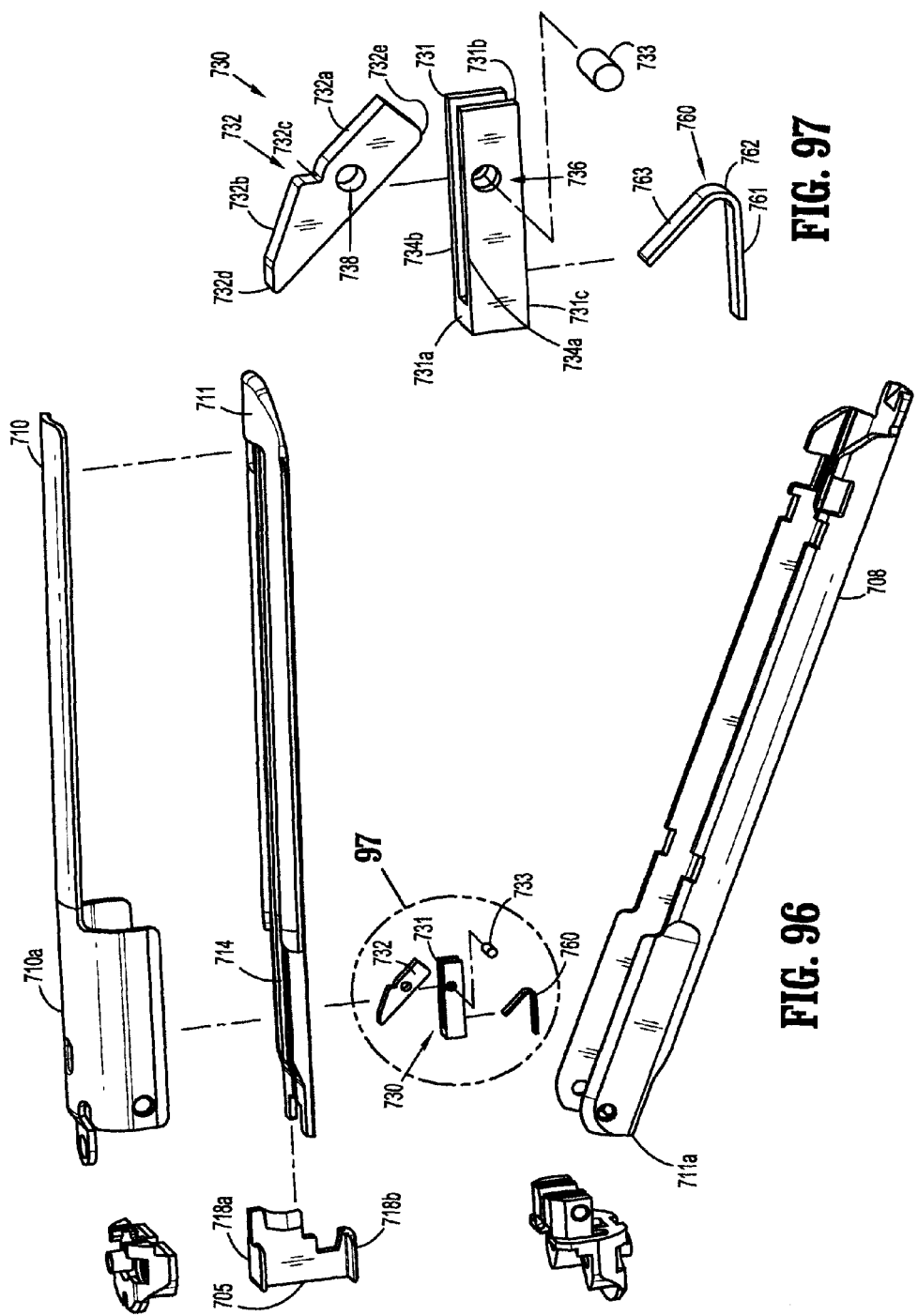

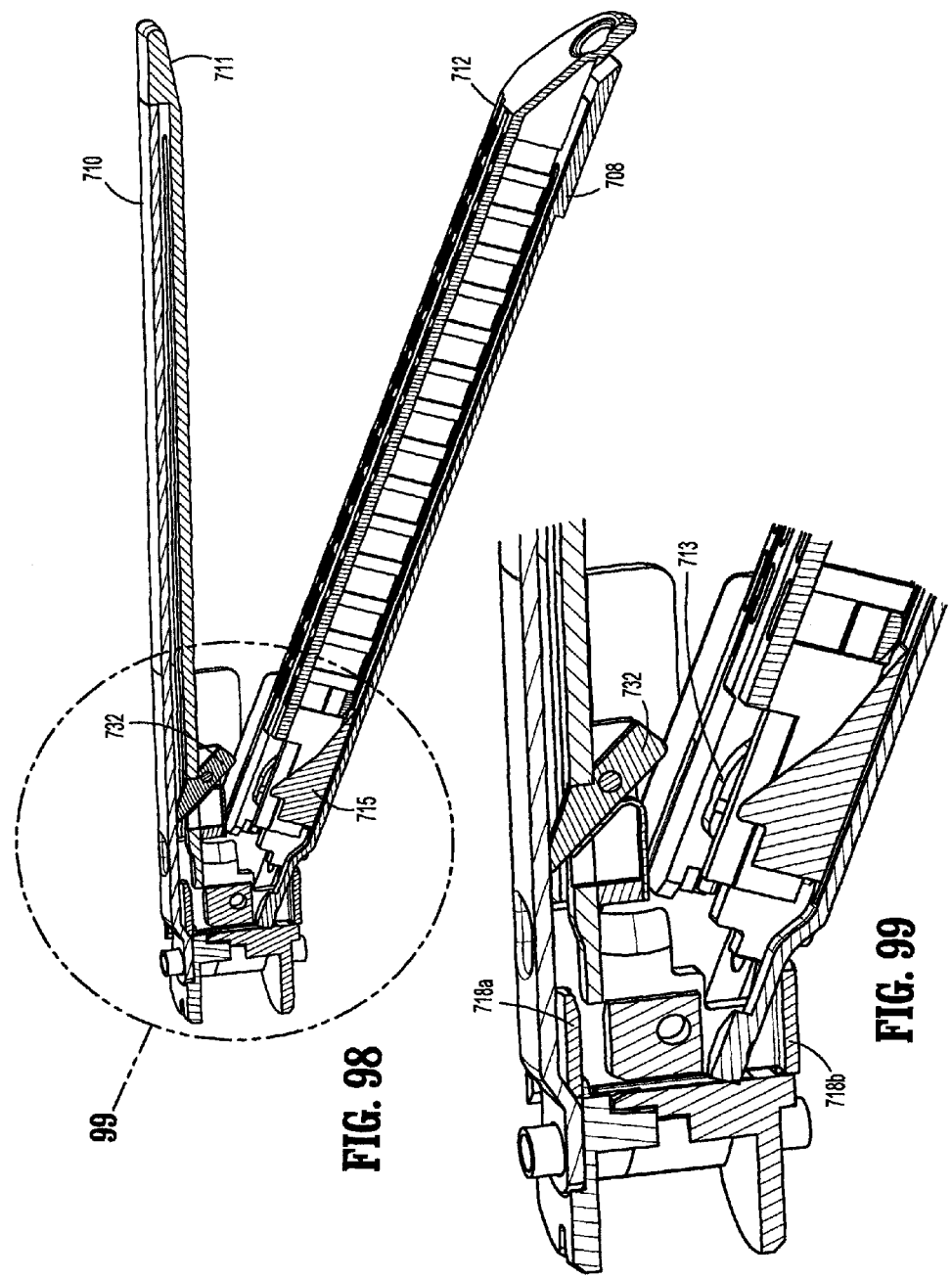

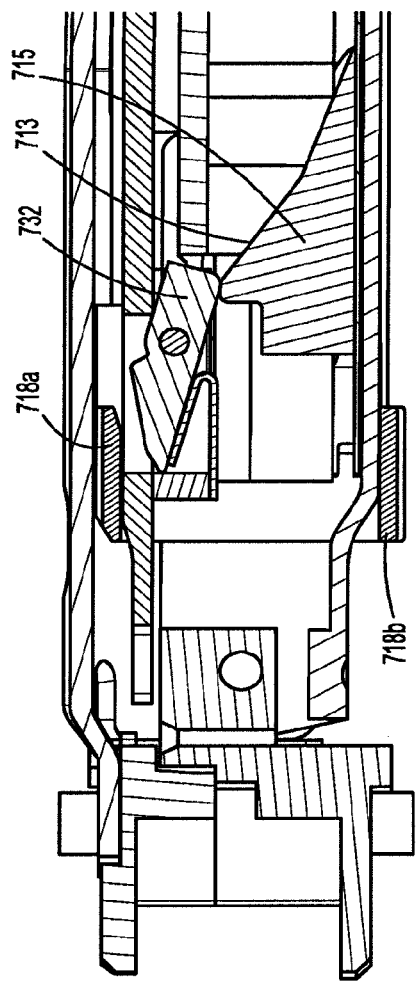
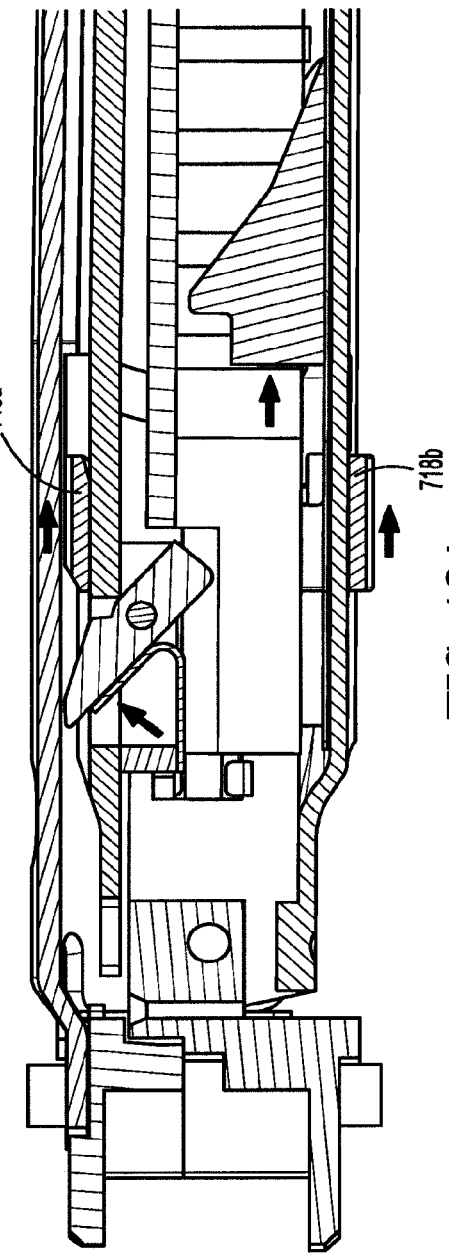
FIG. 100
FIG. 101

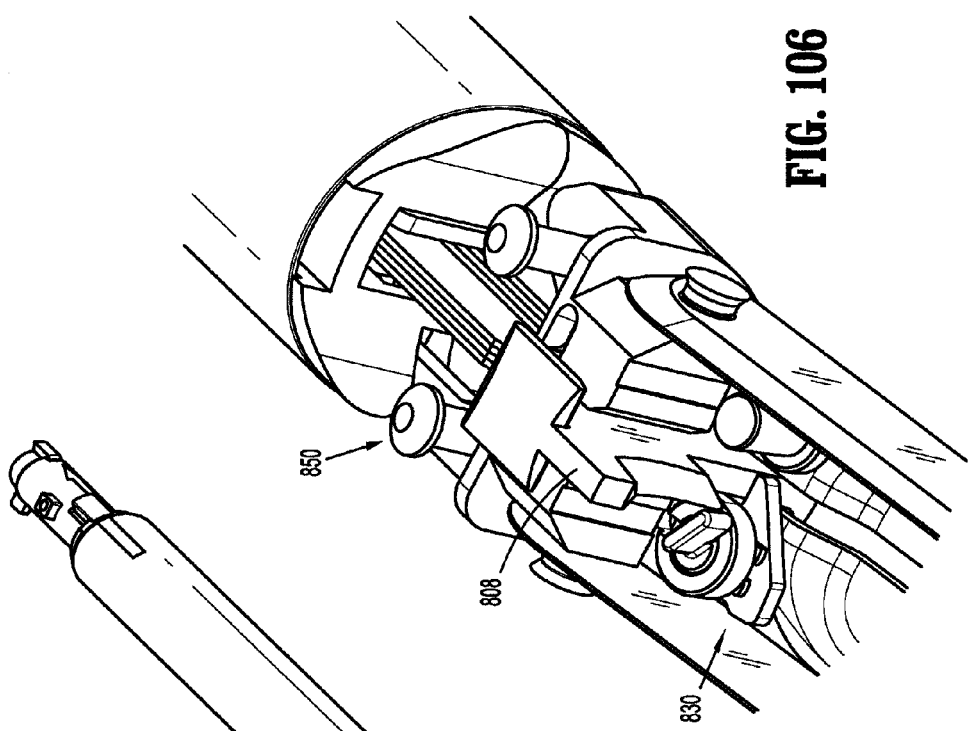
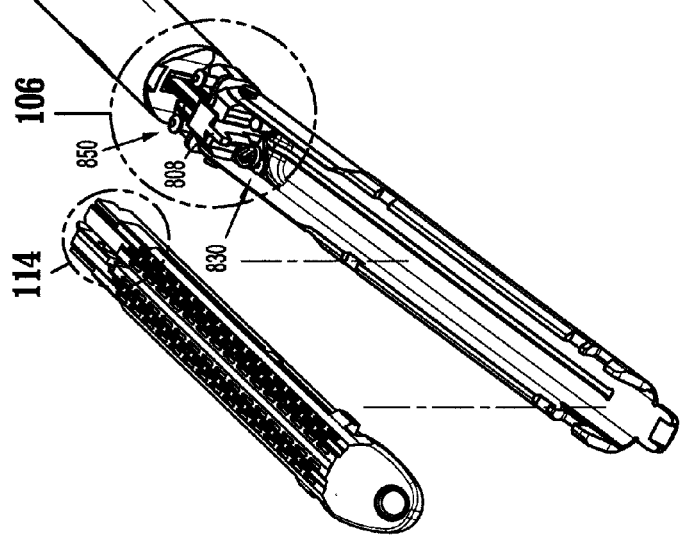
FIG. 105
FIG. 106

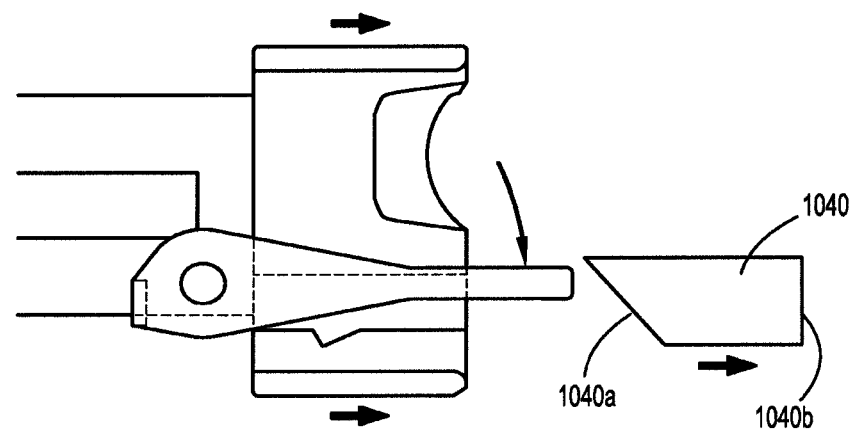
FIG. 131
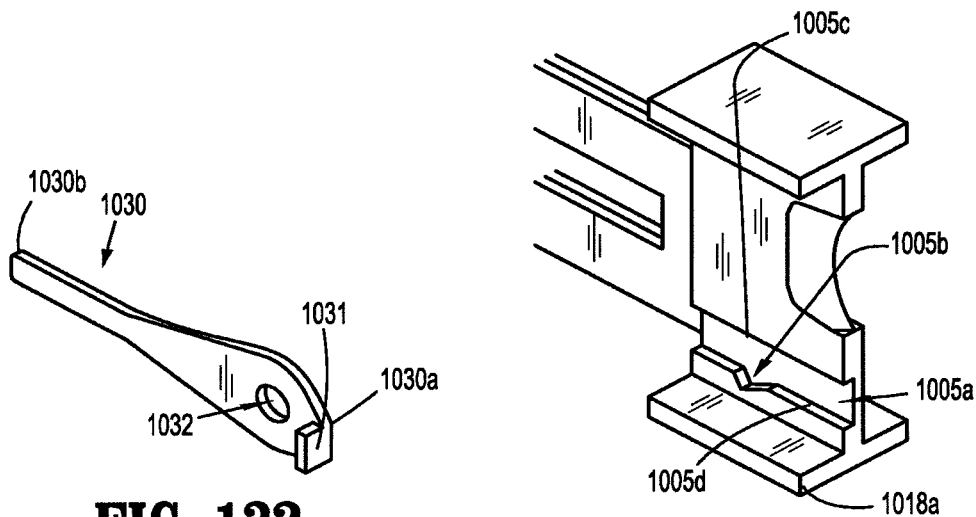
FIG. 132
FIG. 133

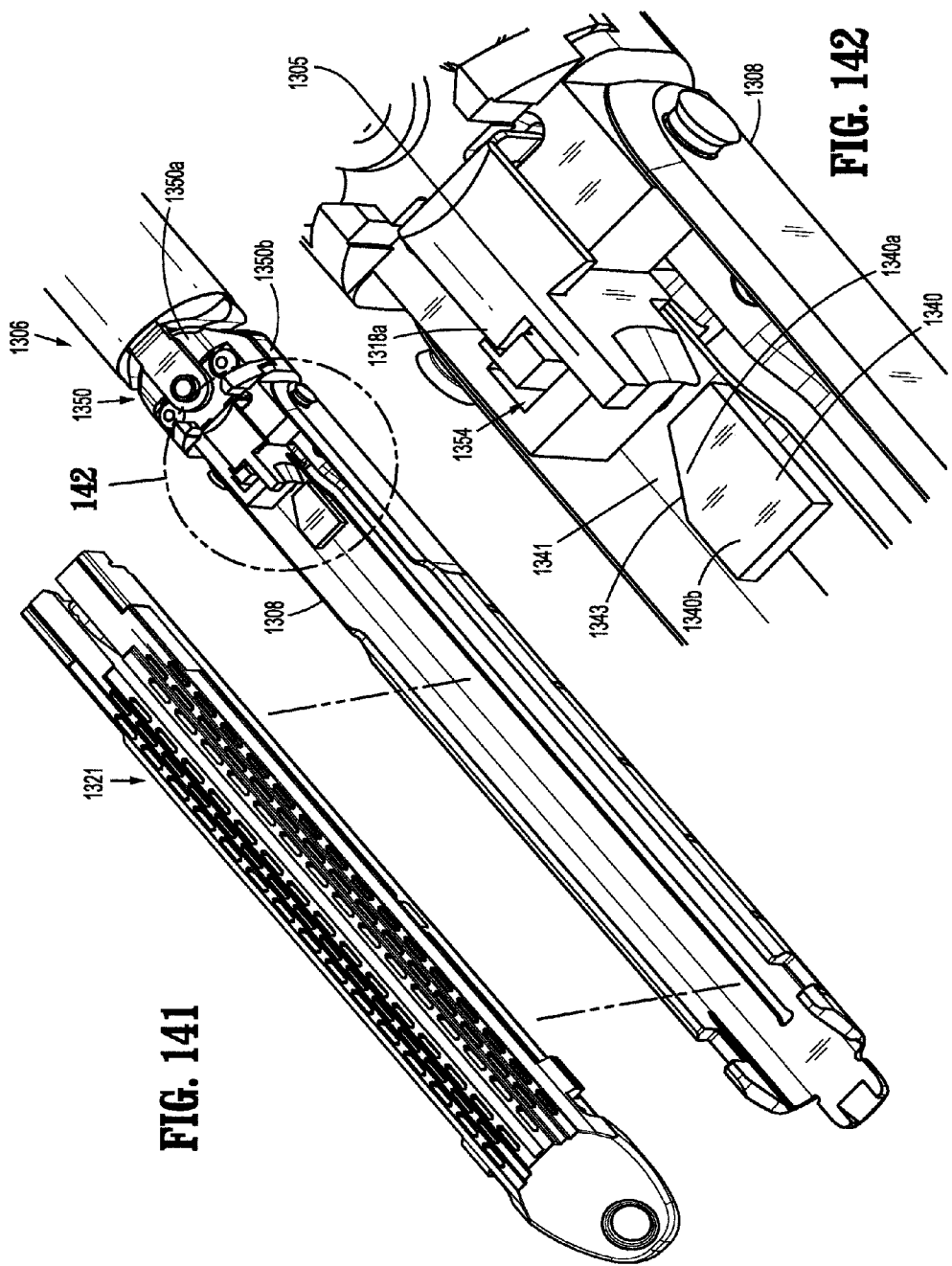

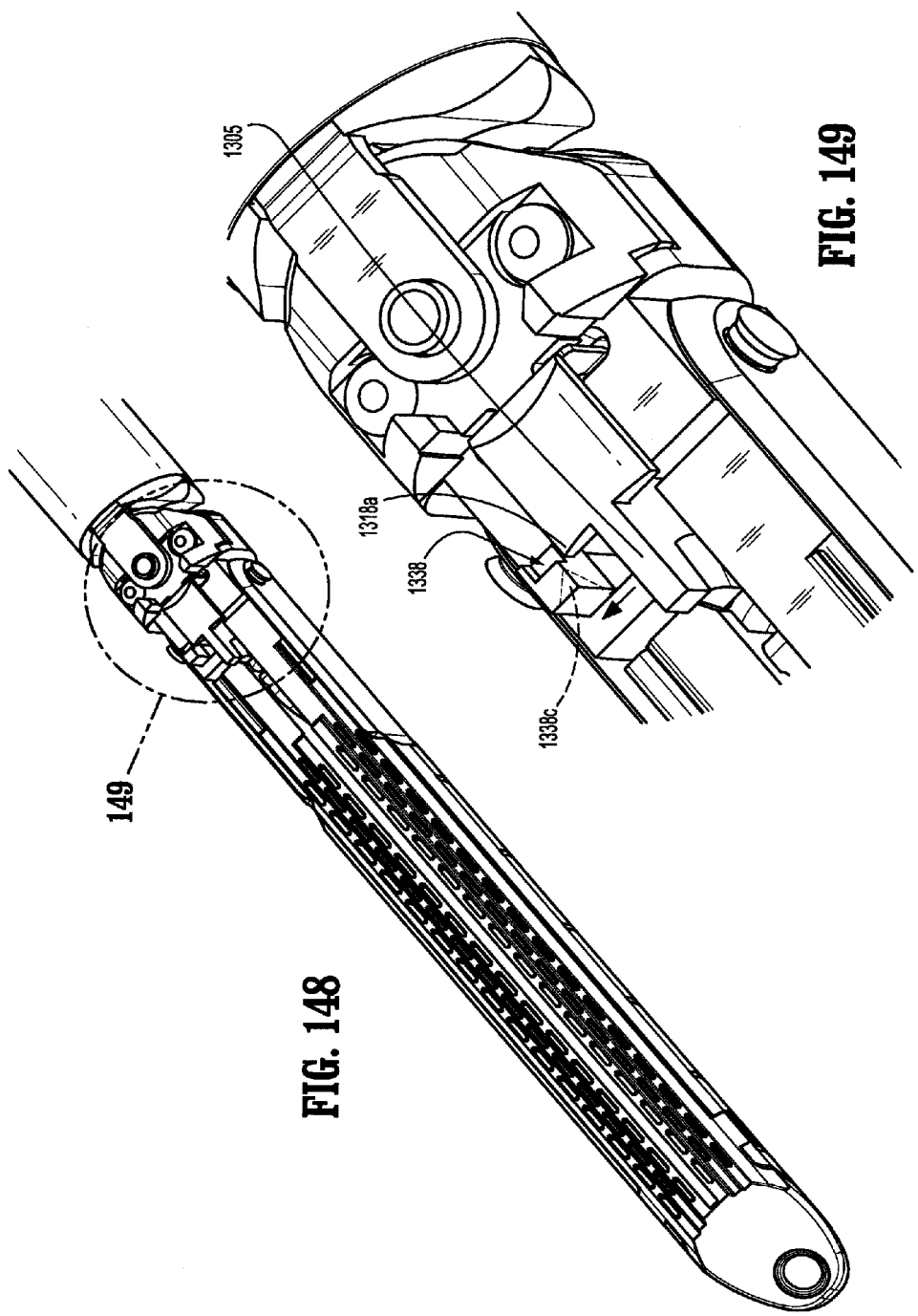

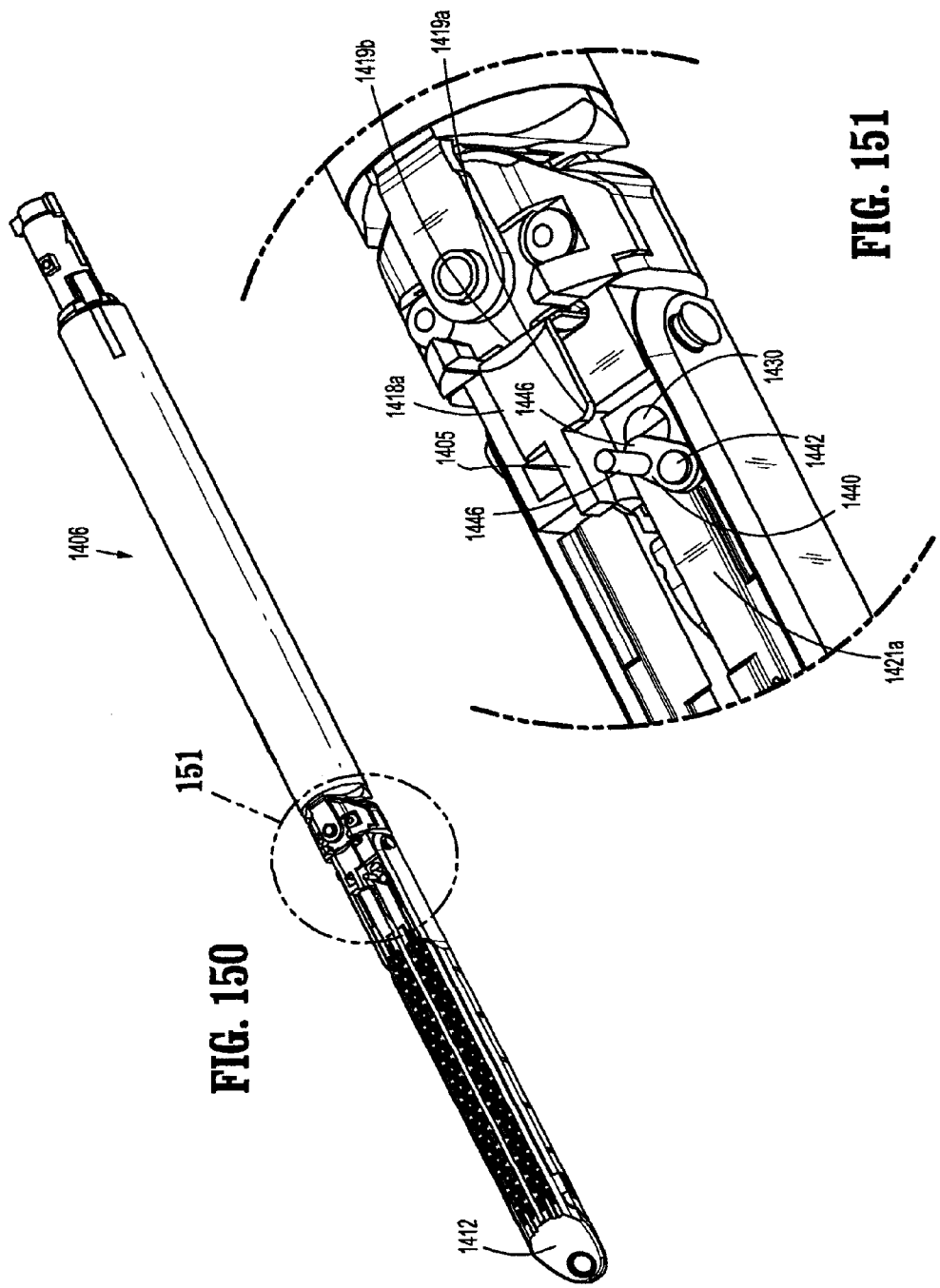

SURGICAL STAPLING APPARATUS

CROSS-REFERENCE TO RELATED APPLICATIONS

This application claims the benefit of and priority to U.S. Provisional Patent Application No. 61/779,873, filed Mar. 13, 2013, the entire disclosure of which is incorporated by reference herein.

BACKGROUND

Technical Field

The present disclosure relates to surgical stapling apparatuses. More particularly, the present disclosure relates to surgical stapling apparatuses including knife drive lockout mechanisms.

Description of Related Art

Surgical stapling apparatuses that are configured to staple and, subsequently, sever tissue are well known in the art. Such stapling apparatuses, typically, include, a housing and an elongated member that extends from the housing. In certain instances, a multi use loading unit (MULU) that includes a reload may be configured to releasably couple to a distal end of the elongated member. Alternatively, the reload may be fixedly supported at the distal end of the elongated member. In either of the aforementioned reload configurations, an anvil and cartridge may be provided on jaws of the reload and configured to staple tissue. A knife (or other suitable device) may be utilized to sever the stapled tissue. The knife may be actuated via one or more actuation devices operably associated with the surgical stapling apparatus and translated through the anvil and cartridge to sever the staple tissue.

While the aforementioned reload configurations provide numerous advantages, it may be desirable to prevent inadvertent firing of the knife of the surgical stapler when a staple cartridge is not installed or is spent.

SUMMARY

As can be appreciated, surgical stapling apparatuses that include knife drive lockout mechanisms may prove useful in the surgical arena.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides a surgical stapling apparatus (stapler). The stapler includes a housing and an elongated member that extends therefrom. The elongated member is configured to operably support a reload at a distal end thereof. A cartridge is configured to selectively couple to a first jaw member of the reload. The cartridge includes one or more resilient members thereon. An anvil operably supported on a second jaw member of the reload is configured to compress one or more fasteners ejected from the cartridge. The anvil includes one or more locking members thereon. A knife is configured to translate through the cartridge and anvil when the first and second jaw members are in a closed configuration. Engagement between the knife and the resilient member(s) causes the resilient member(s) to move from an initial configuration that allows the knife to travel distally past the at least one locking member when the knife is fired to a final configuration that allows the locking member(s) to engage the knife. The surgical stapling apparatus may include a firing mechanism that is configured to translate the knife through the anvil and cartridge.

The anvil and cartridge may each include one or more recesses disposed thereon that are configured for receipt of the resilient member(s) therethrough. The recess(es) on the anvil and cartridge may be in vertical registration with one another.

The resilient member(s) may be in the form of a spring-clip. The spring clip may include a generally arcuate configuration that is defined by opposing sidewalls. One or both of the opposing sidewalls may have one or more flanges thereon configured to releasably engage a tissue contacting surface of cartridge.

The locking member(s) may include a generally elongated configuration and may include one or more cam surfaces that are disposed at a proximal end thereof. The cam surface(s) may be configured to engage a flange disposed on a top portion of the knife. In the initial configuration, the resilient member(s) may be configured to raise the locking member(s) a predetermined distance above a tissue contacting surface of the cartridge so as to prevent engagement between the cam surface(s) and the flange such that the knife is allowed to travel distally past the locking member(s) when the knife is fired.

An aspect of the present disclosure provides a surgical stapling apparatus (stapler). The stapler includes a housing and an elongated member that extends therefrom. The elongated member is configured to operably support a reload at a distal end thereof. The reload includes first and second jaw members. The first jaw member is configured to operably couple to a cartridge that includes one or more resilient member(s) thereon. An anvil operably supported on a second jaw member of the reload is configured to compress one or more fasteners ejected from the cartridge. The anvil includes one or more locking member(s) thereon. A knife is configured to translate through the cartridge and anvil when the cartridge is coupled to the first jaw member and when the first and second jaw members are in a closed configuration. The locking member(s) are movable from a first configuration when the cartridge is not coupled to the first jaw member for engaging the knife to a second configuration when the cartridge is coupled to the first jaw member for allowing the knife to travel distally past the at least one locking member when the knife is fired.

When the cartridge is coupled to the first jaw member, the resilient member(s) may be movable from an initial configuration in which the resilient member(s) may be disposed within both the anvil and cartridge to a final configuration in which the resilient member(s) may be disposed solely within the cartridge. In the initial configuration, the knife is allowed to travel distally past the locking member(s) when the knife is fired. Moreover, in the final configuration the locking member(s) are configured to engage the knife. The surgical stapling apparatus may include a firing mechanism that is configured to translate the knife through the anvil and cartridge.

The anvil and cartridge may each include one or more recesses disposed thereon that are configured for receipt of the resilient member(s) therethrough. The recess(es) on the anvil and cartridge may be in vertical registration with one another.

The resilient member(s) may be in the form of a spring-clip. The spring clip may include a generally arcuate configuration that is defined by opposing sidewalls. One or both of the opposing sidewalls may have one or more flanges thereon configured to releasably engage a tissue contacting surface of cartridge.

The locking member(s) may include a generally elongated configuration and may include one or more cam surfaces that are disposed at a proximal end thereof. The cam surface(s) may be configured to engage a flange disposed on a top portion of the knife. In the initial configuration, the resilient member(s) causes the locking member(s) to pivot so as to prevent engagement between the cam surface(s) and the flange such that the knife is allowed to travel distally past the locking member(s) when the knife is fired.

An aspect of the present disclosure also provides a cartridge that is configured for use with a surgical stapling apparatus. The cartridge includes a housing configured to selectively couple to a first jaw member of the surgical stapling apparatus. The cartridge includes one or more recesses that are configured to receive one or more resilient members therein. The resilient member(s) may be configured for insertion through a corresponding recess disposed on an anvil of a second jaw member of the surgical stapling apparatus. Insertion of the resilient member(s) through the corresponding recess(es) disposed on the anvil results in engagement between the resilient member(s) and one or more locking members operably disposed on the anvil; this allows a knife of the surgical stapling apparatus to travel distally past the locking member(s) when the knife is fired and allows the locking member(s) to engage the knife.

The resilient member(s) may be in the form of a spring-clip. The spring clip may include a generally arcuate configuration that is defined by opposing sidewalls each having one or more flanges thereon configured to releasably engage a tissue contacting surface of cartridge.

The locking member(s) may include a generally elongated configuration and may include one or more cam surfaces that are disposed at a proximal end thereof. The cam surface(s) may be configured to engage a flange disposed on a top portion of the knife.

An aspect of the present disclosure provides a reload for use with a surgical instrument. The reload includes first and second jaw members that are pivotably coupled to each other. The first jaw member includes a channel and a sled is disposed in the channel. The sled is translatable between proximal and distal portions of the channel. An actuation member is located in the first jaw member and is movable between proximal and distal portions of the channel. A cartridge is removably coupled to the channel and includes a plurality of pushers. A lockout mechanism includes an actuation plate that is disposed in the cartridge. The actuation plate is repositionable between a first position and a second position. The actuation member is free to move between the proximal and distal portions when the actuation plate is in the first position. The actuation member is blocked from movement when the actuation plate is in the second position. A biasing member is coupled to the first jaw member and urges the actuation plate towards the second position. Distal movement of the actuation member transitions the actuation plate from the first position to the second position.

Engagement of the actuation plate and a pusher may maintain the actuation plate in the first position. The pusher may be a staple driving pusher. Distal movement of the actuation member may reposition the pusher such that the biasing member urges the actuation plate from the first position to the second position. When the actuation plate is in the first position, the actuation member is translatable from the proximal portion of the channel to the distal portion of the channel. Moreover, when the actuation plate is in the second position, the actuation member is maintained at the proximal portion of the channel.

An aspect of the present disclosure provides a reload for use with a surgical instrument. The reload includes first and second jaw members that are pivotably coupled to each other. The first jaw member includes a channel. An actuation member is located in the first jaw member and is translatable between proximal and distal portions of the channel. A cartridge is removably coupled to the channel and operably associated with the actuation member. A finger is rotatably coupled to a top surface of the cartridge, the finger rotatable between a first position and a second position. A biasing member is operatively associated with the finger. An arm is rotatably coupled to a bottom surface of the channel and is rotatable between open and closed positions in response to rotation of the finger between first and second positions. The actuation member is translatable distally through the cartridge when the arm is in the open position and is inhibited from distal translation when the arm is in the closed position.

When the actuation member advances distally through the cartridge, the actuation member engages the finger and rotates the finger from the first position to the second position, thereby rotating the arm from the closed position to the open position. The biasing member urges the finger towards the first position such that the arm is urged towards the closed position.

An aspect of the present disclosure provides a reload for use with a surgical instrument. The reload includes first and second jaw members that are pivotably coupled to each other. The first jaw member includes a channel. An actuation member is located in the first jaw member and is movable between proximal and distal portions of the channel. The cartridge is removably coupled to the channel and operably associated with the actuation member. An arm is pivotably disposed in a slot of the channel. A biasing member is operatively coupled to the arm and urges the arm out of alignment with a longitudinal axis of the channel to a position blocking the channel. When the cartridge is positioned in the channel, the arm is urged into longitudinal alignment with the channel such that the actuation member is free to move through the cartridge. Moreover, when the cartridge is removed from the channel, the arm is urged out of longitudinal alignment with the channel such that the actuation member is blocked from movement through the channel.

A bottom surface of the cartridge may include a protrusion that is engageable with the arm such that distal translation of the actuation member deforms the tab. The actuation member may be translatable proximally over the deformed tab and inhibited from distal translation over the deformed tab.

An aspect of the present disclosure provides a reload for use with a surgical instrument. The reload includes first and second jaw members that are pivotably coupled to each other and define a slot. The first jaw member includes a channel. A sled is disposed in the channel and is translatable between proximal and distal portions of the channel. An actuation member is located in the first jaw member and is movable through the slot between proximal and distal portions of the channel. A cartridge is removably coupled to the channel and includes a plurality of pushers. The pusher may be a staple driving pusher. A lockout mechanism includes a latch that is disposed in the cartridge. The latch is repositionable between a first position and a second position. The latch configured to block the slot in the second position. The latch may have a tapered surface that is engaged by the actuation member when the actuation member moves in the proximal direction.

The actuation member free to move between the proximal and distal portions when the latch is in the first position. The actuation member is blocked from movement when the actuation plate is in the second position. A biasing member urges the latch towards the second position. And, a plate holds the latch in the first position.

Engagement of the plate and a pusher maintains the plate in a first position holding the latch in the first position. The plate may have a second position that allows the latch to move to the second position to maintain the actuation member at the proximal portion of the channel. The actuation member may move in a distal direction to actuate the surgical instrument and the actuation member may move in a proximal direction after actuating the instrument.

BRIEF DESCRIPTION OF THE DRAWING

Various embodiments of the present disclosure are described hereinbelow with references to the drawings, wherein:

FIG. 5 is a perspective view of the spring clip of FIG. 4A;

FIG. 6 is a perspective view of an anvil uncoupled to a corresponding jaw member to illustrate a recess configured to receive the spring clip therein;

FIG. 7 is a perspective view of a pivot beam that is configured to releasably engage the spring clip;

FIG. 15 is an exploded, perspective view of the reload with the parts separated and removed;

FIG. 16 is an exploded, perspective view of the cartridge assembly with parts separated;

FIG. 17 is an exploded, bottom view of a sled of the cartridge with parts separated;

FIG. 18 is a bottom view of the sled of FIG. 17 in an assembled configuration;

FIG. 19 is an exploded, rear perspective view of the sled with parts separated;

FIG. 20 is a rear perspective view of the sled of FIG. 19 in an assembled configuration;

FIG. 23 is perspective view of the reload with parts removed;

FIG. 24 is an enlarged area of detail of FIG. 23;

FIG. 36 is perspective view of a reload with parts removed and including a drive lockout mechanism according to another embodiment of the present disclosure;

FIG. 37 is an enlarged area of detail of FIG. 36;

FIG. 38 is an exploded, perspective view of the reload depicted in FIG. 36;

FIG. 39 is an exploded, perspective view of a cartridge assembly with parts separated;

FIG. 48 is a perspective view of a reload with parts removed and including a drive lockout mechanism according to another embodiment of the present disclosure;

FIG. 49 is an enlarged area of detail of FIG. 48;

FIG. 60 is a perspective view of a reload with parts removed and including a drive lockout mechanism according to another embodiment of the present disclosure;

FIG. 61 is an enlarged area of detail of FIG. 60;

FIG. 67 is an enlarged area of detail of FIG. 65 illustrating an actuator of the cartridge;

FIG. 68 is an enlarged area of detail of FIG. 66 illustrating a locking assembly with parts separated;

FIG. 69 is a perspective view illustrating a spring clip and locking lever of the locking assembly coupled to one another;

FIGS. 70A-70C are perspective views illustrating the locking lever and spring clip in various configurations;

FIG. 73 is a partial, cut-away view of the cartridge illustrating the knife, actuator and locking assembly shown in a pre-fired configuration;

FIG. 74 is a partial, top elevational view of the cartridge of FIG. 73;

FIG. 75 is a partial, cut-away view of the cartridge illustrating a firing sequence of the knife with the actuator and locking assembly shown in a locked out configuration;

FIG. 76 is a partial, top elevational view of the cartridge of FIG. 75;

FIG. 77 is a perspective view of a reload with parts removed and including a drive lockout mechanism according to another embodiment of the present disclosure;

FIG. 78 is an enlarged area of detail of FIG. 77;

FIG. 79 is a top elevational view of a cartridge coupled to a jaw member of FIG. 77;

FIG. 80 is an enlarged area of detail of FIG. 79;

FIG. 82 is a right perspective view of a locking lever;

FIG. 83 is a left perspective view of the locking lever depicted in FIG. 82;

FIG. 84 is a perspective view of an actuator;

FIG. 85 is an enlarged area of detail of FIG. 81;

FIG. 96 is an exploded, perspective view of the reload with parts removed and separated;

FIG. 97 is an enlarged area of detail of FIG. 96;

FIG. 98 is a partial, cross-sectional view of jaw members of the reload with the cartridge installed;

FIG. 99 is an enlarged area of detail of FIG. 98;

FIG. 100 is a partial, cross-sectional view of the jaw members in an approximated and pre-fired configuration;

FIG. 101 is a partial, cross-sectional view of the jaw members in an approximated configuration and illustrating a knife being translated therethrough;

FIG. 105 is a perspective view of a reload with parts removed and including a drive lockout mechanism according to another embodiment of the present disclosure;

FIG. 106 is an enlarged area of detail of FIG. 105;

FIG. 119 is a side, perspective view of the actuator;

FIG. 120 is a front, perspective view of the actuation sled;

FIG. 121 is a cut-away view taken along line section 121-121 shown in FIG. 118;

FIG. 122 is a top elevational view of the cartridge and jaw member coupled to one another;

FIG. 123 is an enlarged area of detail of FIG. 122;

FIG. 124 is a partial, top cross-sectional view of the cartridge and jaw member coupled to one another with a knife in a pre-fired configuration;

FIG. 125 is a partial, top cross-sectional view of the cartridge and jaw member coupled to one another with the knife in a post-fired configuration;

FIG. 126 is a partial, top elevation view of the cartridge and jaw member coupled to one another with the locking assembly in a locked out configuration;

FIG. 127 is a cut-away view taken along line section 127-127 shown in FIG. 126;

FIG. 128 is a schematic, elevation view of a knife assembly of a reload including a drive lockout mechanism according to another embodiment of the present disclosure;

FIG. 129 is a schematic, elevation view of a knife assembly of a reload in an unlocked configuration;

FIG. 130 is a top, cross-sectional view of the cartridge illustrating the knife in a locked configuration;

Figure 134:
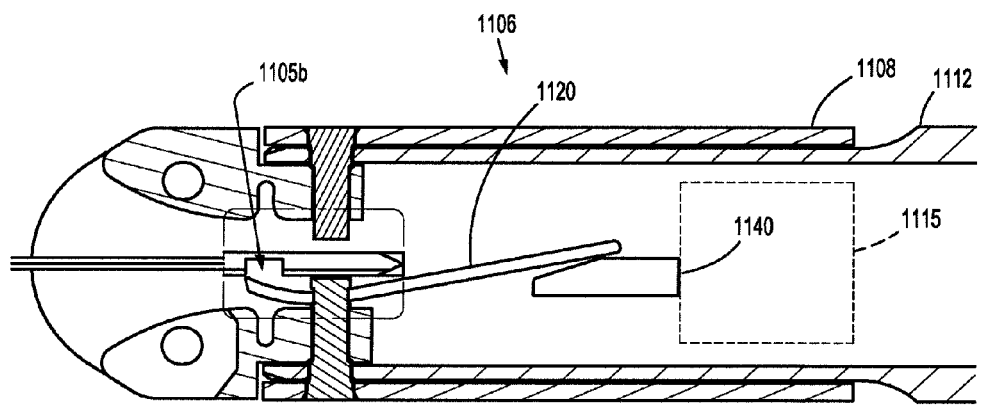
Figure 135:
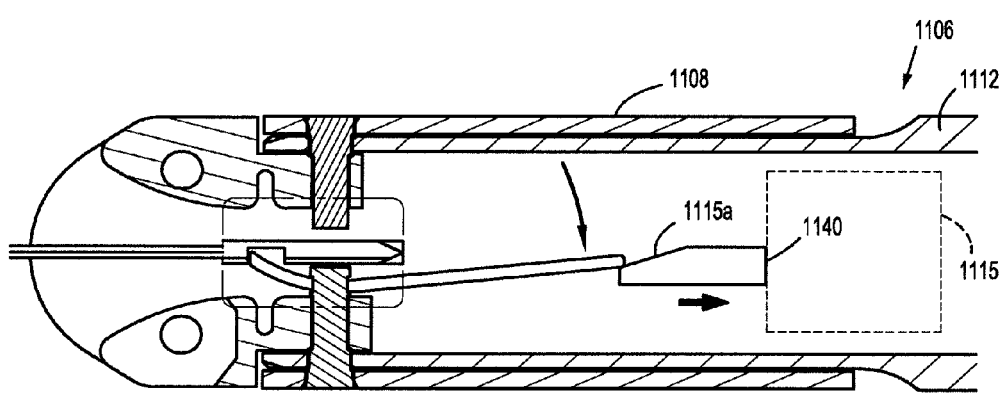
Figure 136:
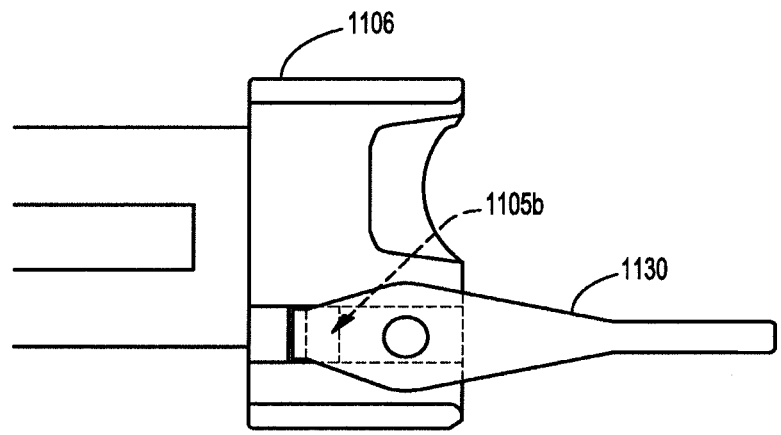
Figure 137:
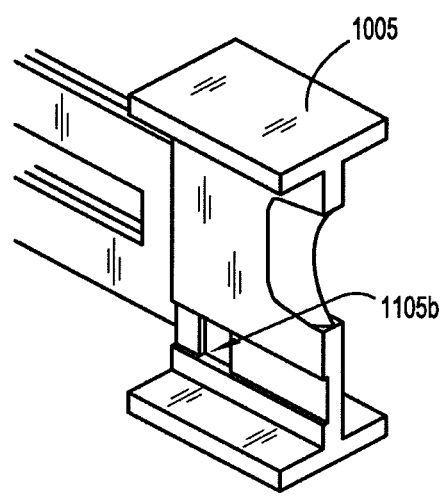
Figure 138:
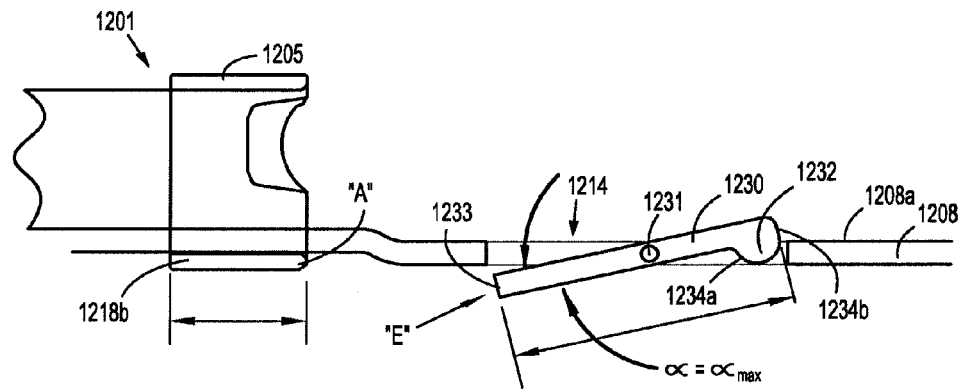
Figure 139:
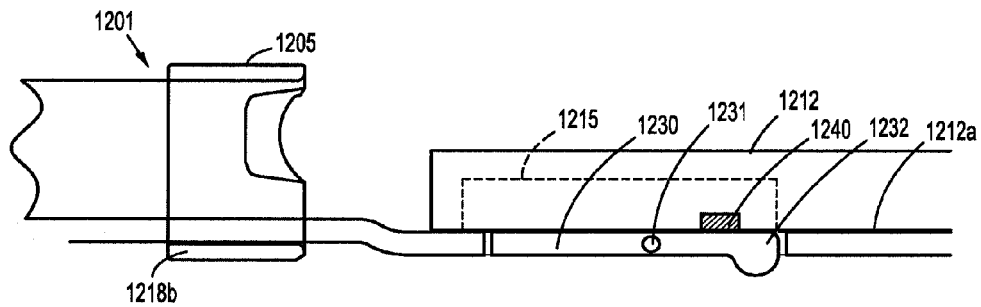
Figure 140:
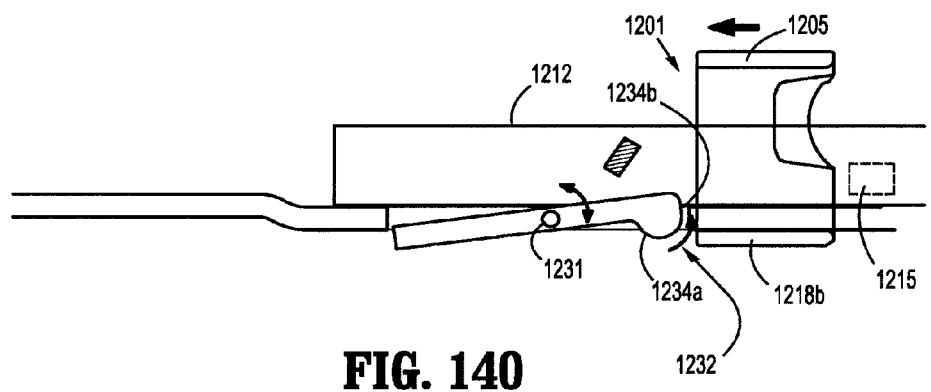
Figure 143:
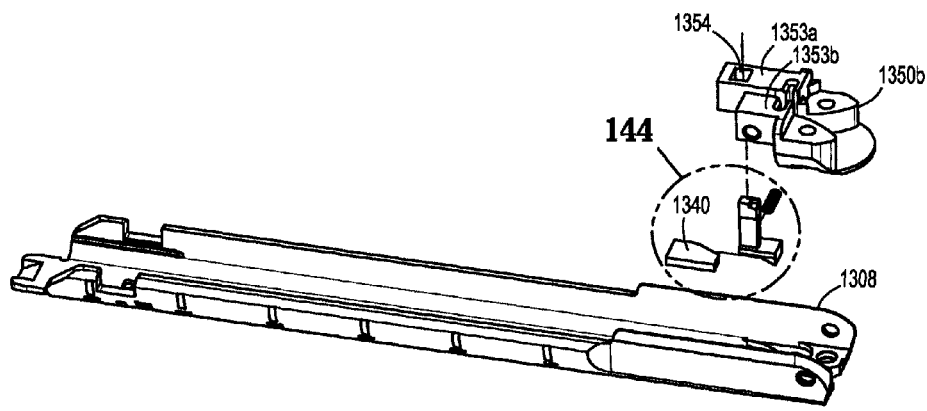
Figure 144:
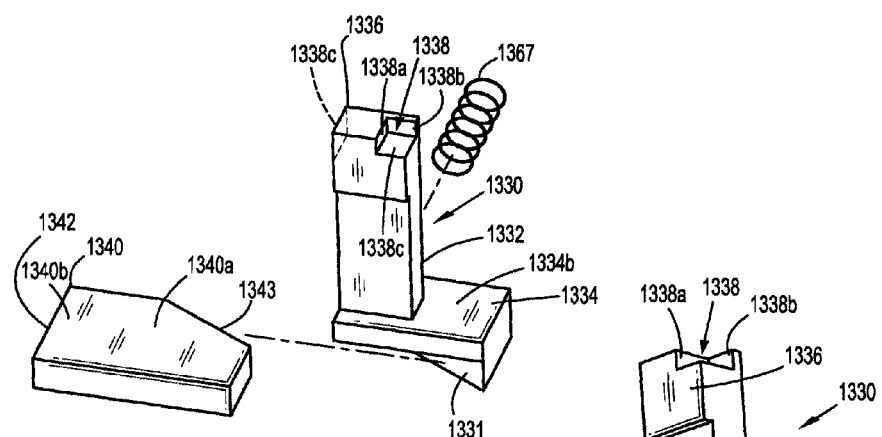
Figure 145:
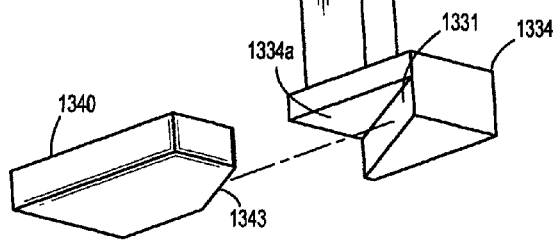
Figure 146:
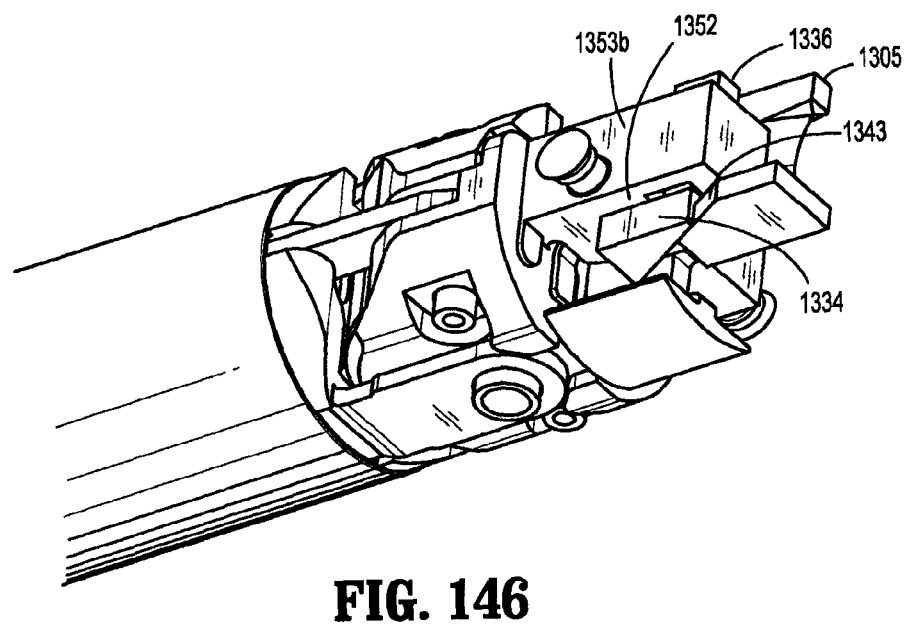
Figure 147:
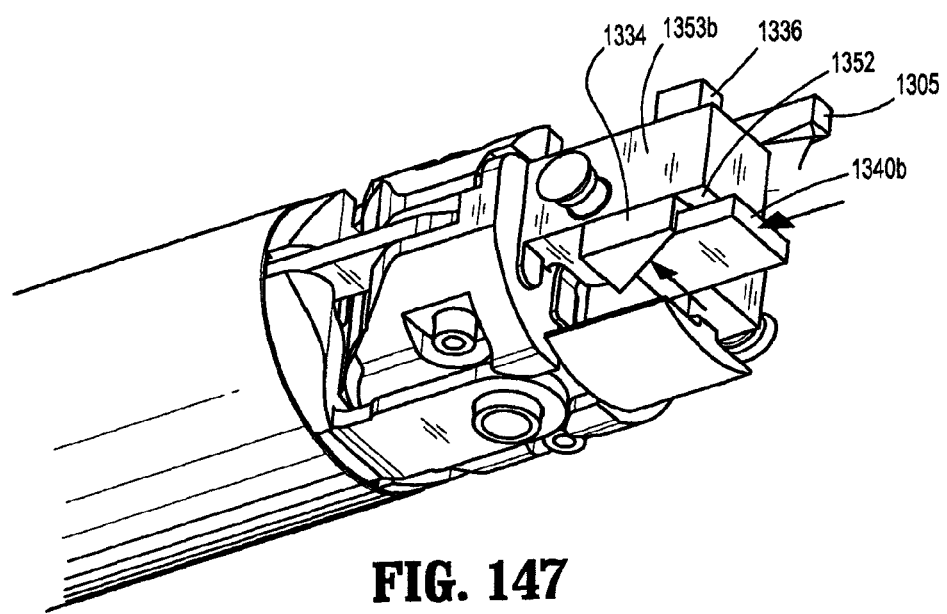
Figure 152:
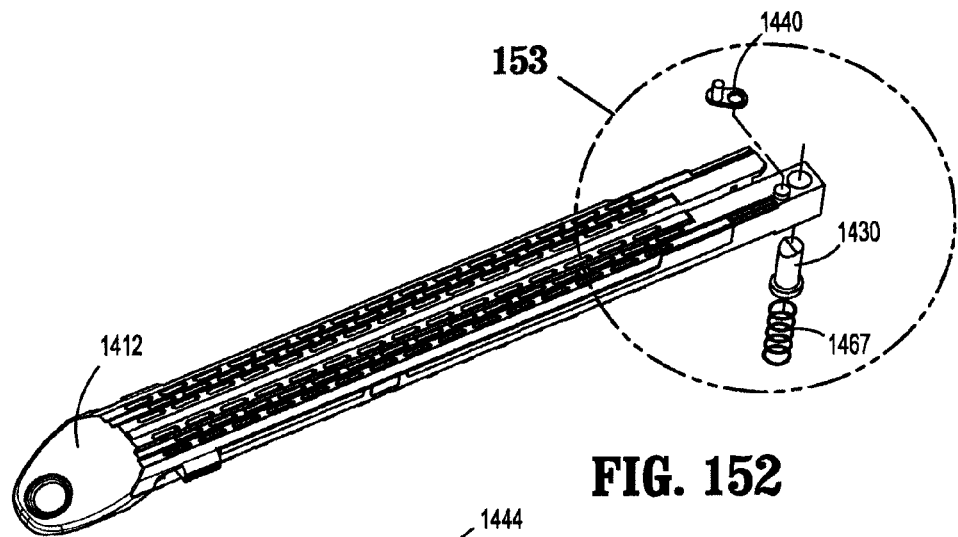
Figure 153:
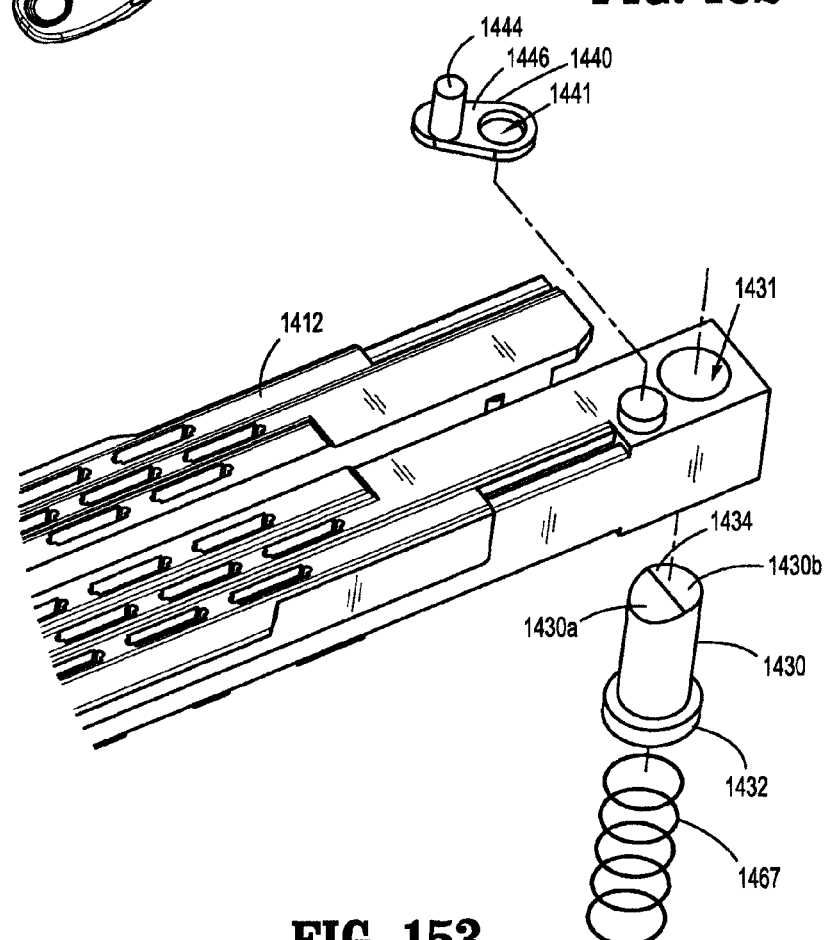
Figure 154:
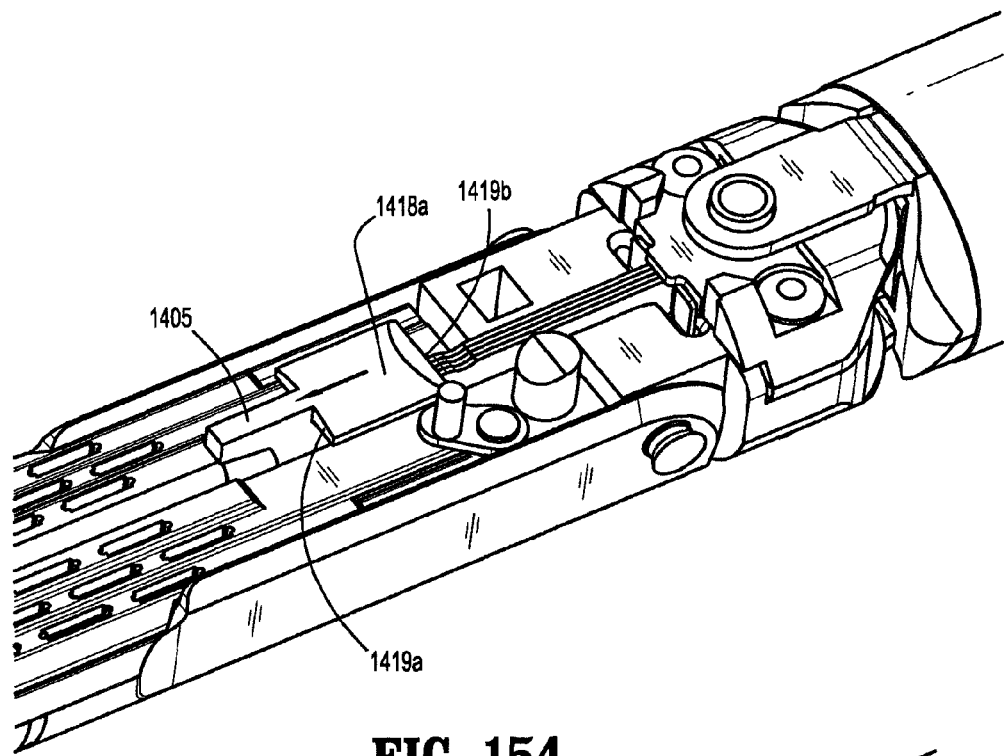
Figure 155:
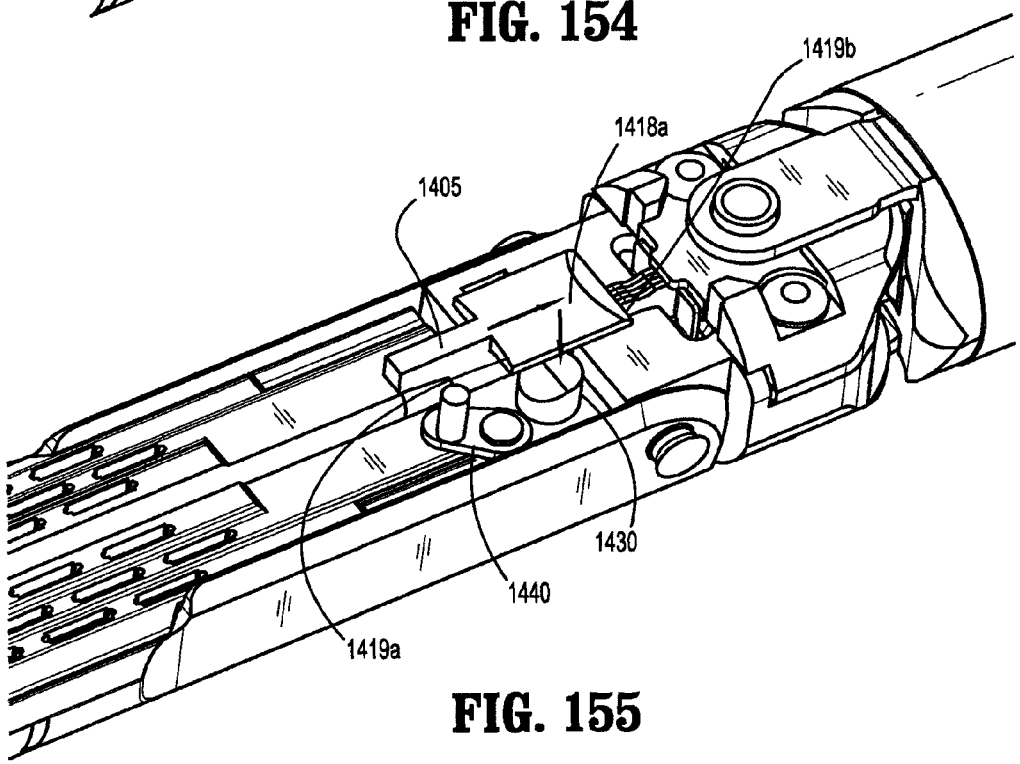
Figure 156:
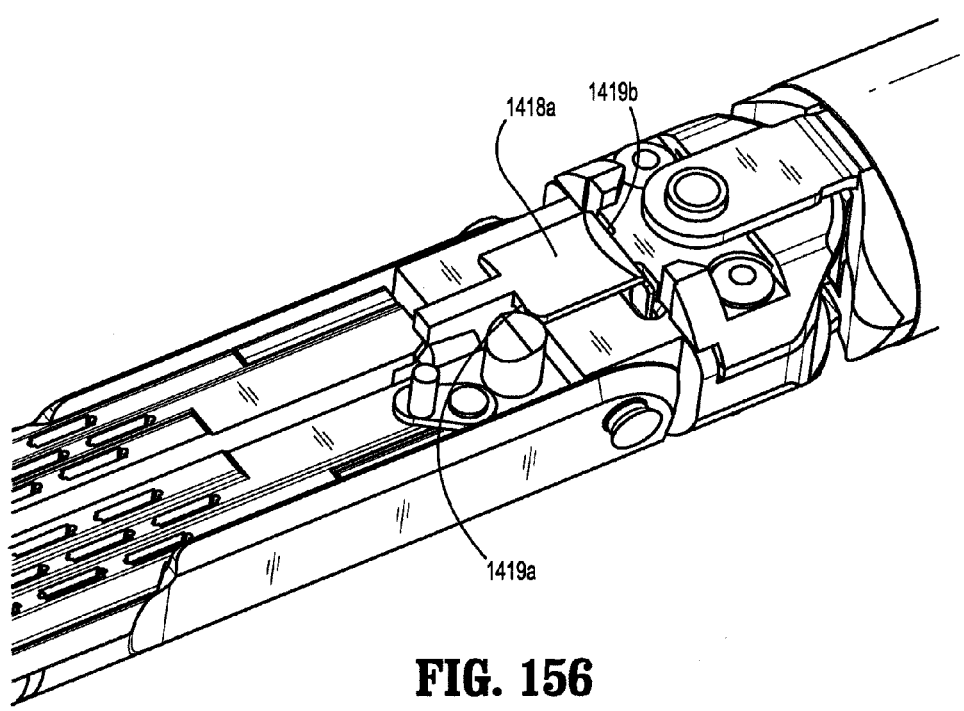
Figure 157:
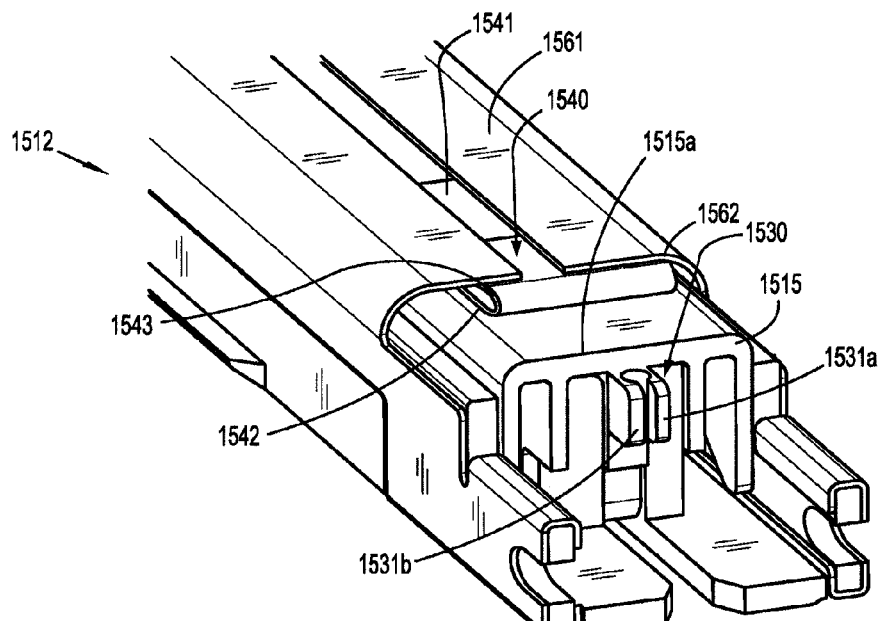
Figure 158:
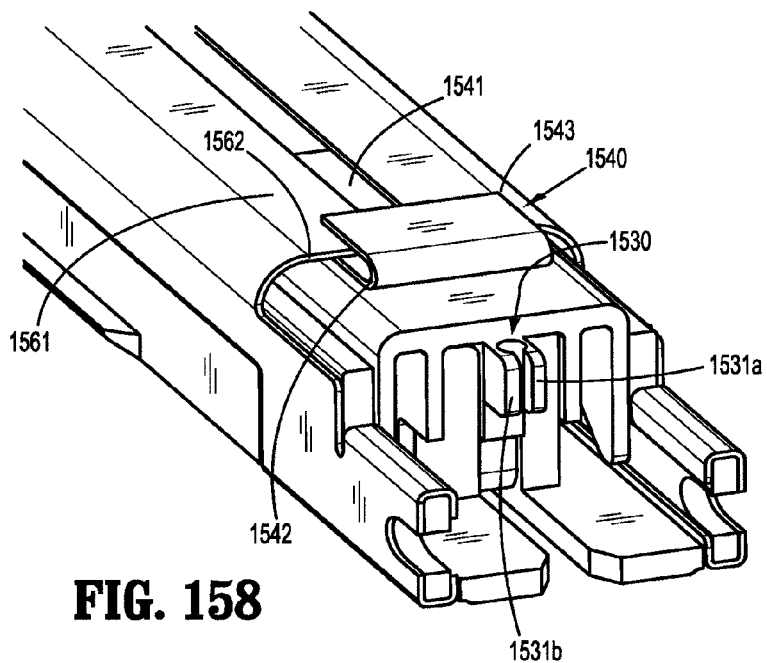

FIG. 131 is a schematic, elevation view of the knife assembly uncoupled from a locking lever;

FIG. 132 is a perspective view of the locking lever;

FIG. 133 is a perspective view of the knife assembly;

FIGS. 134-135 are top, cross-sectional views of a jaw member and cartridge of a reload including a drive lockout mechanism according to another embodiment of the present disclosure with a locking lever in unlocked and locked configurations;

FIG. 136 is a schematic, plan view of the knife assembly in a locked configuration;

FIG. 137 is a perspective view of the knife assembly;

FIG. 138 is a schematic view of a jaw member and knife of a reload including a drive lockout mechanism according to another embodiment of the present disclosure with a locking lever in a locked configuration;

FIGS. 139-140 are schematic views of the jaw member having a cartridge installed and with the locking lever in an unlocked and locked configuration, respectively;

FIG. 141 is a partial, perspective view of a reload with parts removed and including a drive lockout mechanism according to another embodiment of the present disclosure;

FIG. 142 is an enlarged area of detail of FIG. 141;

FIG. 143 is an exploded view with parts separated of a jaw member of the reload;

FIG. 144 is a perspective view of a cam block and lockout structure;

FIG. 145 is another perspective view of a cam block and lockout structure associated with the jaw member;

FIG. 146 is a partial, perspective view of the reload with parts removed illustrating the cam block and lockout structure without a cartridge installed;

FIG. 147 is a partial, perspective view of the reload with parts removed illustrating the cam block and lockout structure with a cartridge installed;

FIG. 148 is partial perspective with of the releasable reload with parts removed and with the cartridge installed;

FIG. 149 is an enlarged area of detail of FIG. 148;

FIG. 150 is a partial, perspective view of a reload with parts removed and including a drive lockout mechanism according to another embodiment of the present disclosure;

FIG. 151 is an enlarged area of detail of FIG. 150;

FIG. 152 is a perspective view of a cartridge configured for use with the reload depicted in FIG. 150;

FIG. 153 is an enlarged area of detail of FIG. 152;

FIG. 154 is a partial, perspective view of the cartridge illustrating a knife just after firing thereof;

FIG. 155 is a partial, perspective view of the cartridge illustrating with the knife being moved to a retracted configuration;

FIG. 156 is a partial, perspective view of the cartridge illustrating with the knife in the retracted configuration;

FIG. 157 is a partial, perspective view looking into a cartridge assembly configured for use with a reload including a drive lockout mechanism according to another embodiment of the present disclosure in a pre-fired configuration; and FIG. 158 is a is a partial, perspective view looking into a cartridge assembly configured for use with a reload including a drive lockout mechanism according to another embodiment of the present disclosure in a post-fired configuration.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In accordance with the instant disclosure, various drive lockout mechanisms are disclosed herein and are configured for use with reloads that are adapted to couple to one or more types of surgical stapling apparatuses. The various drive lockout mechanisms are configured to prevent misfiring of a knife without a cartridge installed, or firing with a spent cartridge installed.

Figure 1:
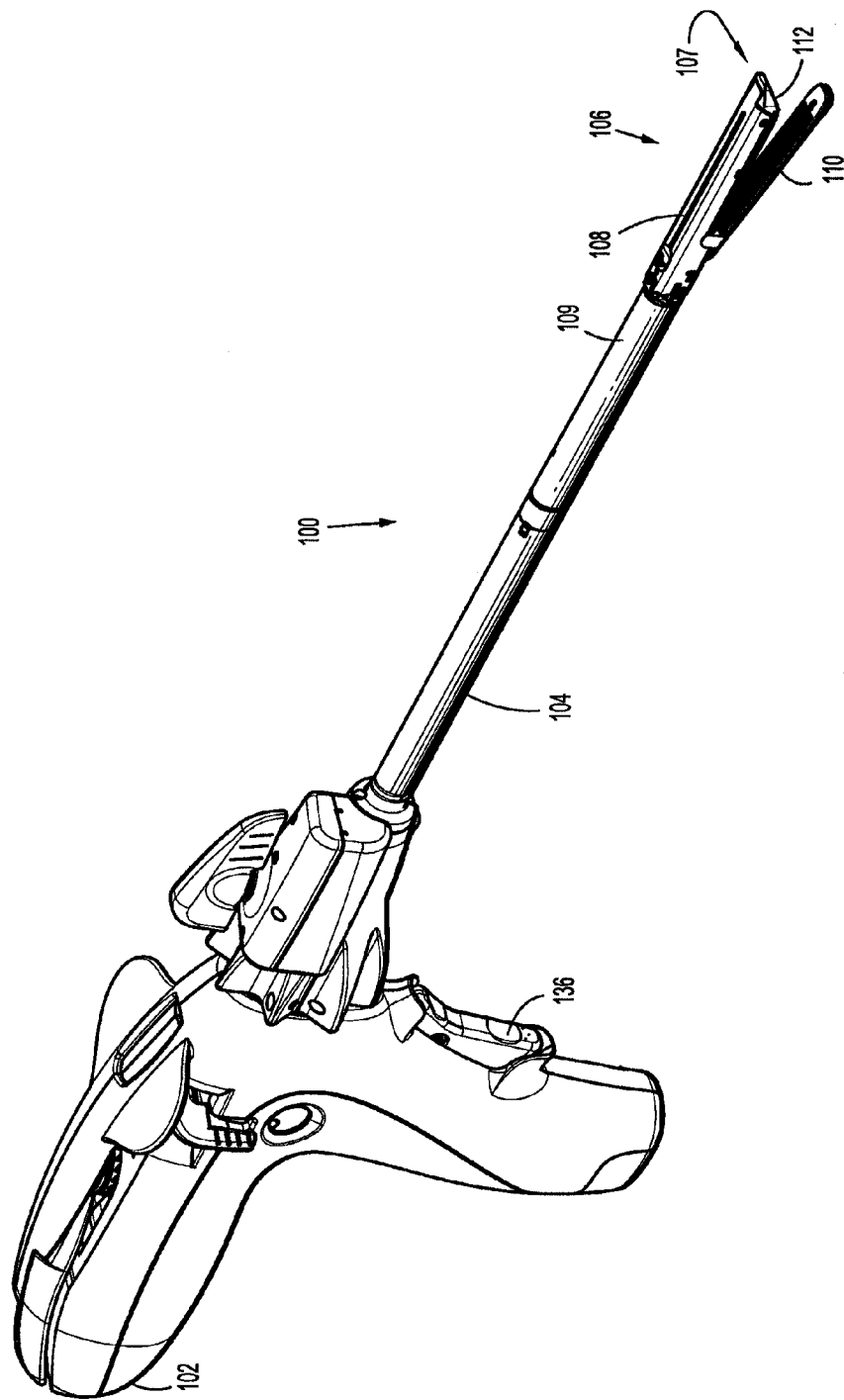
FIG. 1 is a perspective view of a powered surgical stapling apparatus.
Figure 2:
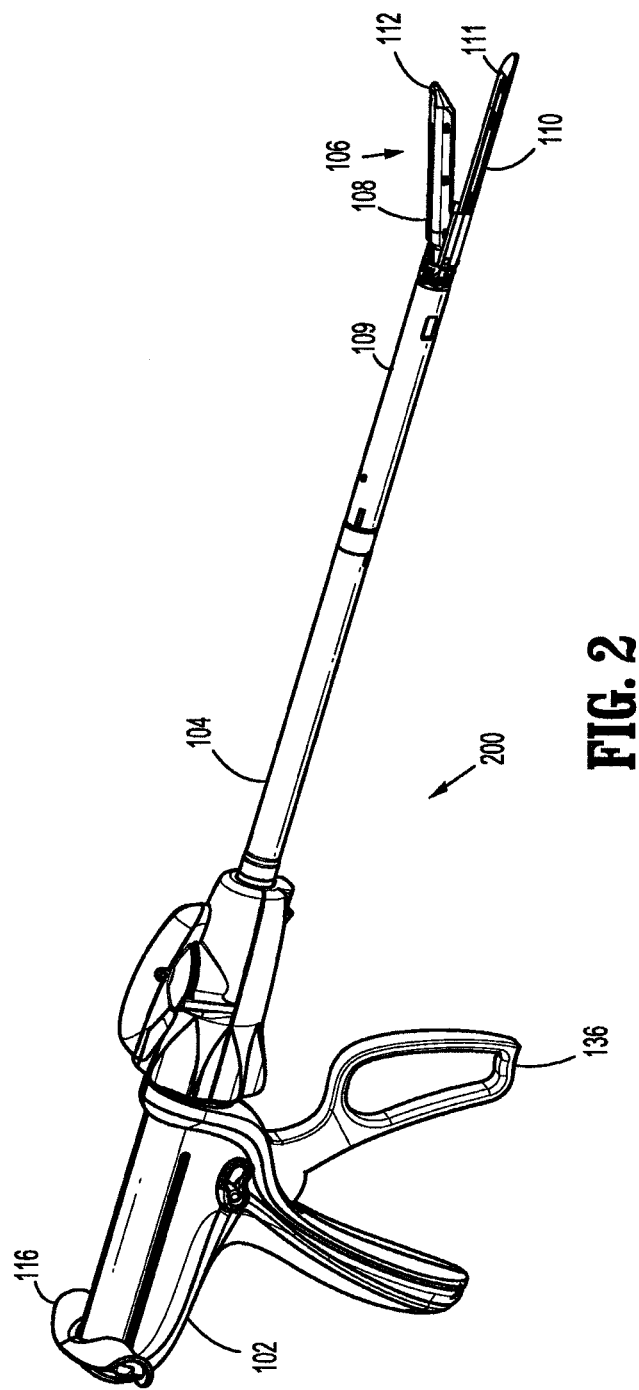
FIG. 2 is a perspective view of a manual surgical stapling apparatus.

FIG. 1 illustrates a powered surgical stapling apparatus shown generally as 100. FIG. 2 illustrates a manual surgical stapling apparatus shown generally as 200. The powered apparatus includes one or more motors and an internal or external power source, whereas the manual apparatus has a movable handle 136 and a mechanism for driving the functions of the apparatus. See U.S. Pat. Nos. 5,865,361; 5,782,396; International WO 04/032,760; U.S. Patent Publication No. 2010/0276741; and U.S. patent application Ser. No. 13/444,228, the entire contents of each of these disclosures is hereby incorporated by reference.

Figure 3A:
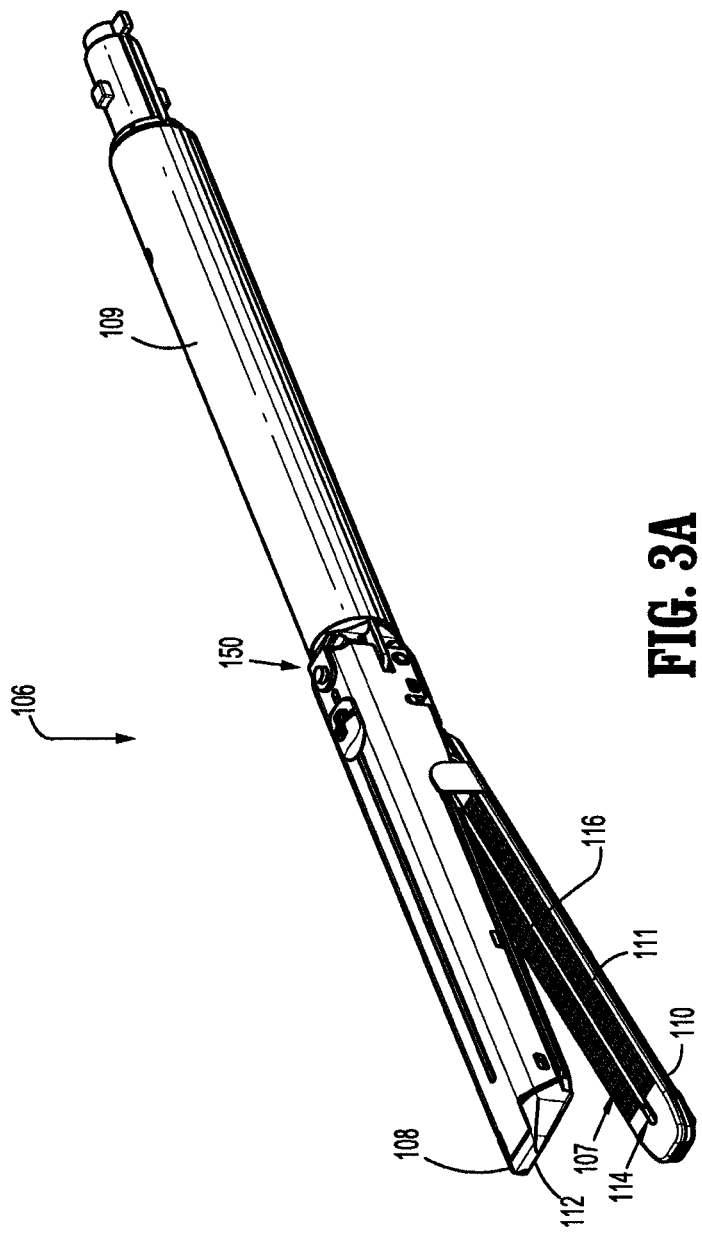
FIG. 3A is a perspective view of a reload of FIGS. 1 and 2 including a drive lockout mechanism according to an embodiment of the instant disclosure.
Figure 3B:
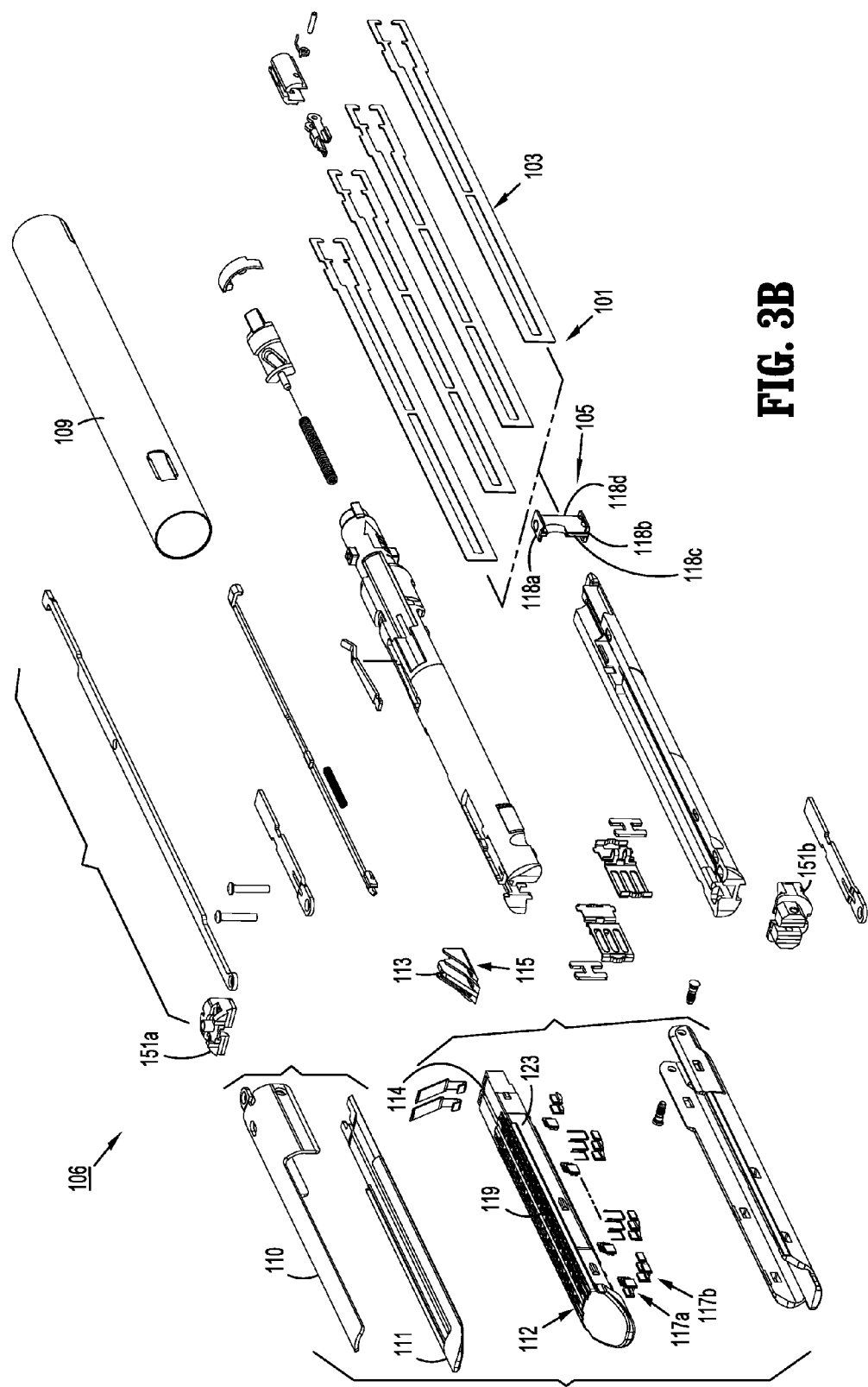
FIG. 3B is an exploded, perspective view of the reload of FIG. 3A with the parts separated.

Briefly, the surgical stapling apparatus 100, 200 includes a housing 102 a retractor 116, a firing mechanism 116 (FIG. 2), an elongated member 104 extending from housing 102, and a reload 106 that is releasably coupled to a distal end of elongated member 104. Reload 106 includes a proximal shaft portion 109 having a distal end which a tool assembly including first and second jaw members 108, 110. First jaw member 108 is configured to support a cartridge 112 which includes a plurality of fasteners 117a and a corresponding plurality of pusher members 117b that are engaged with fasteners 117a (see FIG. 3B). Cartridge 112 includes one or more retention slots 119 that extend longitudinally along a tissue contacting surface 121 of a cartridge housing 123 and are configured to house fasteners 117a (FIG. 3B). Cartridge housing 123 (FIG. 3B) is configured to releasably couple to first jaw member 108 via one or more suitable coupling methods. A removable and replaceable cartridge assembly is disclosed in U.S. patent application Ser. No. 13/280,880 entitled Multi-Use Loading Unit, the entire disclosure of which is hereby incorporated by reference herein. In any of the embodiments disclosed herein, a removable and replaceable cartridge assembly may be coupled to a jaw using detents, latches, clips and the like. Second jaw member 110 is provided with an anvil 111 (as best seen in FIG. 3B) which defines a plurality of buckets or depressions 107 (see FIG. 3A) that are configured to receive corresponding fasteners 117a when fasteners 117a are ejected from cartridge 112.

FIG. 3B illustrates components that are housed within shaft 109. A drive member includes a drive beam 103 having a working end 101 which supports a knife 105. Working end 101 includes an I-beam configuration having top and bottom flanges 118a, 118b and includes a distal abutment surface 118c which engages a central support wedge 113 of actuation sled 115 (see FIG. 3B). Working end 101 is configured to move through a knife channel 114 (FIG. 3B) defined in cartridge 112 from a retracted position to an advanced position for severing stapled tissue positioned between the jaw 108, 110. Knife blade 105 travels slightly behind actuation sled 115 during a stapling procedure such that an incision is formed in tissue after the tissue has been stapled.

A pivot assembly 150 (FIG. 3A) is provided at a distal end of shaft 109 and couples first and second jaw members 108, 110 to shaft 109. Pivot assembly 150 includes lower and top portions 151b, 151a that are operably coupled to one another and the tool assembly to facilitate articulation of the tool assembly about an axis transverse to a longitudinal axis of shaft 104 (FIG. 3B).

For a more detailed discussion of the construction and operation of reload 106, reference may be made to U.S. Pat. Nos. 5,865,361 and 7,225,963, the entire contents of which are incorporated herein by reference.

In accordance with the instant disclosure, reload 106 includes a locking mechanism according to an embodiment of the instant disclosure. Specifically, and with reference to FIGS. 4A-4B, cartridge housing 123 includes one or more recesses 125 (FIG. 4B) of suitable configuration that are configured to receive and/or operably house one or more resilient members 126 (see FIG. 5). A single recess 125 which opens onto a top surface of the cartridge 112 is shown in the illustrated embodiment. Recess 125 is configured to allow flexure of legs 128a, 128b of the resilient member 126 within the confines of recess 125.

Figure 4A:
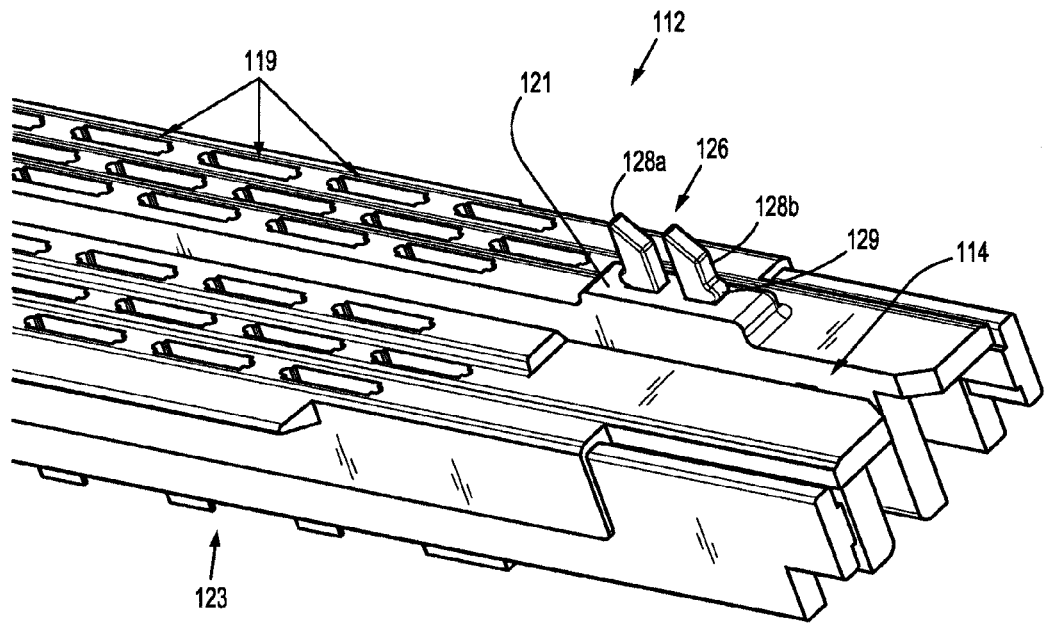
FIG. 4A is a partial, perspective view of a removable cartridge including a spring clip shown in an extended configuration.
Figure 4B:
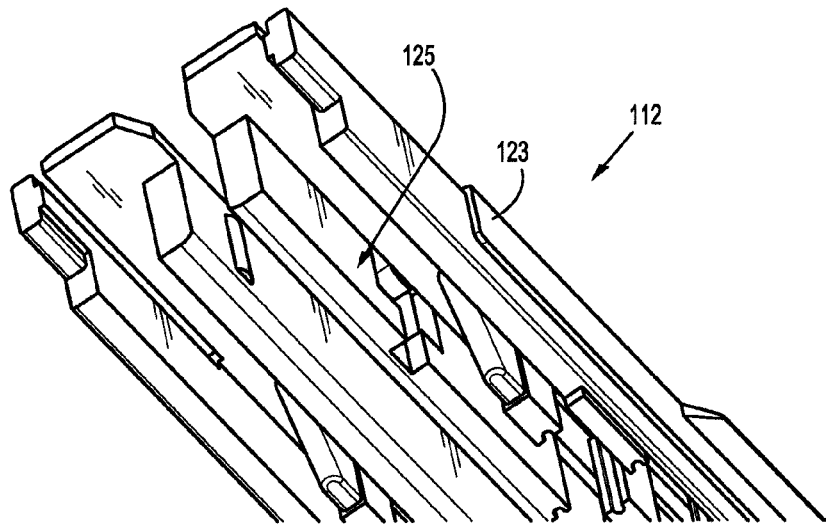
FIG. 4B is a perspective view of a proximal portion of the cartridge with the spring clip of FIG. 4A removed.
Figure 10:
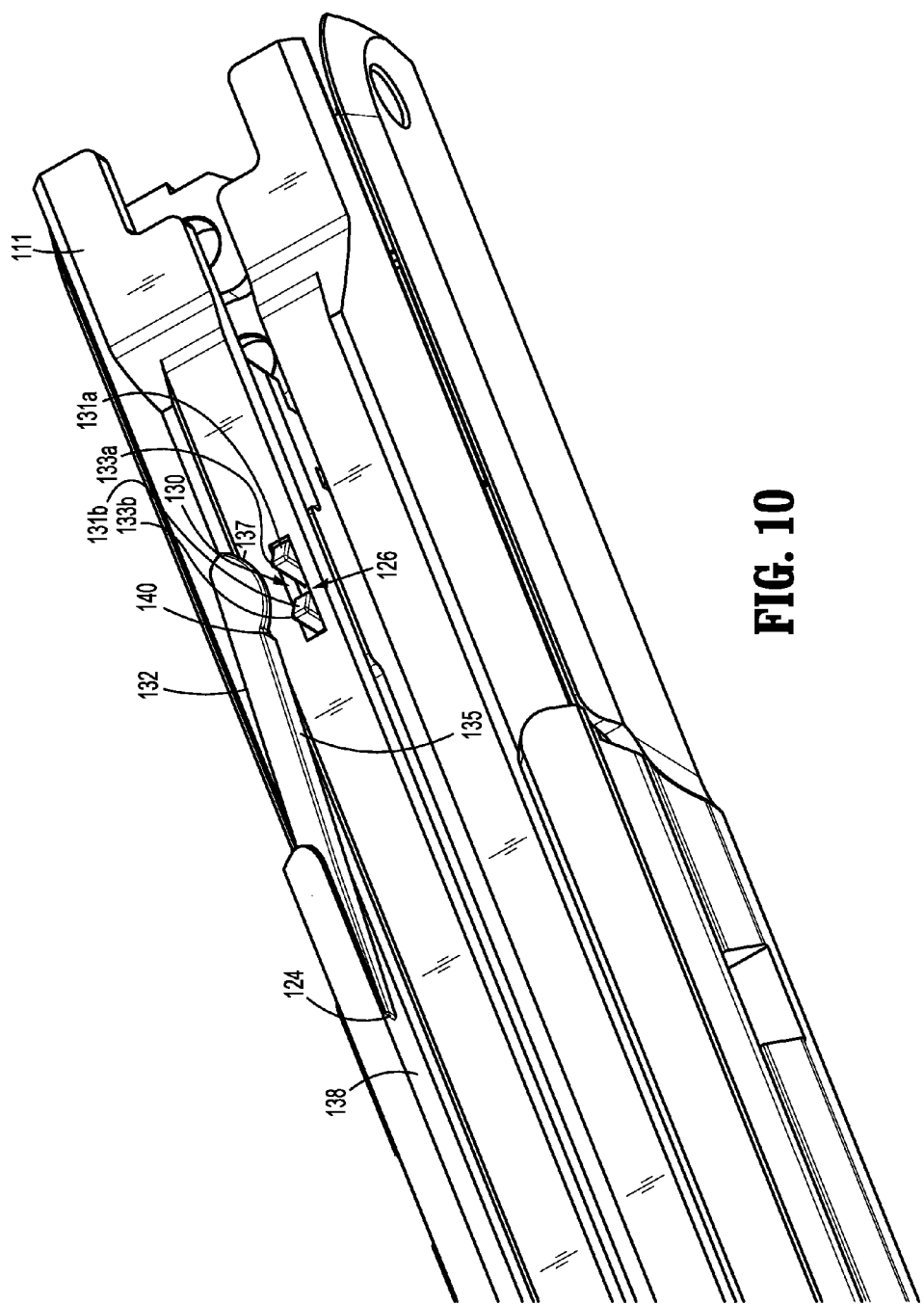
FIGS. 10-12 are perspective views illustrating a firing sequence of the knife through the cartridge and anvil.

Continuing with reference to FIG. 5, resilient member(s) 126 may be formed from any suitable resilient material including but not limited to plastic, rubber, metal, etc. In the illustrated embodiment, resilient member is made from a relatively soft plastic and formed into a spring-clip 127. Spring-clip 127 is movable from an extended position (FIG. 4a) to a retracted position (FIG. 10) and includes a generally arcuate configuration and is defined by opposing legs 128a, 128b that form a generally "U" configuration; this "U" configuration facilitates positioning spring-clip 127 within recess 125. In accordance with the instant disclosure, prior to use of cartridge 112, spring-clip 127 extends a predetermined distance above tissue contacting surface 121. To this end, one or both of legs 128a, 128b may include one or more flanges 129 (FIGS. 4A and 5) that are configured to releasably engage a surface 121 of cartridge 112 adjacent proximal end of the tissue contacting surface of cartridge 112 (FIG. 4A). In the illustrated embodiment, each of legs 128a, 128b includes a single flange 129. Moreover, one or both of legs 128a, 128b may have beveled or angled ends 131a, 131b positioned for engagement with top flange 118a of the knife 105 when knife 105 is advanced from a retracted position towards an advanced position. In the illustrated embodiment, each of sidewalls 128a, 128b includes angled surfaces 131a, 131b that culminate at tips 133a, 133b. Resilient member(s) 126 are configured for insertion through a corresponding recess 130 disposed on anvil 111 (FIGS. 6 and 10). Recess 130 on anvil 111 is in vertical registration with recess 125 of cartridge 112 to facilitate insertion of resilient member 126 within recess 130.

Referring now to FIG. 6, anvil 111 is illustrated uncoupled from jaw member 110 to illustrate recess 130. Recess 130 is of suitable configuration to receive spring-clip 126 therein. Specifically, angled end surfaces 131a, 131b are configured for positioning within recess 130 when a newly inserted (e.g., a pre-fired) cartridge 112 is coupled to jaw member 108 and jaw members 108, 110 are approximated, see FIG. 9 for example. In the extended configuration, spring clip 127 prevents movement of the locking member 132 (FIG. 7) within an internal cavity 134 (see FIG. 9 for example) of jaw member 110 to a blocking position as will be described in further detail below.

Figure 8:
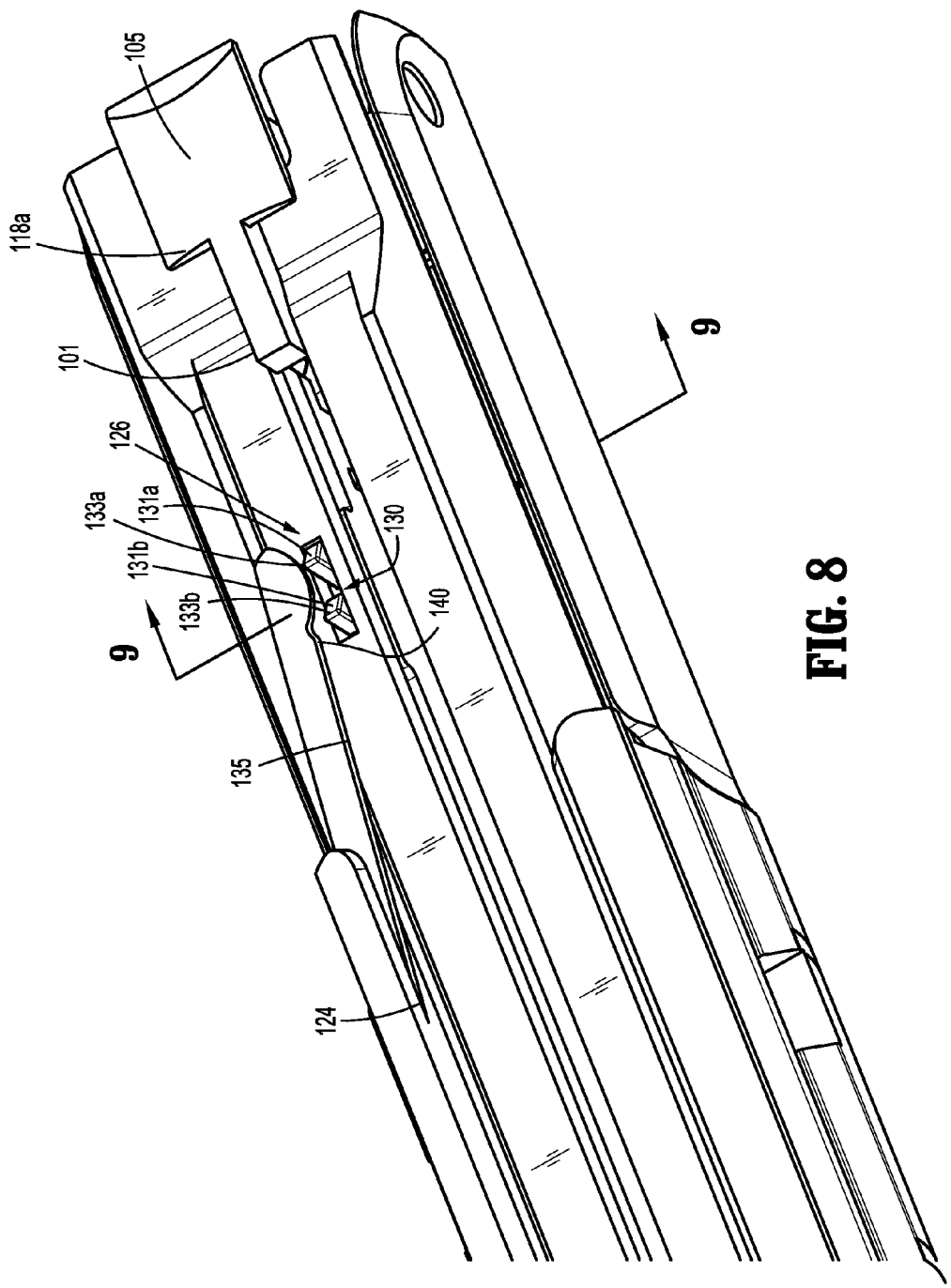
FIG. 8 is a partial, perspective view of the anvil and cartridge with a top portion of the anvil being removed to illustrate a knife in a pre-fired configuration and the spring clip and pivot beam in an engaged configuration.
Figure 11:
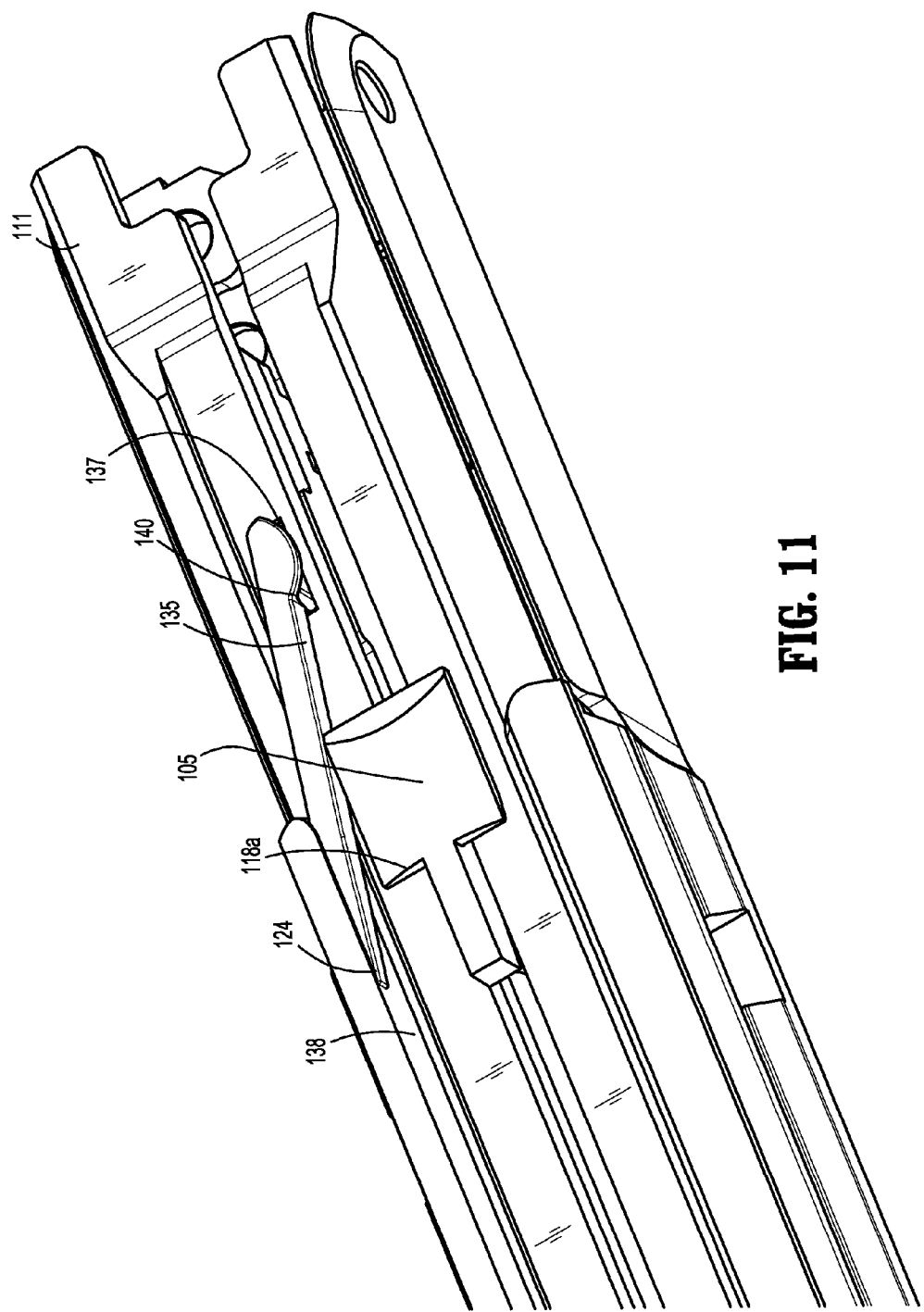
Figure 12:
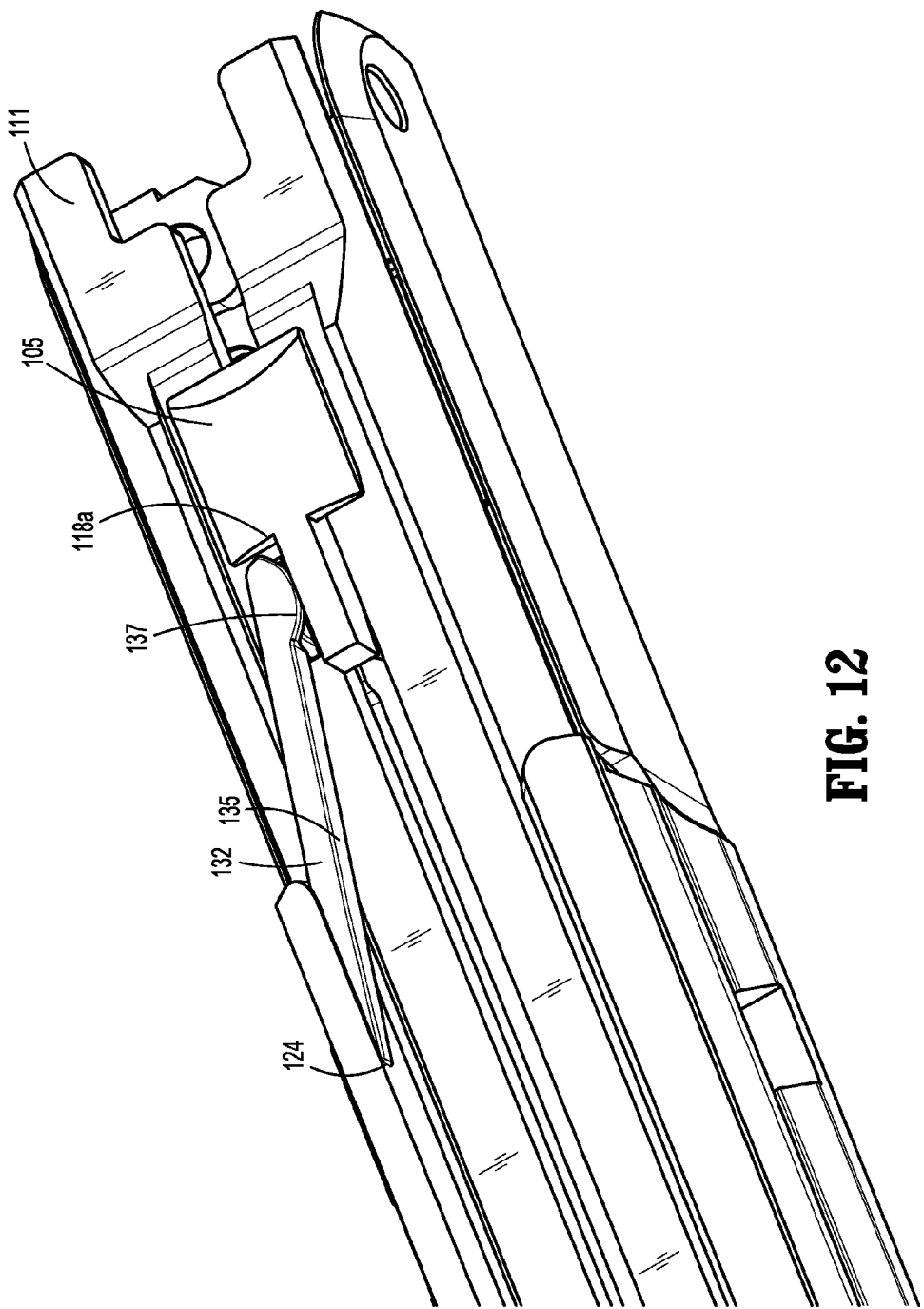

With reference to FIG. 7, locking member 132 has a generally elongated configuration and includes a distal end 124 that is operably coupled to a side wall 138 of anvil 111 to facilitate movement of the locking member 132 upwardly and transversely from an outer surface of anvil 111 towards the center of anvil 111 to a position to obstruct movement of the working end 101 of drive member (FIG. 8). A cam surface 137 is disposed at a proximal end 140 of locking member 132 and is configured to engage top flange 118a disposed on a top portion 144 of knife 105 (FIGS. 8 and 11-12). Engagement between cam surface 137 and top flange 118a prevents knife 105 from moving distally past locking member 132 after the cartridge 112 has been fired as will be described in further detail below. A sidewall 135 of locking member 132 is configured to contact a top portion 144 of knife 105 as knife 105 is moved from the advanced configuration to the retracted configuration (see FIG. 11 for example) to move the locking member 132 from the locking position (FIG. 12) to a non-blocking position to allow the knife to move from the retracted position.

In use, when cartridge 112 is not coupled to jaw member 108, locking member 132 is in the blocking position for engaging knife 105 (or component associated therewith, e.g., top flange 118a). That is, cam surface 13 7 is flush with the plane of translation of knife 105 such that an end of locking member 132 engages top flange 118a to prevent knife 105 from traveling distally past locking member 132 (see FIG. 12). Thus, the locking member 132 prevents firing of apparatus 100, 200 when a cartridge 112 has not been inserted into jaw 108.

Figure 9:
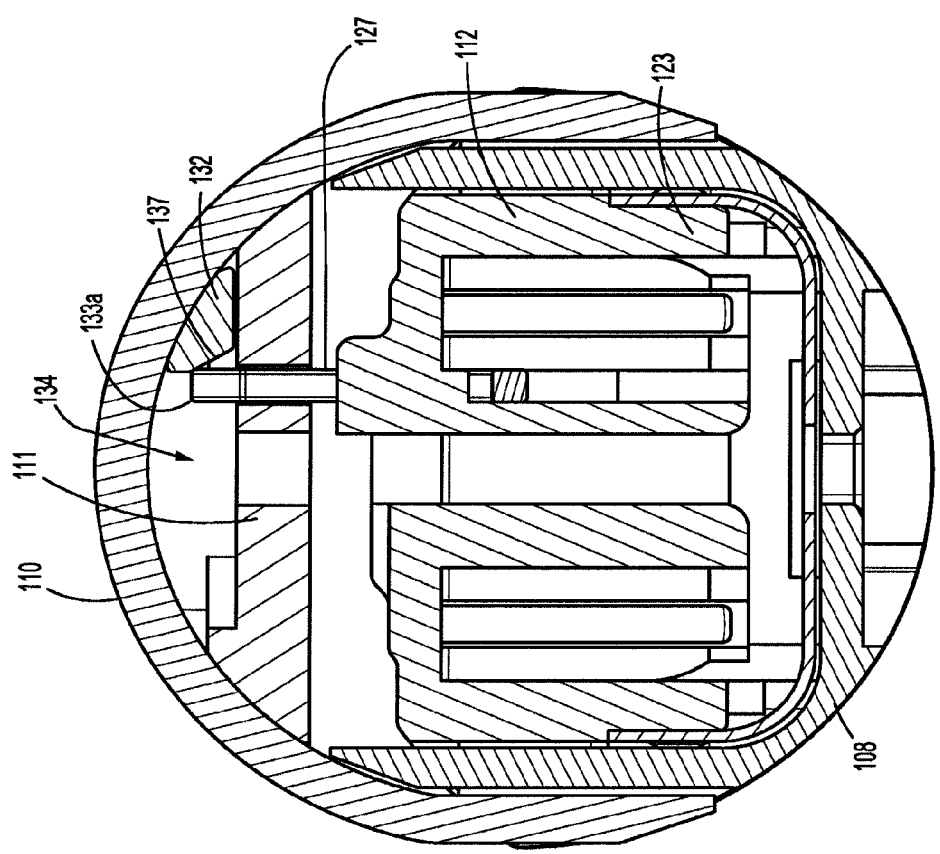
FIG. 9 is a cut-away view taken along line-segment 9-9 in FIG. 8.

When cartridge 112 is coupled to jaw member 108, locking member 132 pivots upwardly as a result of contact with resilient member 126 (see FIGS. 8-9). This contact allows working end 101 of the drive member to travel distally past the locking member 132 when knife 105 is fired (FIG. 10). Specifically, this contact raises the cam surface 137 off the plane of translation of working end 101 and above top flange 118a, which, in turn, prevents engagement therebetween so as to allow knife 105 to travel distally past locking member 132 when working end 101 is advanced.

Essentially, top flange 118a slides beneath cam surface(s) 137 as knife 105 is translated distally.

Contact between top flange 118a and tips 133a, 133b and/or angled surfaces 131a, 131b as the working end 101 is advanced causes flanges 129 to disengage from tissue contacting surface 121 of cartridge 112, which, in turn, causes tips 133a, 133b and/or angled surfaces 131a, 131b to fall beneath the translation plane of working end 101 (FIG. 10). This allows locking member 132 to return to its initial configuration (FIG. 11) obstructing distal movement of the working end 101.

As working end 101 is moved proximally back to its retracted configuration, top portion 144 contacts a sidewall 135 (FIG. 8) of locking member 132 to pivot locking member 132 sideways towards sidewall 138 of anvil 111. Once top portion 144 has been moved proximally past cam surface(s) 137 of locking member 132, locking member 132 again returns to its initial configuration. In its initial configuration, cam surface 137 is flush with the plane of translation of working end 101 and positioned to engage top portion 144 of working end 101 (FIG. 12).

The unique configuration of locking member 132 and resilient member 126 overcomes the aforementioned drawbacks that are, typically, associated with conventional surgical stapling apparatus. Specifically, the locking member 132 prevents firing of the stapling apparatus 100, 200 when a cartridge 112 is not coupled to jaw 108 or when cartridge 112 has already been fired.

From the foregoing and with reference to the various figure drawings, those skilled in the art will appreciate that certain modifications can also be made to the present disclosure without departing from the scope of the same. For example, while the surgical stapling apparatuses 100, 200 have been described herein as including one locking member 132 and one corresponding resilient member 126, it is within the purview of the present disclosure to utilize two or more locking members 132 and corresponding resilient members 126.

Additionally, while surgical stapling apparatuses 100, 200 have been described herein utilizing a reload 106 the drive lockout mechanism described above can be supported on the tool assembly of any stapler having a replaceable cartridge.

In addition, reloads that include other types of locking mechanisms may also be utilized with surgical stapling apparatuses 100, 200. The following reloads are similar in concept and design to reload 106. Accordingly, only those features unique to the hereinafter described embodiments of reloads are described in detail.

Figure 13:
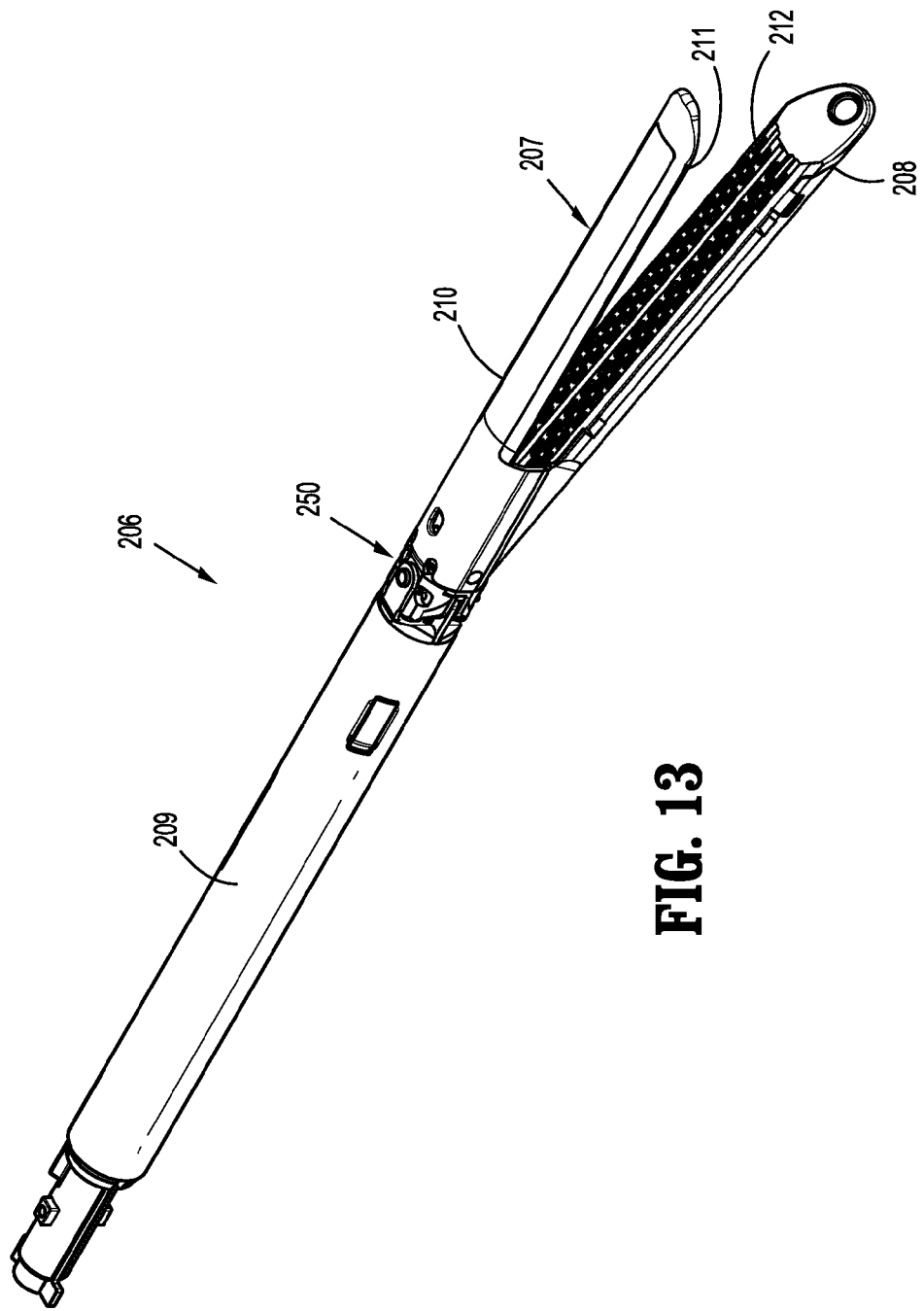
FIG. 13 is a perspective view of a reload including a drive lockout mechanism according to an alternate embodiment of the present disclosure.
Figure 14:
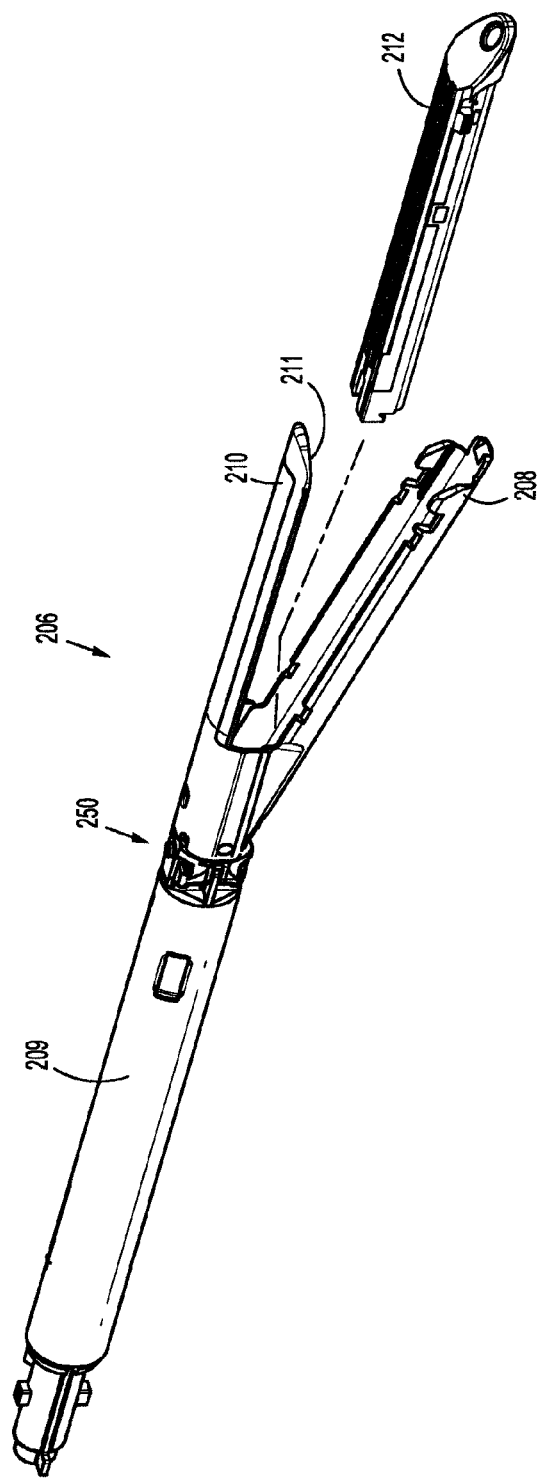
FIG. 14 is a perspective view of the reload and a cartridge depicted in FIG. 13 uncoupled from one another.

With reference to FIGS. 13-35, and initially with reference to FIGS. 13-14, a reload 206 includes a locking mechanism according to another embodiment of the instant disclosure and is configured for use with surgical stapling apparatuses 100, 200 (FIGS. 1 and 2).

Reload 206 is generally as described above but the configuration of the locking mechanism has changed as described below. Reload 206 includes shaft 209 that supports a tool assembly 207 including jaw members 208, 210, respectively. Jaw member 208 is configured to releasably engage a cartridge 212 and jaw member 210 is provided with an anvil 211. Jaw members 208, 210 function in a manner as described above with respect to jaw members 108, 110.

Figure 25:
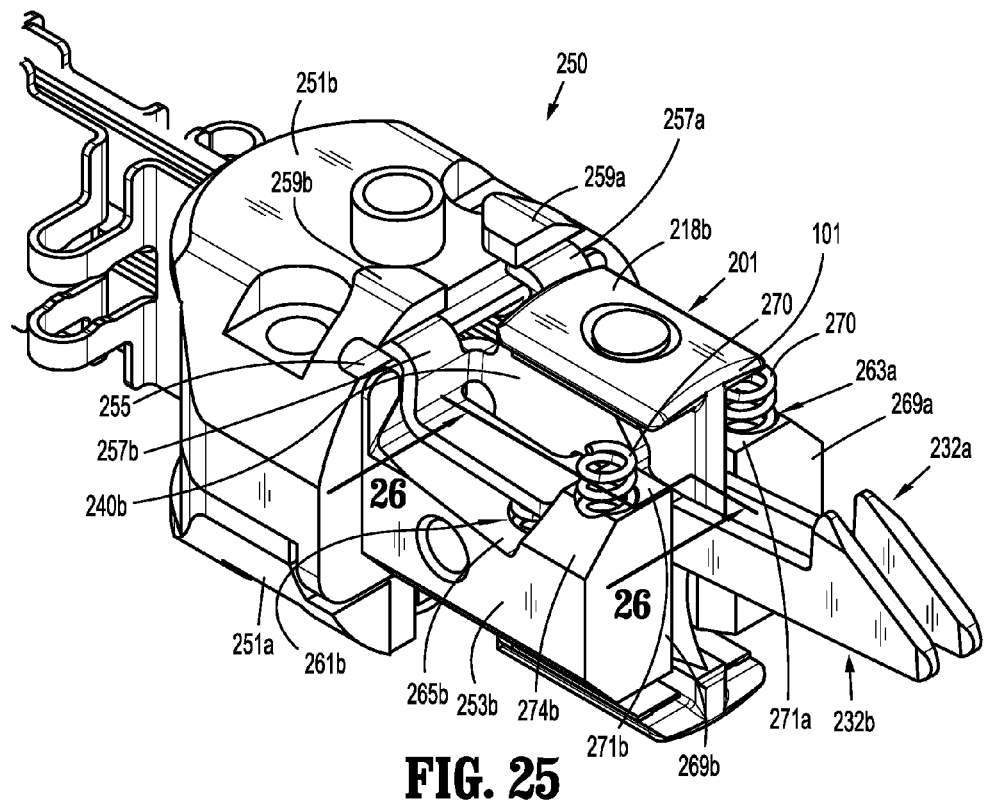
FIG. 25 is a partial, perspective view of the reload with parts removed illustrating a pivot assembly.

A pivot assembly 250 is configured to function in a manner as described above with respect to pivot assembly 150 and includes top and lower portions 251a, 251b (see FIG. 15 for example). Unlike lower portion 151b, however, lower portion 251b is configured to operably support a pair of latches 232a, 232b that are operable to lock a working end 101 of a drive member in a retracted configuration. Specifically, lower portion 251b includes a pair of distally extending leg members 253a, 253b (FIGS. 15 and 25). Leg members 253a, 253b are spaced-apart a predetermined distance from one another to receive knife 205 (FIG. 15) so as to allow working end 101 to move through a firing sequence of surgical stapling apparatuses 100, 200, as will be described in greater detail below.

Figure 26:
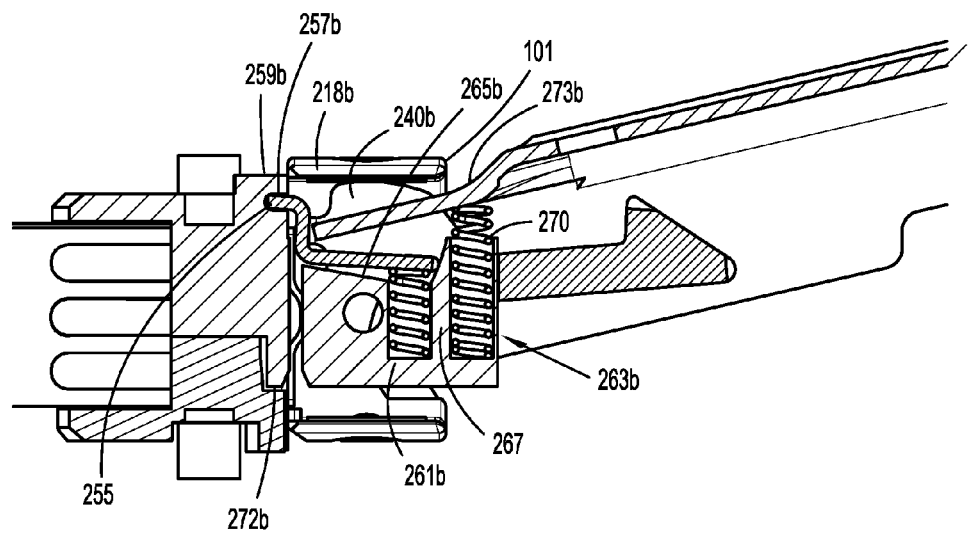
FIG. 26 is a cross-sectional view taken along line portion 26 in FIG. 25.

A shelf 255 (FIGS. 24-25) of suitable configuration is provided on lower portion 251b and is positioned proximally with respect to latches 232a, 232b. Shelf 255 extends across lower portion 251b and is configured to support finger portions 257a, 257b of latches 232a, 232b, respectively. A pair of spaced-apart holders 259a, 259b are provided on lower portion 251b and are positioned adjacent shelf 255. Holders 259a, 259b extend distally from lower portion 251b such that a distal face of holders 259a, 259b aligns with a distal edge of shelf 255 (FIG. 26). Holders 259a, 259b are configured to engage finger portions 257a, 257b to maintain direct contact between finger portions 257a, 257b and shelf 255. In embodiments, holders 259a, 259b may be replaced with a single holder that extends along an entire length of the shelf 255.

Continuing with reference to FIG. 25, leg member 253b includes a generally flat medial portion 265b (FIGS. 15 and 25) that defines a cavity 261b of suitable configuration defined therein that is configured to house a spring 267, e.g., a compression spring, (FIG. 26). Medial portion 265b is angled in a direction towards a toe portion 269b of leg member 253b. Toe portion 269b extends distally from medial portion 265b and includes a generally flat top surface 271b (FIG. 25) that is elevated a predetermined distance above medial portion 265b. Top portion 271b is configured to contact an offset flange portion 273b (FIG. 24) of cartridge 212. A proximal face 272b (FIG. 26) of toe portion 269b is angled toward medial portion 265b and a sidewall 274b is angled in an outward direction (FIG. 25) away from top surface 271b. A cavity 263b of suitable configuration is defined in toe portion 269b and is configured to house an optional spring 270, e.g., a compression spring, (FIG. 26). Spring 270 may be configured to bias cartridge 212 to the open position.

A second toe portion 269a extends distally from a medial portion (not explicitly shown) of leg member 253a and defines a cavity 263a that is configured to house spring 270 (FIG. 25). Toe portion 269a includes a generally flat top surface 271a (FIG. 25) that contacts a corresponding offset flange portion 273a (FIG. 24) of cartridge 212. The medial portion of leg member 253a includes a cavity (not explicitly shown) that is configured to house a spring 270.

Figure 30:
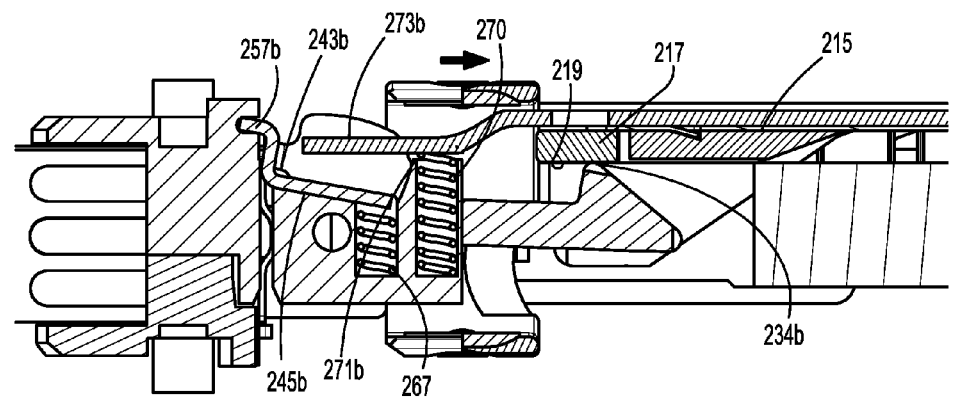
FIG. 30 is a partial, cross-sectional view of the cartridge illustrating the anvil and cartridge being in a fully approximated configuration.
Figure 31:
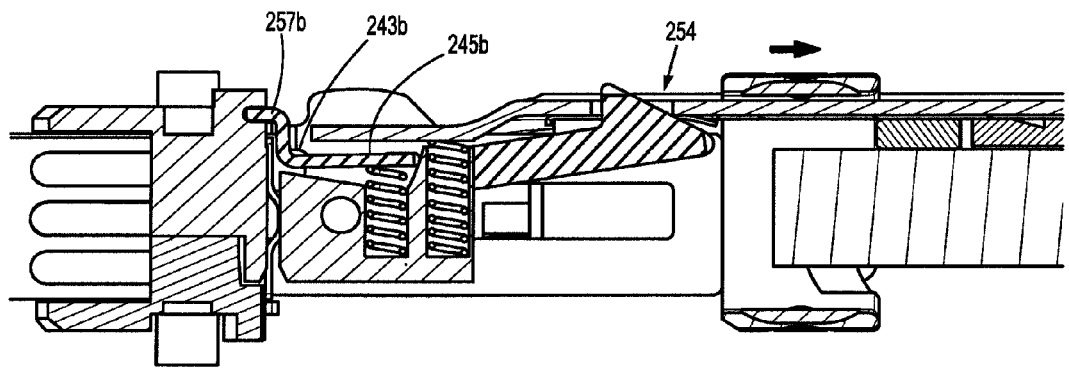
FIG. 31 is a partial, cross-sectional view of the cartridge illustrating a firing motion of a knife of the reload.

Referring to FIGS. 16-19, actuation sled 215 is similar to actuation sled 115 and includes a central support 213. Unlike actuation sled 115, however, actuation sled 215 includes a blocking member 217. Blocking member 217 may be monolithically formed with actuation sled 215 or blocking member 217 may be a separate component that is coupled to actuation sled 215 via one or more suitable coupling methods, e.g., press-fit, friction-fit, adhesive, etc. In the illustrated embodiment, actuation sled 215 and blocking member 217 are formed as separate components via an injection molding process and, subsequently, coupled to one another via a press-fit. Blocking member 217 includes a generally curvilinear base portion 219 that complements a corresponding recess 221 provided on a bottom portion of actuation sled 215. A detent 223 is provided on base portion 219 of actuation sled 215 and abuts a bottom surface 225 of central wedge 213 when actuation sled 215 is in an assembled configuration (FIGS. 18 and 20). Blocking member 217 is configured to contact a pair of distal protuberances 234a, 234b (FIGS. 21-22) of latches 232a, 232b when a loaded cartridge 212 is coupled to jaw member 208 (FIG. 30). In further embodiments, one or more latches may be used.

Figure 21:
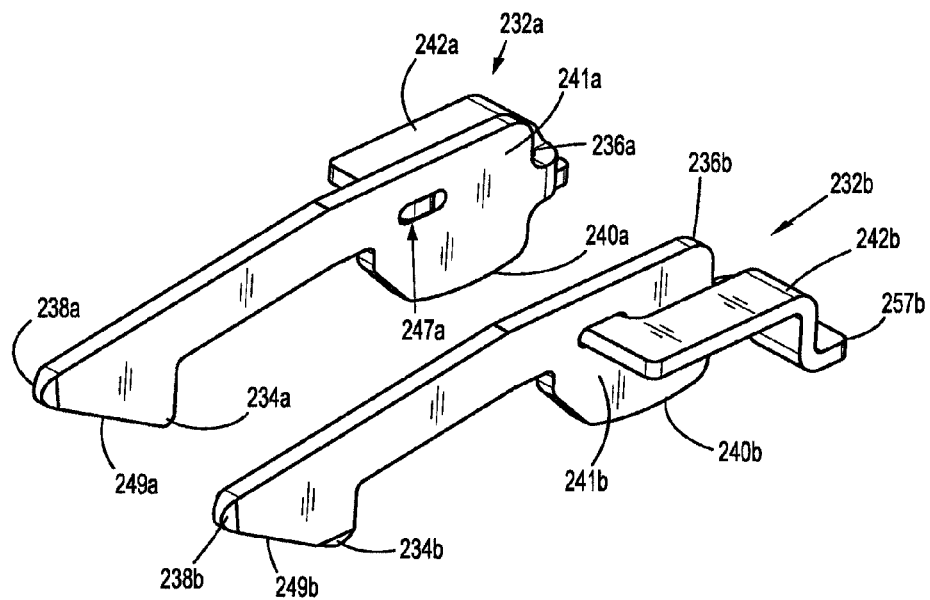
FIG. 21 is an enlarged area of detail of FIG. 15 illustrating a latch.
Figure 22:
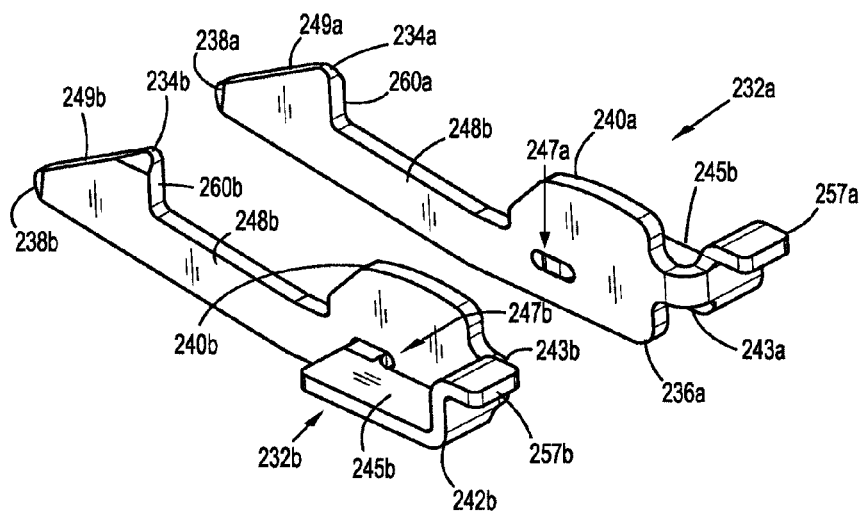
FIG. 22 is a perspective view of the latch depicted in FIG. 21 shown inverted.

Referring now to FIGS. 21-22, latches 232a, 232b may be formed via any suitable process and include proximal ends 236a, 236b and distal ends 238a, 238b, respectively. Body portions 240a, 240b are provided at respective proximal ends 236a, 236b and are configured to contact flange 218b when knife 205 is in a retracted configuration (FIGS. 26-29 and 33-34). This contact between flange 218b and body portions 240a, 240b maintains latches 232a, 232b in an unlatched configuration.

Figure 28:
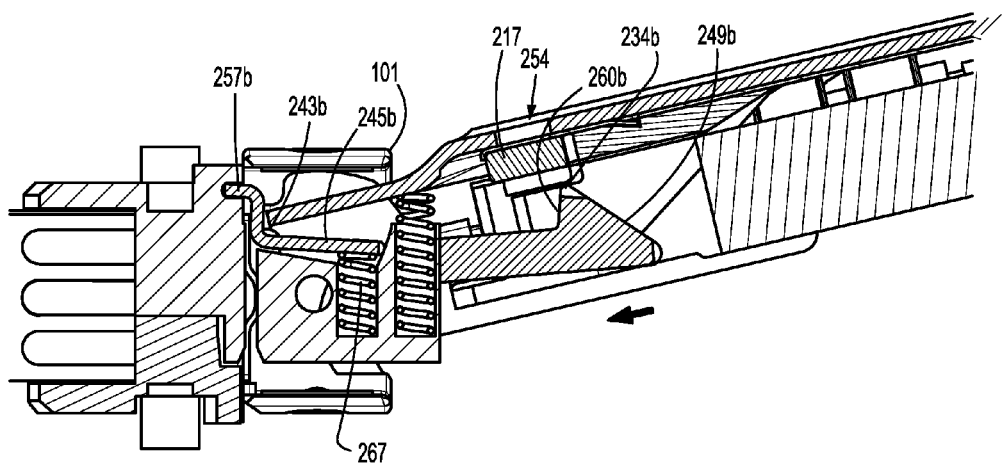
FIG. 28 is a partial, cross-sectional view of the cartridge illustrating the cartridge fully installed to the corresponding jaw member.

Lateral extensions 242a, 242b of latches 232a, 232b include generally arcuate shoulder portions 243a, 243b that extend from proximal ends 236a, 236b and have respective arms 245a, 245b that abut sidewalls 241a, 241b of body portions 240a, 240b. Distal ends of arms 245a, 245b are received within corresponding apertures 247a, 247b (FIGS. 21-22) defined in lateral extensions 242a, 242b. Finger portions 257a, 257b extend in a generally orthogonal direction from shoulder portions 243a, 243b and proximally toward shelf 255 for engagement with corresponding holders 259a, 259b. Arms 245a, 245b are configured to engage springs 267 provided on leg members 253a, 253b to bias latches 232a, 232b in a downwardly direction (FIG. 28).

Figure 32:
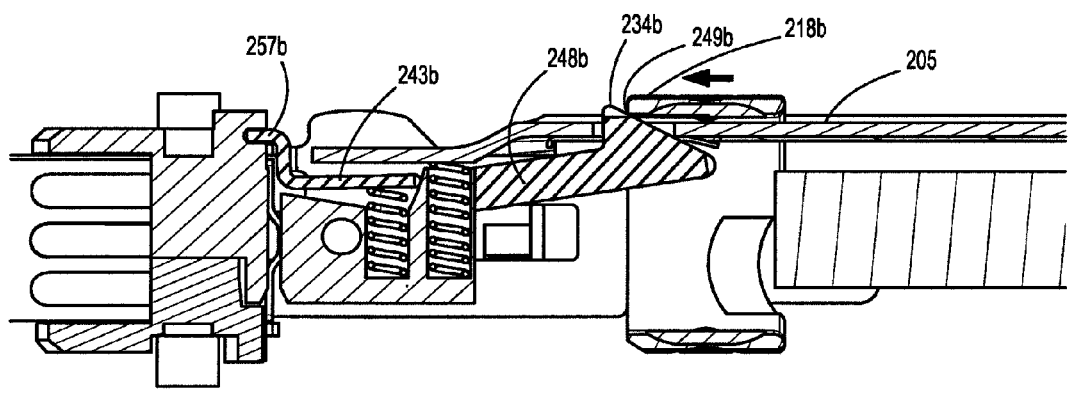
FIG. 32 is a partial, cross-sectional view of cartridge illustrating the knife being retracted back to a pre-fired configuration.
Figure 35:
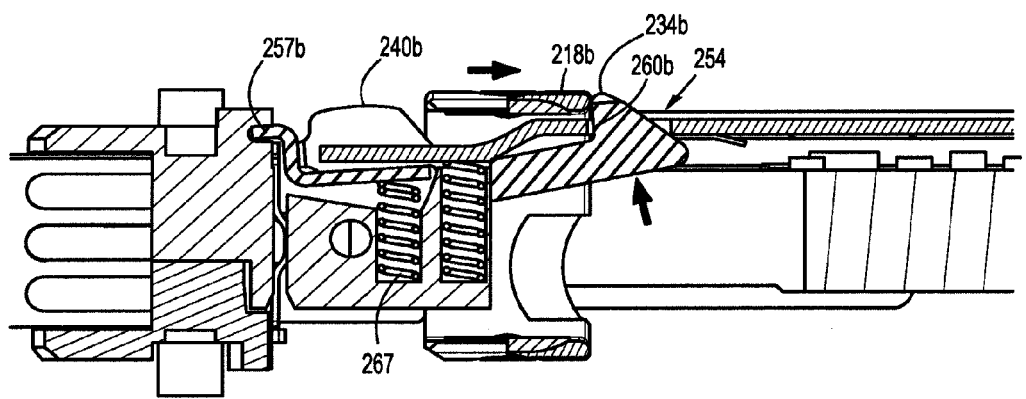
FIG. 35 is a partial, cross-sectional view of the cartridge illustrating the knife in the retracted configuration and the latch in a locked out configuration.

Continuing with reference to FIGS. 21-22, extending distally from body portions 240a, 240b are elongated members 248a, 248b from which trailing surfaces 260a, 260b extend in a generally orthogonal direction and culminate at protuberances 234a, 234b. Protuberances 234a, 234b are configured to selectively engage a recess 254 that is provided on an underside of jaw member 208, see FIG. 24 in combination with FIG. 31. Protuberances 234a, 234b and/or trailing surfaces 260a, 260b are configured to engage flange 218b of working end 201 of the drive member when protuberances 234a, 234b are engaged with recess 254 (FIG. 35). Extending distally from protuberances 234a, 234b are angled leading surfaces 249a, 249b that are configured to contact flange 218b of knife 205 when knife 205 is moved proximally back to the retracted configuration. Leading surfaces 249a, 249b allow flange 218b to slide past protuberances 234a, 234b to allow the working end 201 to be move proximally back to the retracted configuration (FIG. 32).

Figure 27:
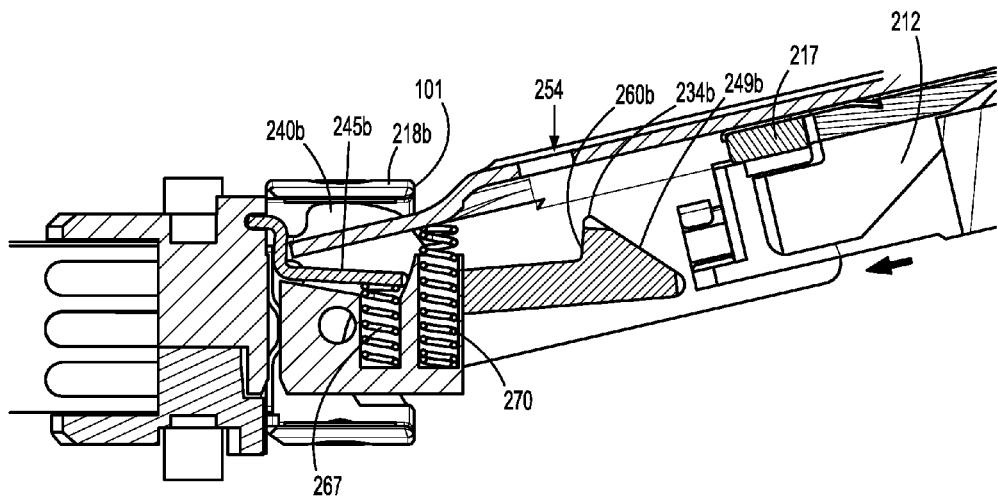
FIG. 27 is a partial, cross-sectional view of the cartridge illustrating the cartridge being installed to a corresponding jaw member.

Operation of surgical stapling apparatuses 100, 200 that utilize reload 206 is described herein. Initially, jaw members 208, 210 may be in an open configuration to load cartridge 212 onto jaw member 208 (FIGS. 14 and 26-27). In the open configuration, working end 201 is in a fully retracted configuration and flange 218b contacts body portions 240a, 240b. Moreover, arm portion 245b is pressed against springs 267.

Figure 29:
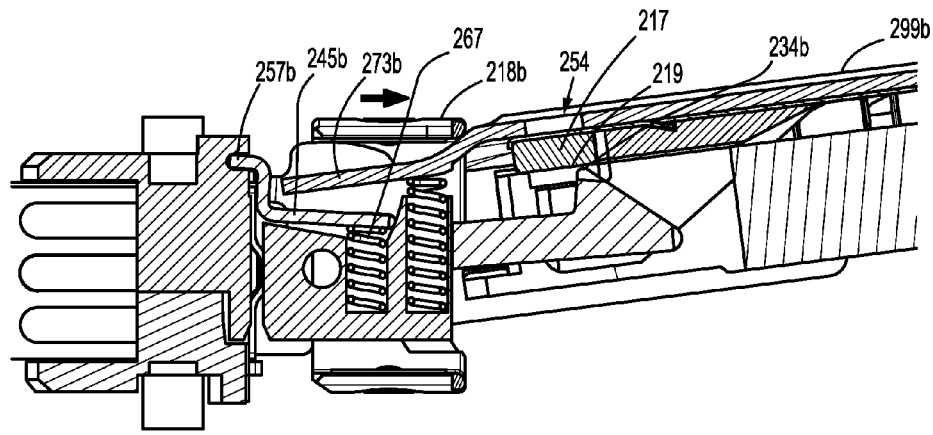
FIG. 29 is a partial, cross-sectional view of the cartridge illustrating the cartridge being approximated towards.

Thereafter, cartridge 212 may be inserted in jaw member 208. In the loaded configuration, blocking member 217 is positioned over recess 254 and in contact with protuberances 234a, 234b so as not to allow protuberances 234a, 234b to engage recess 254 prior to actuation sled 215 and/or the drive member being fired (FIGS. 28-29).

Subsequently, reload 206 including jaw members 208, 210 may be inserted through a portal, e.g., a trocar (or other suitable device), and positioned within a cavity of a patient adjacent tissue of interest. Tissue may be positioned between jaw members 208, 210 and jaw members 208, 210 may be approximated towards one another to grasp tissue for stapling thereof.

When the working end 201 is advanced to staple and sever tissue, flange 218b translates distally and moves out of engagement with body portions 240a, 240b. However, because blocking member 217 covers recess 254 and contacts with protuberance 234b, the working end 210 is free to continue to move distally and contact central cam wedge 213 of actuation sled 215, which, in turn, moves blocking member 217 out of contact with protuberances 234a, 234b. Accordingly, protuberances 234a, 234b are allowed to engage recess 254 (FIG. 31) as a result of bias of spring 267.

Figure 33:
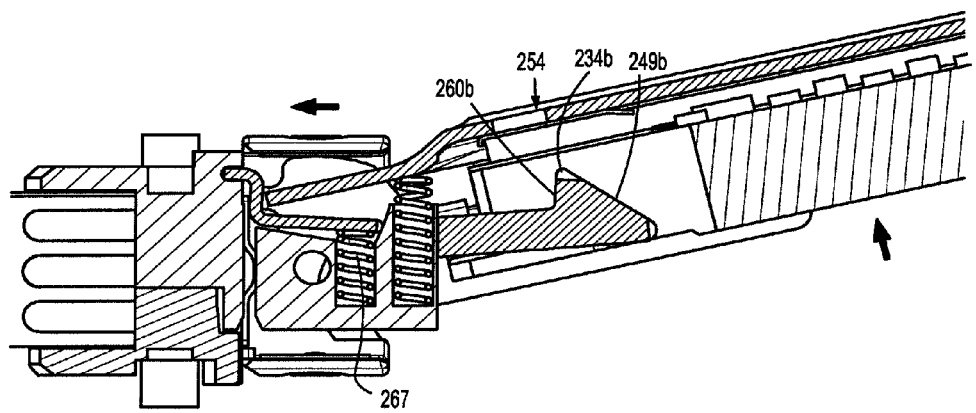
FIG. 33 is a partial, cross-sectional view of the cartridge illustrating the anvil and cartridge in an open configuration and the knife in the retracted configuration.
Figure 34:
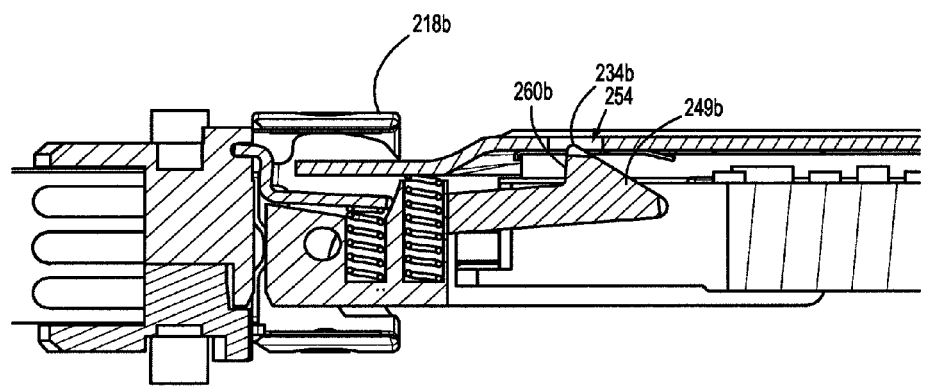
FIG. 34 is a partial, cross-sectional view of the cartridge illustrating the knife in the retracted configuration and the latch in position for removal of the reload from a trocar.

Subsequent to stapling and severing tissue, the working end 210 may be moved proximally and returned to its fully retracted configuration. Specifically, flange 218b of knife 205 contacts and slides past leading surfaces 249a, 249b so as to allow the working end 210 to be moved back to its fully retracted continuation (FIGS. 32-33). Flange 218b of knife 205 contacts body portions 240a, 240 and protuberances 234a, 234b are prevented from engaging recess 254. Accordingly, jaw members 208, 210 may be approximated towards one another for removal through the portal without interference from protuberances 234a, 234b (FIG. 34). That is, because the protuberances 234a, 234b are prevented from engaging recess 254, the likelihood of the protuberances 234a, 234b contacting the portal is reduced, if not eliminated. Latches 232a, 232b prevent forward movement of knife 205 until surgical stapling apparatuses 100, 200 are loaded with unused cartridge assembly.

In accordance with the instant disclosure, if flange 218b should come out of contact with body portions 240a, 240b, the biasing force provided springs 267 against arm portions 245a, 245b would cause protuberances 234a, 234b and/or trailing surfaces 260a, 260b to engage recess 254 and extend a predetermined distance therethrough to engage flange 218b and, thus, prevent knife 205 from traveling distally therepast (FIG. 35).

With reference to FIGS. 36-47, a reload 306 includes a locking mechanism according to another embodiment of the instant disclosure and is configured for use with surgical stapling apparatuses 100, 200 (FIGS. 1 and 2).

Figure 42:
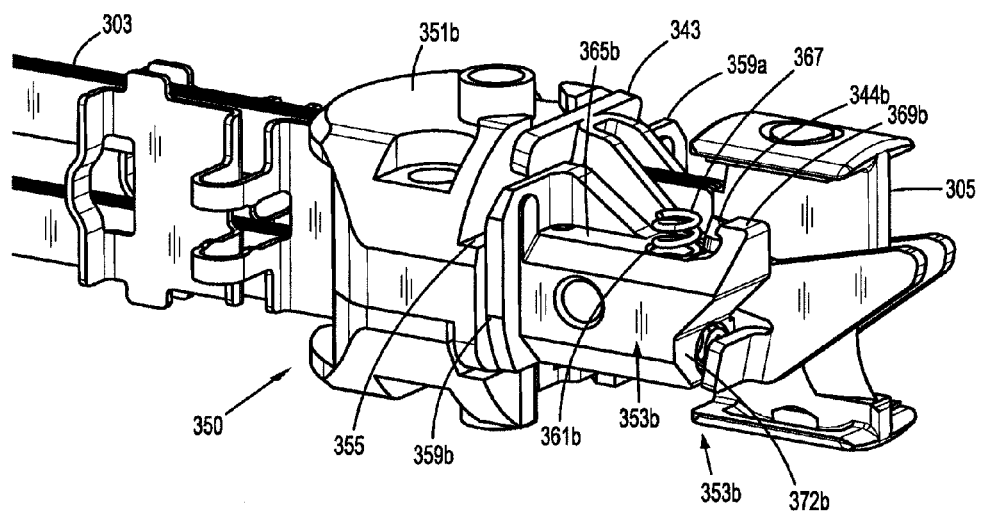
FIG. 42 is a perspective view of the reload with parts removed illustrating a pivot assembly.

With initial reference to FIGS. 37 and 42, a lower portion 351b of pivot assembly 350 includes two spaced-apart upright extensions 359a, 359b that are provided adjacent a shelf 355 to form a holding area for a locking member 343. Specifically, extensions 359a, 359b are positioned distally with respect to shelf 355 and extend a predetermined distance above shelf 355 to engage locking member 343 to prevent locking member 343 from moving distally past extensions 359a, 359b. Extensions 359a, 359b are spaced apart a predetermined distance from one another so as to allow a working end 301 to advance through a firing sequence of the surgical stapling apparatus 100, 200.

Figure 43:
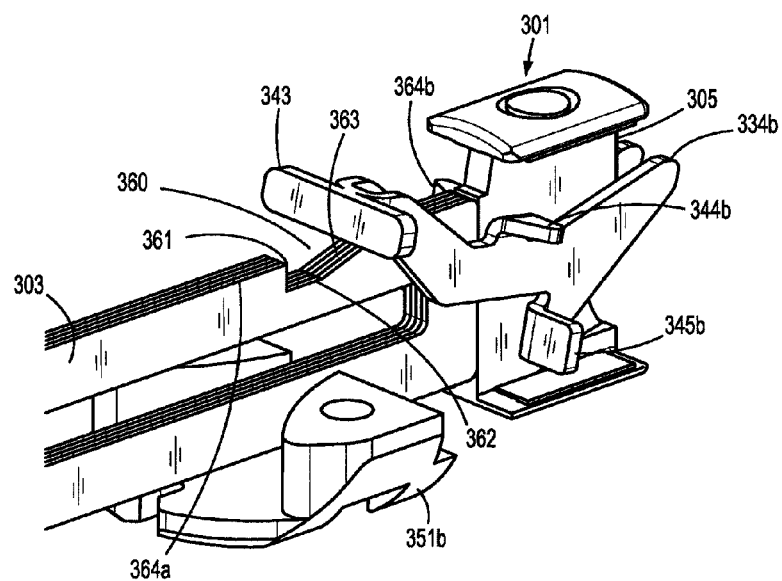
FIG. 43 is a perspective view of the reload with parts removed including a portion of the pivot assembly to illustrate a distal end of a knife assembly.
Figure 44:
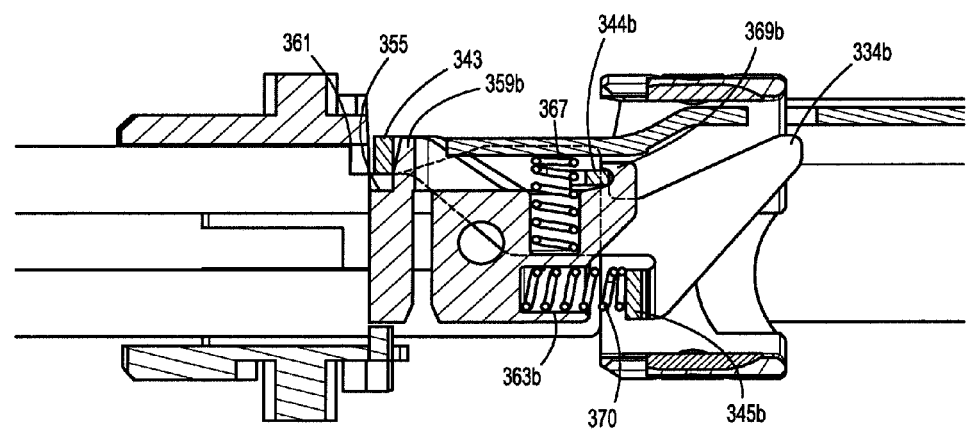
FIG. 44 is a partial, cross-sectional view of the reload with the cartridge not installed on a corresponding jaw member.
Figure 45:
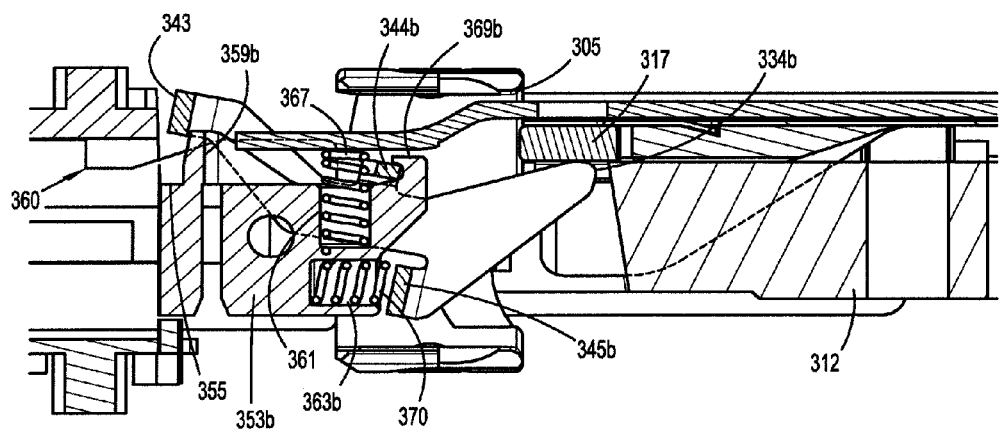
FIG. 45 is a partial, cross-sectional view of the cartridge installed on a corresponding jaw member.

Continuing with reference to FIG. 42, a leg member 353b extends from extension 359b and includes a generally flat top surface 365b defining a cavity 361b (see FIG. 45) that is configured to house an optional spring 367, e.g., a compression spring. A claw portion 369b extends in a generally upright orientation from top surface 365b and is configured to couple to a corresponding hinge member 344b of latch 332 (FIGS. 42 and 44) so as to allow hinge member 344b to pivot thereabout to facilitate sliding of locking member 343 along a notch 360 and/or a distal top surface 364b of drive beam members 303 (FIG. 43). A distal face 372b (FIG. 42) of leg member 353b defines a cavity 363b that is configured to house a spring 370, e.g., a compression spring, (FIGS. 44-45). Spring 370 includes a predetermined spring constant and is configured to contact a lateral extension 345b of latch 332 to bias latch 332 in a generally upright configuration.

Extension 359a is identical to extension 359b and includes all the aforementioned components described with respect to extension 359b. Accordingly, a detailed description of extension 359a is not provided.

Figure 40:
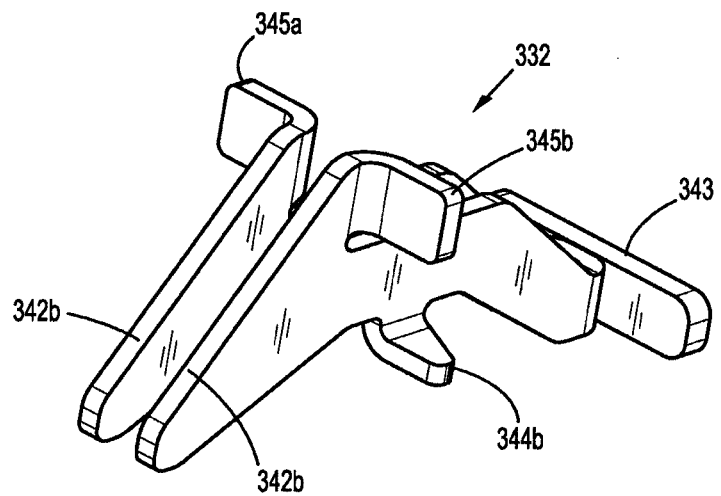
FIG. 40 is an enlarged area of detail of FIG. 38 illustrating a latch.
Figure 41:
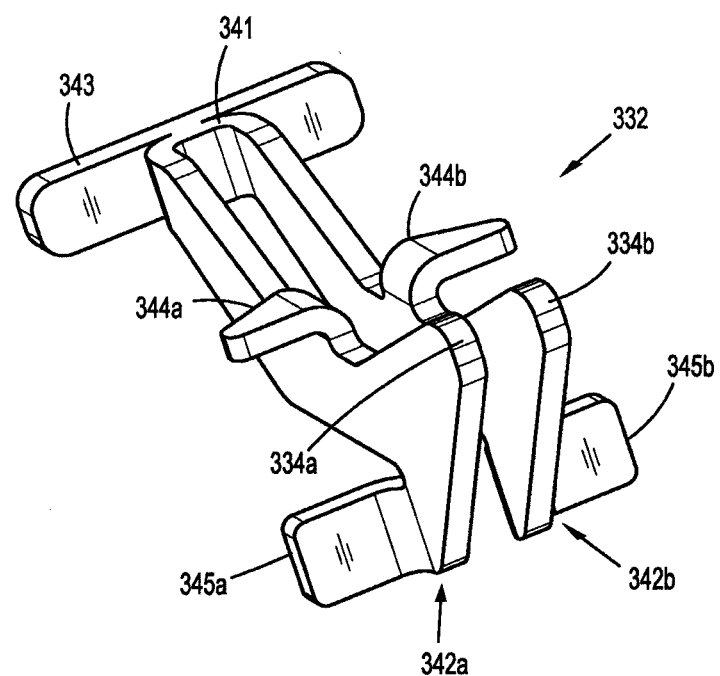
FIG. 41 is a perspective view of the latch depicted in FIG. 21 shown inverted.

Referring now to FIGS. 40-41, latch 332 is illustrated. Unlike latch 232, latch 332 is a single component having locking member 343 formed at a proximal end 341 and a bifurcated configuration including two (2) generally elongated members 342a, 342b extending distally therefrom. Members 342a, 342b are spaced apart a predetermined distance from one another to the working end 301 of the drive member to move therebetween during a firing sequence of surgical apparatuses 100, 200.

Hinge members 344a, 344b are provided at a medial portion of respective members 342a, 342b and include a generally arcuate configuration. Each of hinge members 344a, 344b extends a predetermined distance orthogonally from members 342a, 342b and curve outward therefrom to pivotably engage corresponding claw portions 369a, 369b to allow latch 332 to pivot as locking member 343 slides along drive beam members 303.

A pair of protuberances 334a, 334b are provided at a distal end of latch 332 and are configured to contact blocking member 317 (FIG. 45) when cartridge 312 is coupled to jaw member 308. Specifically, when protuberances 334a, 334b contact blocking member 317, latch 332 pivots about hinge members 344a, 344b which raises locking member 343 a predetermined distance and out of engagement with notch 360, as will be described in greater detail below.

Lateral extensions 345a, 345b are positioned proximally with respect to protuberances 334a, 334b and, when coupled to pivot assembly 350, adjacent coil sprigs 370 for contact therewith to urge protuberances 344a, 344b in a generally upward direction. Lateral extension 345b is configured to maintain coil spring 370 within cavity 363b as latch 332 pivots (FIGS. 44-45). Likewise, lateral extension 345a is configured to maintain coil spring 370 within the corresponding cavity (not explicitly shown) as latch 332 pivots.

FIG. 43 illustrates a distal end of drive beam members 303. Unlike drive beam members 103, drive beam members 303 collectively define notch 360. Specifically, notch 360 is provided adjacent to where a distal end of the drive beam members 303 couple to knife 305, as best seen in FIG. 43. Notch 360 may be formed during manufacture of drive beam members 303 by suitable methods including but not limited to etching, stamping, cutting, etc. Notch 360 includes a generally upright proximal wall 361 that extends from a generally flat medial portion 362. Wall 361 extends upwardly to meet with a proximal top surface 364a of drive beam members 303 and is configured to selectively engage locking bar 343 of a latch 332 to lock-out knife 305 so as to prevent misfiring of knife 305, as described in greater detail below. A ramp portion 363 extends distally from medial portion 362 and is provided towards a distal end of notch 360. Ramp portion 363 may extend at any suitable angle distally from medial portion 362 and is configured to slidably engage locking bar 343 when knife 305 is translated proximally and distally. Ramp portion 363 extends distally to meet a distal top surface 364b of drive beam members 303. Distal top surface 364b is configured to allow locking bar 343 to slide thereon when knife 305 is moved to a retracted configuration.

Operation of surgical stapling apparatuses 100, 200 that utilize reload 306 is described herein. Initially, jaw members 308, 310 may be in an open configuration to load cartridge 312 onto jaw member 308 (FIG. 44). In accordance with the embodiment illustrated in FIGS. 36-47, when cartridge 312 is not coupled to jaw member 308 the working end 301 of the drive member is locked out. Specifically, coil springs 370 contact lateral extensions 345a, 345b (in FIG. 44, only coil spring 370 is illustrated contacting extension 345b) to urge protuberances 343a, 343b in the generally upwardly direction, and locking member 343 in the generally downwardly direction into notch 360 and into contact with proximal wall 361. This contact between proximal wall 361 and locking member 343 maintains the working end 301 in a locked-out configuration.

Thereafter, cartridge 312 may be loaded onto jaw member 308. In the loaded configuration, blocking member 317 is positioned to contact with protuberances 334a, 334b. This contact between protuberances 334a, 334b and blocking member 317 forces protuberances 334a, 334b in a generally downwardly direction and causes latch 332 to pivot about pivot member 344a, 344b, which, in turn, causes locking member 343 to pivot in a generally upwardly direction and out of contact with proximal wall 361, see FIG. 45; with locking member 343 in this configuration, knife 305 may be fired.

Figure 46:
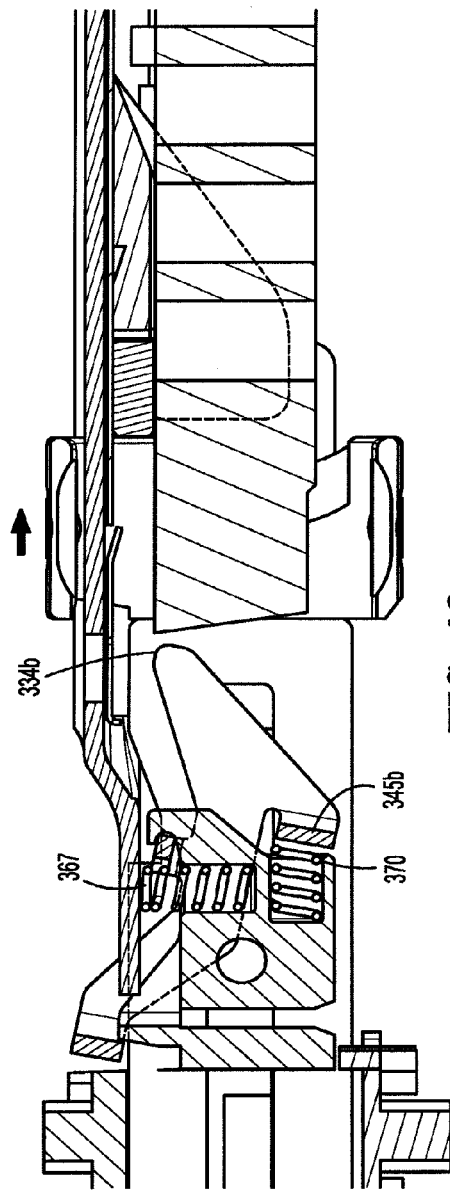
FIG. 46 is a partial, cross-sectional view of the cartridge illustrating a knife being translated therethrough.
Figure 47:
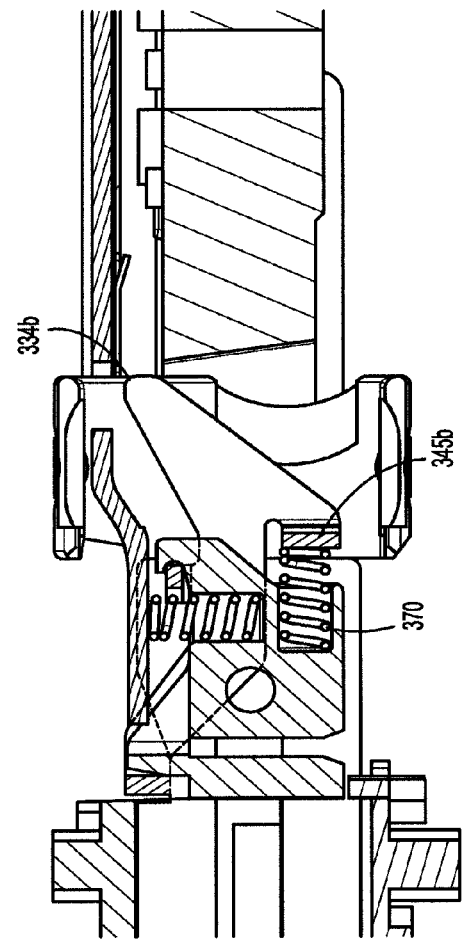
FIG. 47 is a partial, cross-sectional view of the cartridge illustrating a knife in a retracted configuration and locked out.

When working end 301 is advanced to staple and sever tissue, blocking member 317 moves distally with actuation sled 315 and out of contact with protuberances 334a, 334b (FIG. 46). Accordingly, protuberances 334a, 334b as a result of bias of spring 370 are once again forced in a generally upwardly direction and locking member 343 in the generally downwardly direction.

Subsequent to stapling and severing tissue, the working end 301 may be moved proximally and returned to its fully retracted configuration. As the working end 301 is being moved proximally, locking member 343 slides a predetermined distance along proximal top surface 364a until such time locking member 343 is forced downwardly into notch 360 and into contact with proximal wall 361. With locking member 343 engaged with notch 360, knife 305 is locked out and prevented from misfiring.

With reference to FIGS. 48-59, a reload 406 includes a locking mechanism according to an embodiment of the instant disclosure and is configured for use with surgical stapling apparatuses 100, 200 is illustrated. Loading unit 406 can generally be configured as described above.

Figure 50:
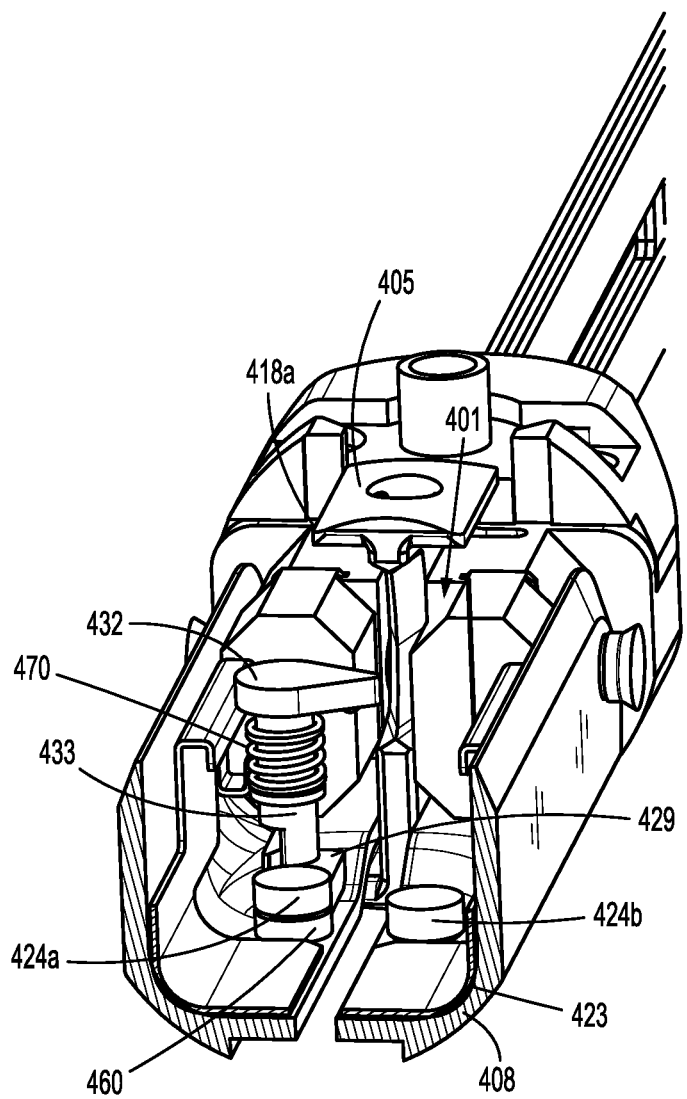
FIG. 50 is a partial, cut-away view of a cartridge shown in a pre-fired configuration.
Figure 51:
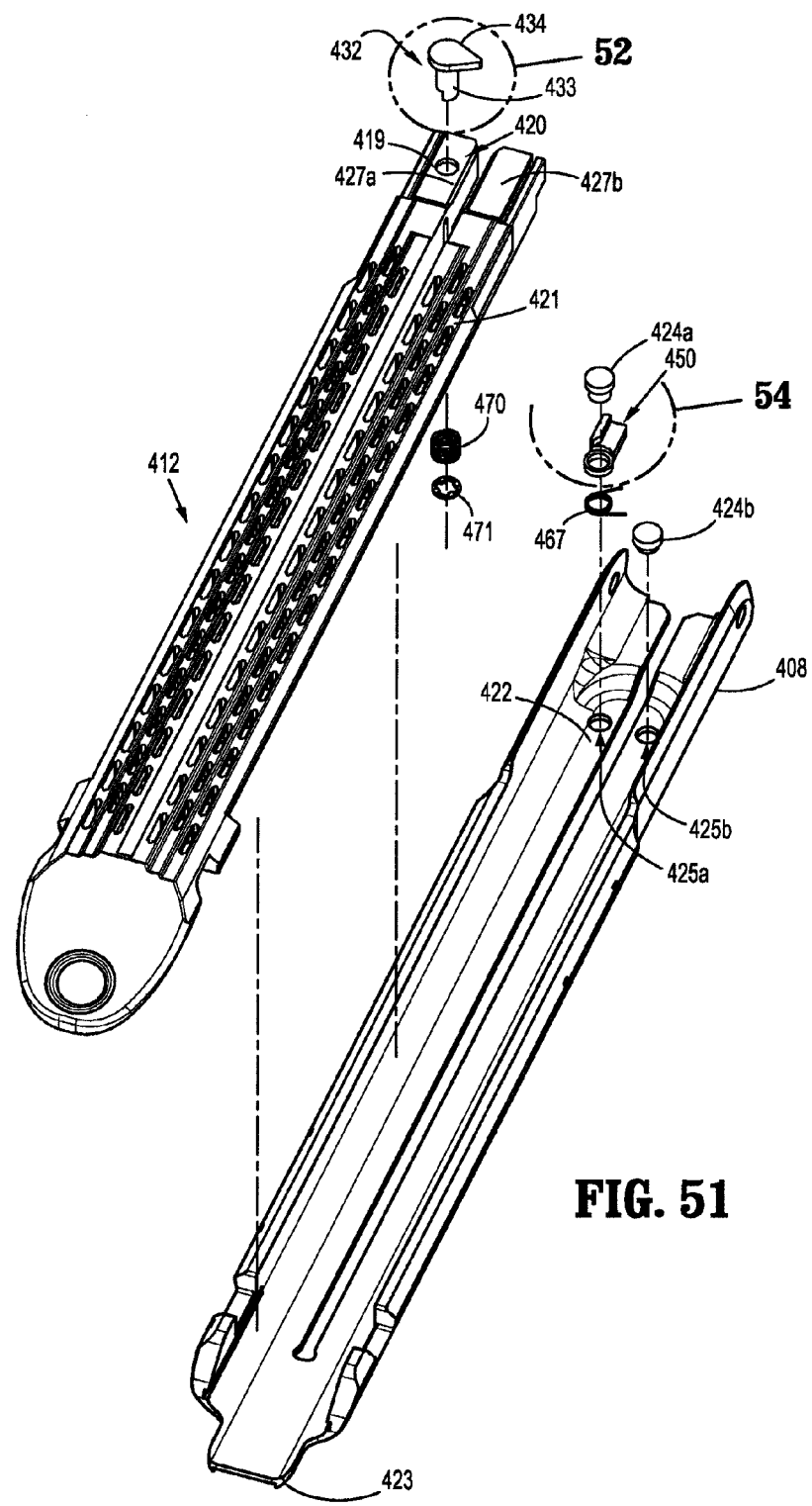
FIG. 51 is an exploded, perspective view of the cartridge with parts removed.

Beginning with reference to FIGS. 48-51, reload 406 includes a cartridge 412 that is similar to the previously described cartridge assemblies, e.g., cartridge 112. Unlike cartridge 112, however, one or more recessed platform areas 427a, 427b are provided adjacent to a proximal end of tissue contacting surface 421 of cartridge 412, as best seen in FIG. 51.

Figure 56:
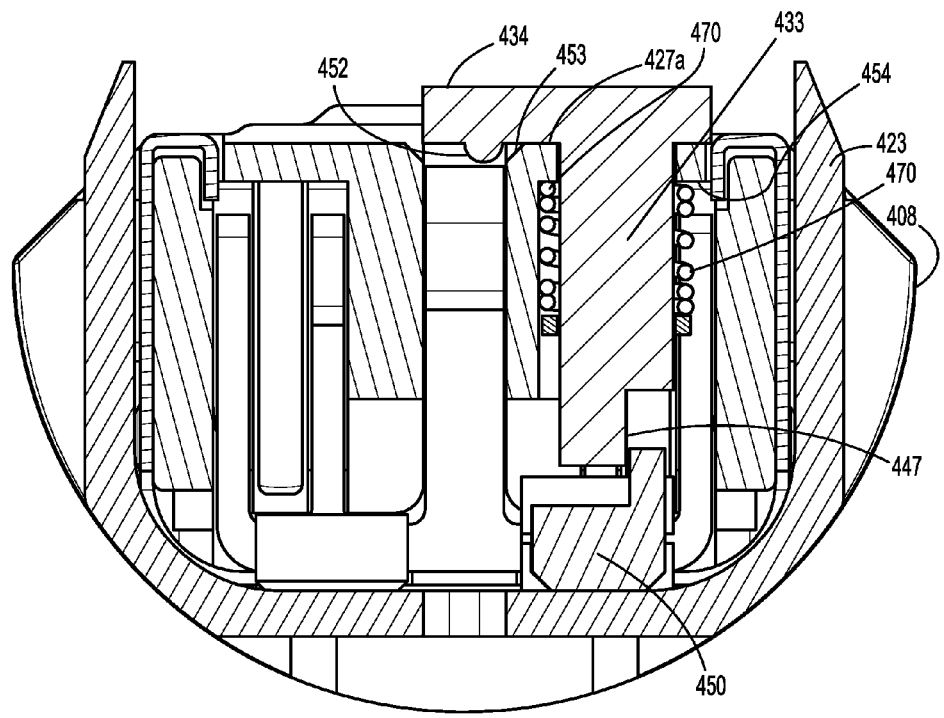
FIG. 56 is a cut-away view taken along line section 56-56 shown in FIG. 55.
Figure 57:
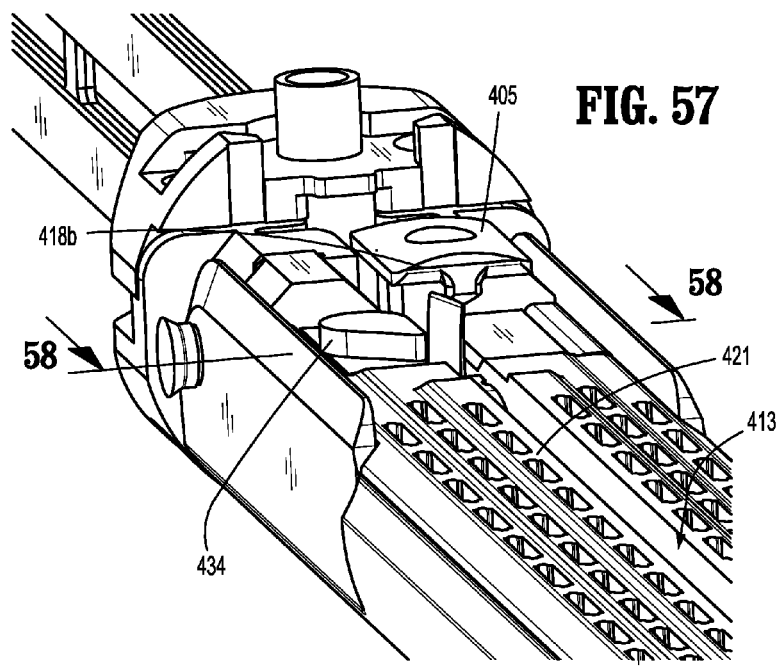
FIG. 57 is a partial, perspective view of the cartridge with parts removed illustrating a knife during a firing sequence.
Figure 58:
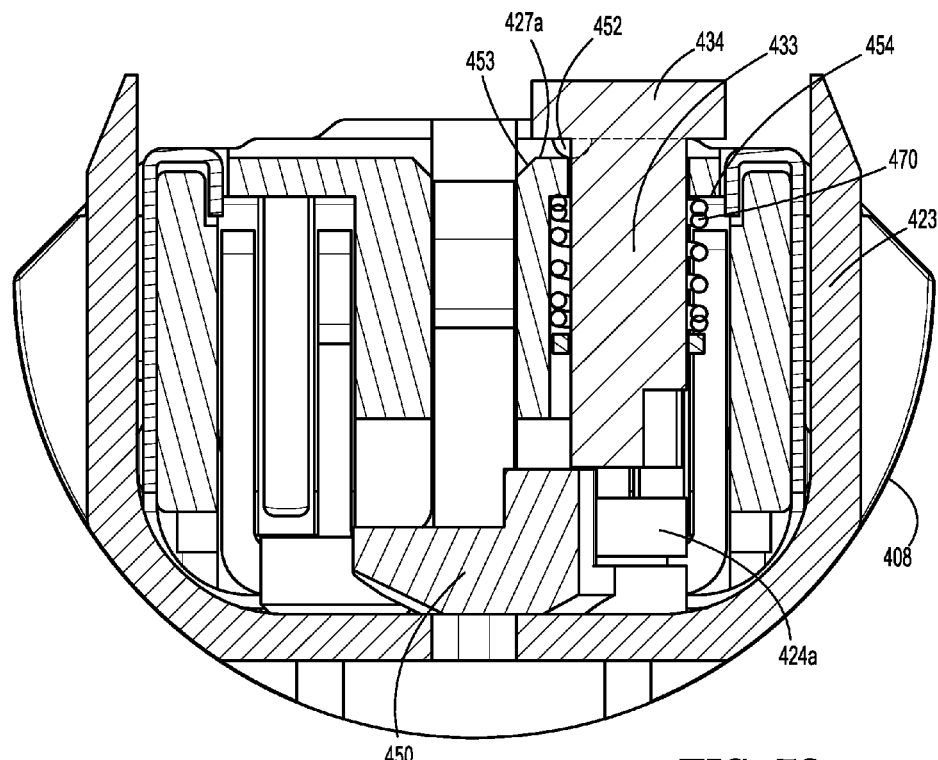
FIG. 58 is a cut-away view taken along line section 58-58 shown in FIG. 57.

An aperture 420 is defined through platform area 427a and is configured to receive a post 433 of an actuator 432 (FIG. 51). Aperture 420 is configured to allow rotation of post 433 and a head portion 434 of actuator 432 when head portion 434 is contacted by a top flange 418b disposed on knife 405 (FIGS. 48-49). In a pre-fired configuration (e.g., prior to top flange 418b contacting head portion 434), head portion 434 rests on platform area 427a (FIG. 56). In a post-fired configuration (e.g., subsequent to top flange 418b contacting head portion 434), head portion 434 is raised a predetermined distance above platform area 427a (FIG. 58).

A pair of apertures 425a, 425b of suitable configuration are defined through a bottom interior wall 422 of cartridge housing 423 and are configured to receive a corresponding rivet 424a, 424b therein (FIG. 51). Aperture 425a is in vertical registration with aperture 420 to align post 433 with an interlock 450 (see FIGS. 51 and 56).

Figure 52:
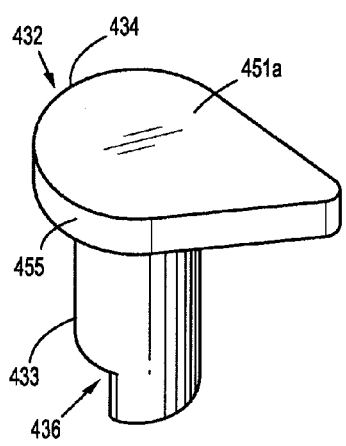
FIG. 52 is a perspective view of an actuator of the cartridge depicted in FIGS. 50 and 51.
Figure 53:
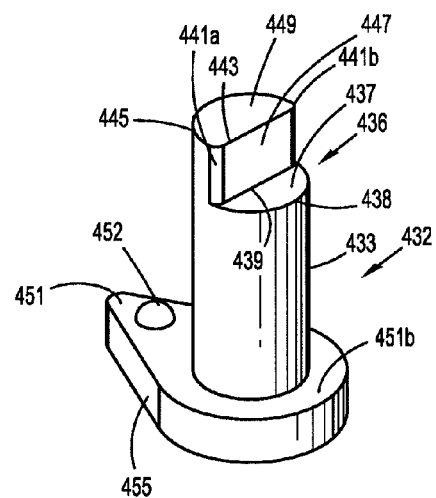
FIG. 53 is a perspective view of the actuator depicted in FIG. 52 shown inverted.
Figure 59:
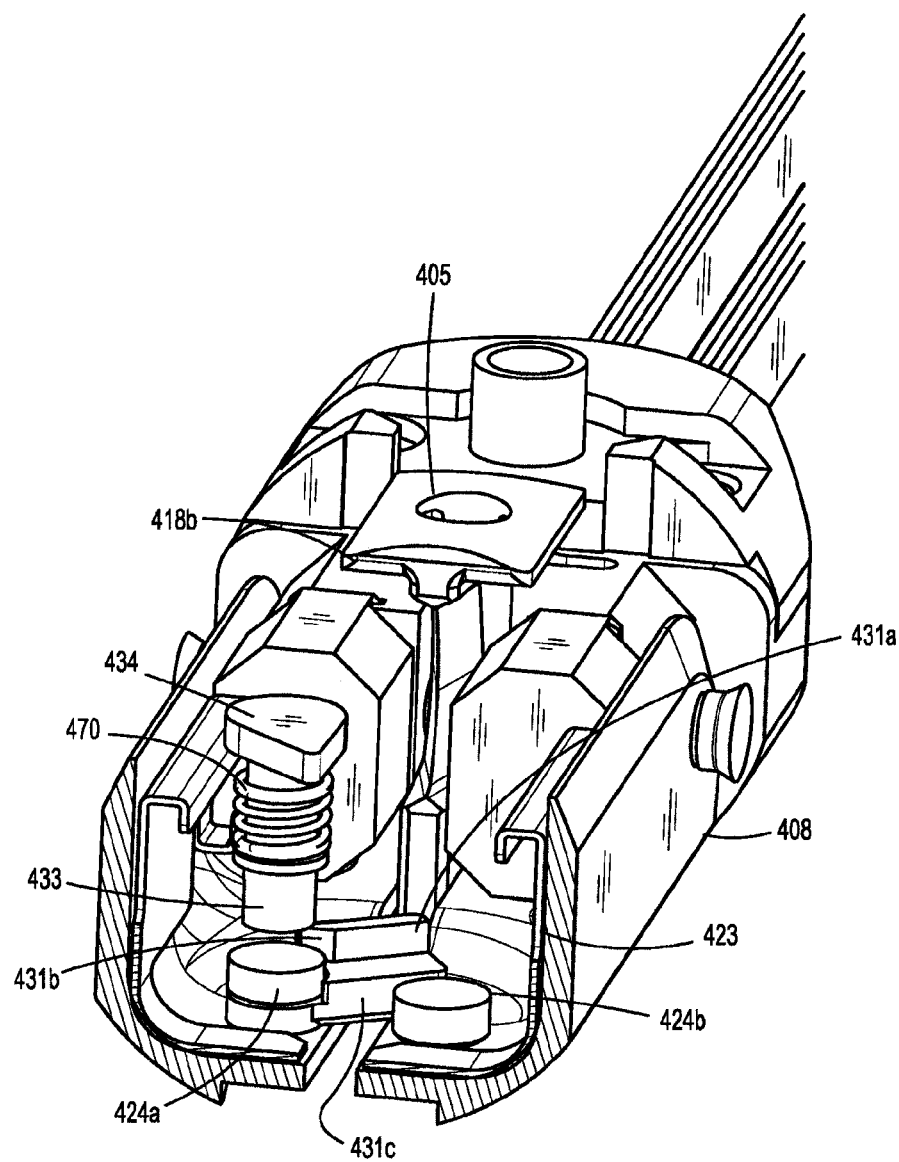
FIG. 59 is a partial, perspective view of the cartridge with parts removed illustrating the knife in a locked-out configuration.

With reference to FIGS. 52-53, actuator 432 is illustrated. Actuator 432 is rotatable within aperture 420 from an initial configuration wherein head portion 434 rests on platform 427a and post 433 is engaged with interlock 450 (FIG. 56) to a final configuration wherein head portion 434 is raised above platform 427a and post 433 is disengaged from interlock 450 (FIG. 58). When post 433 is engaged with interlock 450, working end 401 is free to move distally (FIGS. 50 and 56). Conversely, when post 433 is disengaged from interlock 450, the working end 401 is locked out and unable to move distally (FIGS. 58 and 59).

Continuing with reference to FIGS. 52-53, post 433 extends from head portion 434 and includes a generally elongated, cylindrical configuration. A notch 436 is provided adjacent a bottom portion of post 433 and is defined by a generally hemispherical top surface 437 that is defined by a semi-circular peripheral edge and an interior linear edge 439. Edge 439 meets a wall 447 of suitable configuration that extends in a generally orthogonal direction from top surface 437 to meet an interior linear edge 443 that meets with a semi-circular peripheral edge 445. Linear edge 443 and peripheral edge 445 define a generally hemispherical bottom surface 449. A pair of beveled side edges 441a, 441b are provided on wall 447 and extend between bottom and top surfaces 449 and 437, respectively, to facilitate rotation of post 433 about interlock 450.

Head portion 434 includes top and bottom surfaces 451a, 451b that are joined by a sidewall 455 extending in a curvilinear manner around top and bottom surfaces 451a, 451b to form a generally cone-like configuration (FIGS. 52-53). A tip 451 of head portion 434 is configured to extend at least partially within a knife channel 414 when actuator 432 and a working end 401 are in the pre-fired configuration, see FIG. 55 for example. A protuberance 452 is provided on bottom surface 451b (FIG. 53) and is configured to contact an interior edge 453 (FIG. 55) that extends into knife channel 414. Protuberance 452 may include any suitable configuration. In the illustrated embodiment, for example, protuberance 452 includes a generally rounded configuration, e.g., a dot-like configuration. The rounded configuration of protuberance 452 facilitates raising head portion 434 above platform area 427a when protuberance 452 contacts an interior edge 453 disposed adjacent platform area 427a (FIG. 56). In addition, interior edge 453 may be beveled/slanted (FIGS. 56 and 58) or otherwise configured to facilitate raising head portion 434 above platform 427a when protuberance contacts interior edge 453.

A spring 470 (e.g., a coil spring or other suitable resilient member (FIGS. 50-51) is operably coupled to post 433 and is configured to bias actuator 432 in an upward direction as shown in FIG. 50. Specifically, spring 470 is configured to contact an interior wall 454 that lies beneath tissue contacting surface 421 of cartridge 412 (FIGS. 56 and 58). One or more suitable coupling methods and/or devices may be utilized to couple spring 470 to post 433. In the illustrated embodiment, for example, a lock washer 471 is utilized to couple spring 470 to post 433 (FIG. 51). Lock washer 471 is also utilized to rotatably secure post 433 of actuator 432 within aperture 420.

Figure 54:
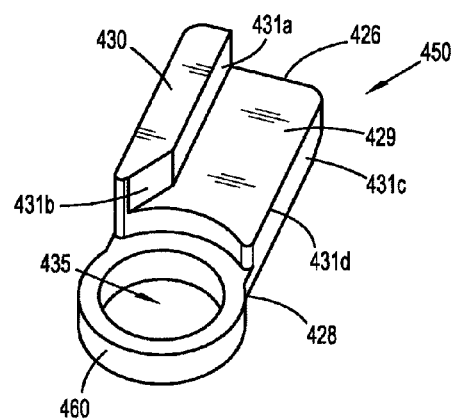
FIG. 54 is a perspective view of a rotating interlock of the cartridge.

Referring to FIG. 54, interlock 450 is illustrated. Interlock 450 is rotatable within aperture 425a from an initial configuration wherein interlock 450 is engaged with sidewall 447 of post 433 (FIG. 56) to a final configuration wherein interlock 450 is disengaged from sidewall 447 (FIG. 58) and engaged with rivet 424b (FIG. 59). When interlock 450 is engaged with sidewall 447, interlock 450 is positioned outside of a translation path of the working end 401 and the working end 401 is free to move distally (FIGS. 50 and 56). Conversely, when interlock 450 is disengaged from sidewall 447, interlock 450 is positioned inside of translation path of the working end 401 and the working end 401 is locked out and unable to move distally (see FIGS. 58 and 59 for example).

Continuing with reference to FIG. 54, interlock 450 includes a stepped configuration having a proximal end 426 and a distal end 428. Proximal end 426 includes a generally rectangular configuration having a relatively flat top surface 429 that is configured to receive bottom surface 449 of post 433 thereon (FIG. 50). A bottom surface (not explicitly shown) of interlock 450 is configured to slide along bottom interior wall 422 as interlock 450 rotates. A sidewall 431c extends from the bottom surface and meets top surface 429 forming an edge 431d. Sidewall 431c forms a first step and is configured to contact rivet 424b when interlock is in the post-fired configuration (FIG. 59). A generally rectangular upright extension 430 of suitable configuration is provided on top surface 429 and includes interior sidewall portions 431a, 431b that form second step. Sidewall portion 431a extends in a straight manner a predetermined distance from a proximal edge of top surface 429. Sidewall portion 431b extends at an angle a predetermined distance from a distal end of sidewall portion 431a. In the pre-fired configuration, sidewall 447 of post 433 is flush with sidewall portion 431a (FIG. 50). As post 433 rotates during a firing sequence, the beveled configuration of side edges 441a, 441b in conjunction with the angle at which sidewall portion 431b extends facilitates the transition of post 433 and interlock 450 from their pre-fired configuration to their post-fired configuration.

A generally circumferential sidewall 460 (FIG. 54) is provided at distal end 428 and includes an aperture 435 of suitable configuration defined therethrough. Aperture 435 is configured to receive rivet 424a therein for coupling interlock 450 to cartridge housing 423. Rivet 424a is configured to allow rotation of interlock 450 from the pre-fired configuration to the post-fired configuration (see FIGS. 50-51 and 59).

A spring 467, e.g., a torsion spring 467, having a suitable spring coefficient operably couples via one or more suitable coupling methods and/or devices to the bottom surface of interlock 450. (FIG. 51). Spring 467 is configured to bias interlock 450 towards the post-fired configuration, as best seen in FIG. 59. In the post-fired configuration, sidewall 431c engages rivet 424b to prevent rotation of interlock 450 past a predetermined point and lockout the working end 401 (FIG. 59).

Figure 55:
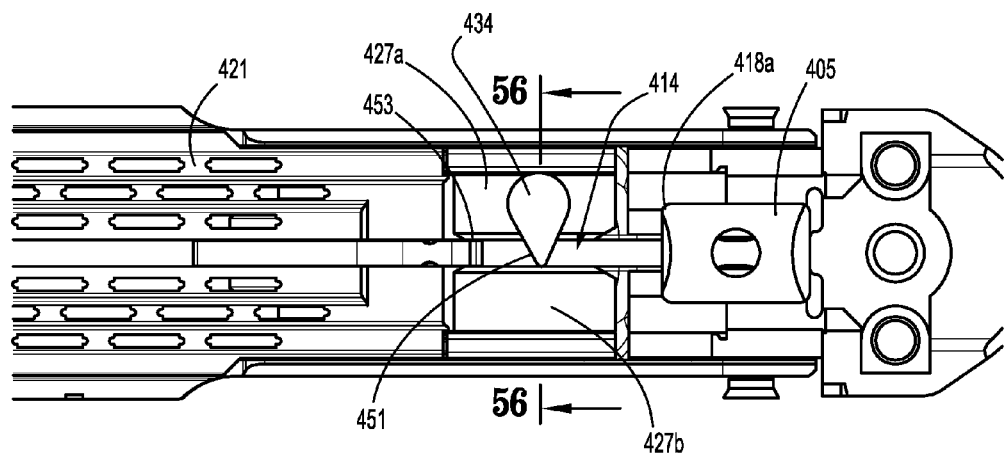
FIG. 55 is a top elevational view of the cartridge.

In use, actuator 432 is, initially, in the pre-fired configuration with tip 451 in the translation path of the working end 401 (FIGS. 50 and 55-56). Thereafter, the working end 401 may be advanced and flange 418a contacts head portion 434 of actuator 432, which, in turn, causes post 433 to rotate and protuberance 452 to ride up along interior edge 453 and onto platform 427a. As post 433 rotates, sidewall 447 rotates about sidewall 431a and begins to rise above extension 430 as a result of the upward bias of spring 470.

Once protuberance 452 is moved into position on platform 427a, sidewall 447 will be sufficiently raised so as to disengage sidewall 431a (FIGS. 57-79). As a result thereof, interlock 450 under the bias of spring 467 is forced to rotate until such time that sidewall 431c contacts rivet 424b (FIGS. 58-59).

The working end 401 may be moved back to its retracted, pre-fired configuration against the biasing force of spring 467. Specifically, a trailing surface (not explicitly shown, see trailing surface 118d in FIG. 3B for example) of the working end 401 contacts sidewall 431c so as to push interlock 450 proximally and out of engagement with rivet 424b until the working end 401 is moved therepast and to its retracted, pre-fired configuration. The trailing surface is desirably a cam surface or angled to facilitate this. Once the working end 401 is moved back to its retracted, pre-fired configuration, interlock 450 is once again forced forward by spring 467 and into contact with rivet 424b (FIG. 59). With interlock 450 in contact with rivet 424b, the working end 401 is locked out and prevented from distal translation.

With reference to FIGS. 60-76, a reload 506 includes a locking mechanism according to an embodiment of the instant disclosure and is configured for use with surgical stapling apparatuses 100, 200 is illustrated.

With reference initially to FIGS. 60-61, reload 506 includes a lockout assembly 530 that is configured to lock out a working end 501 to prevent misfiring thereof when a cartridge 512 is not coupled to jaw member 508 or when a spent cartridge 512 is coupled to jaw member 508. An actuator 532 is provided at a proximal end of cartridge 512 and is configured to selectively disengage lockout assembly 530 from a lock out configuration to allow advancement of the working end 501 of the drive member (FIGS. 62-66). The reload can generally be configured as discussed above.

Continuing with reference to FIGS. 62-65, an actuator 532 operably couples to actuation sled 515 and is positioned between wedge members 513b, 513c that are positioned to the right of a central support wedge 513a. Actuator 532 is translatable distally between wedge members 513a, 513b from an initial configuration (see FIGS. 60, 62-64 and 73-74) to a final configuration (see FIGS. 75-76). Actuator 532 is maintained in the initial configuration as a result of contact with a corresponding pusher 518 of plurality of double pushers 517b that are configured to eject corresponding fasteners 517a when contacted by wedge members 513b, 513c (see FIG. 65 in combination with FIG. 73 for example). In the illustrated embodiment corresponding pusher 518 is positioned first in the outer row of plurality of pushers 517 (see FIGS. 73 and 75 for example). Alternatively, a single, dedicated pusher (not shown) may be utilized to engage actuator 532; this single dedicated pusher may be configured to push a corresponding fastener, or may function to simply maintain actuator 532 in the initial configuration. Wedge member 513c is configured to contact pusher 518 and move pusher 518 in an upwardly direction to deploy corresponding one of the surgical fasteners 517a.

Figure 63:
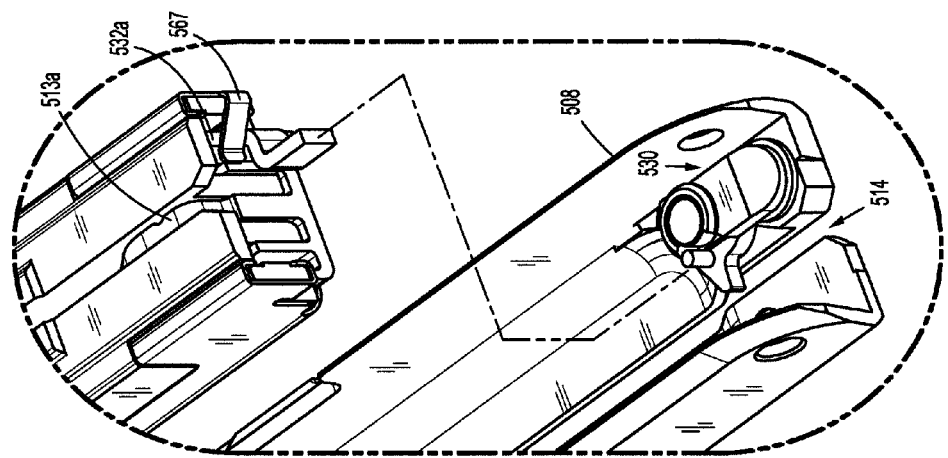
FIG. 63 is an enlarged area of detail of FIG. 62.
Figure 64:
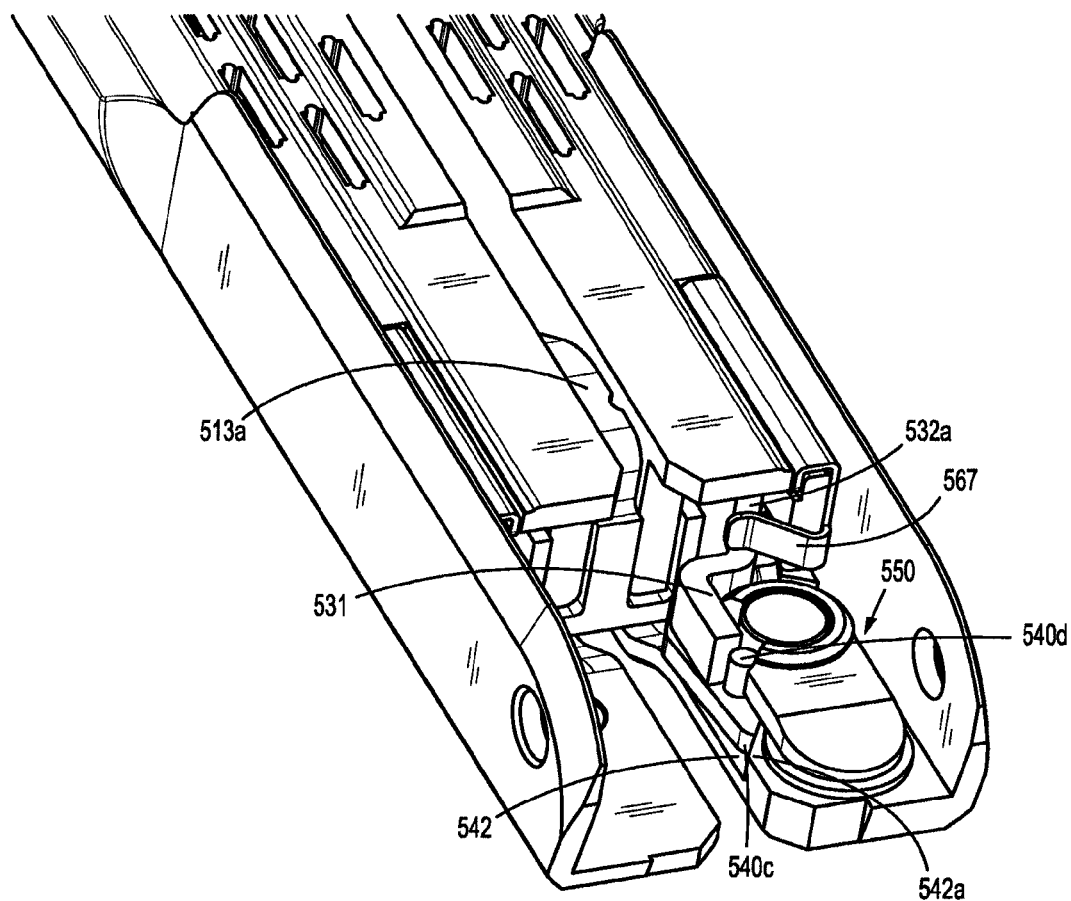
FIG. 64 is a partial, perspective view of a proximal end of the cartridge.
Figure 65:
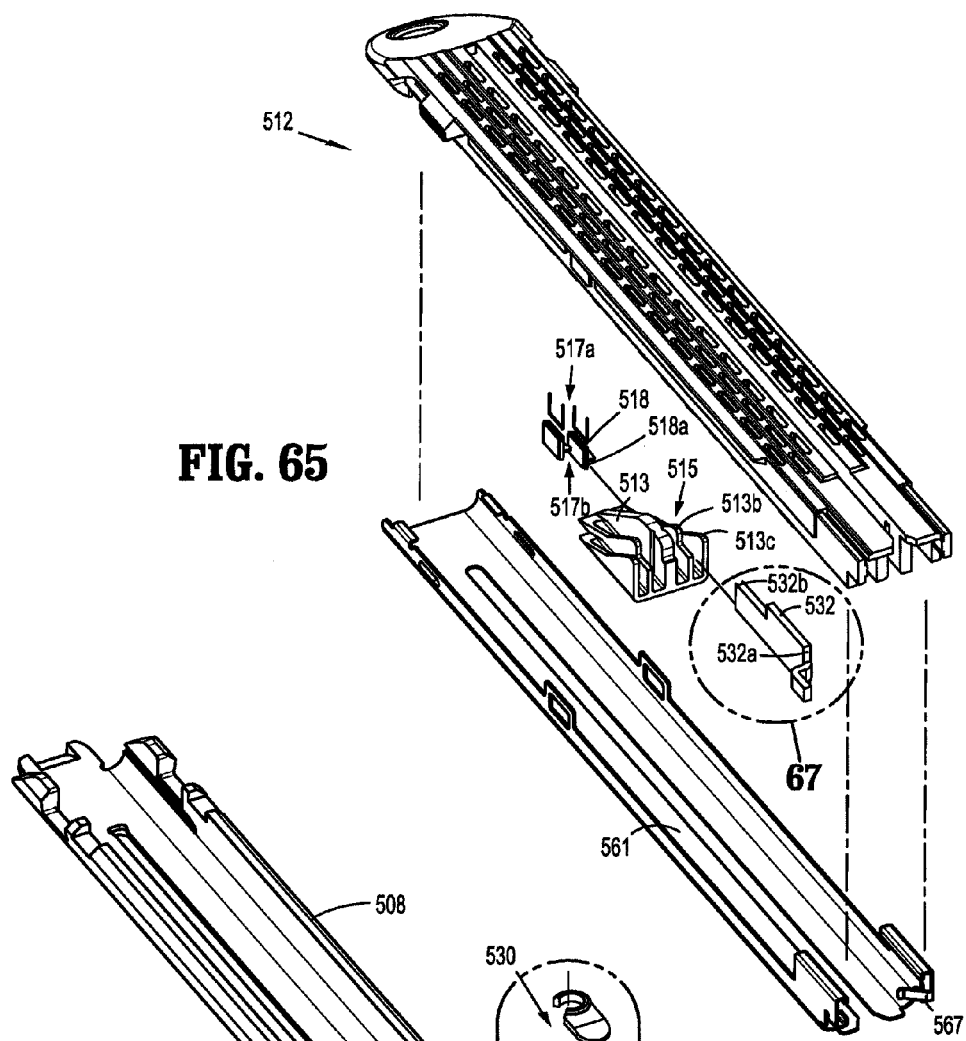
FIG. 65 is an exploded, perspective view of the cartridge assembly with parts separated.

A resilient member 567 (or other suitable device, e.g. a spring) is configured to contact a proximal end 532a of actuator 532 to bias a distal end 532b thereof against pusher 517b (FIGS. 60, 63-65). Specifically, resilient member 567 is provided on a bottom portion or cover 561 of cartridge 512 (as best seen in FIG. 65). Spring 567 includes a generally elongated configuration and extends distally in a generally inwardly manner at an angle from cover 561 to bias actuator 532 distally into contact with pusher 518. Resilient member 567 may include any suitable spring constant or configuration or shape. In accordance with the instant disclosure, a suitable spring constant will be sufficient so as allow resilient member 567 to bias actuator 532 against pusher 518 and translate actuator 532 a predetermined distance past pusher 518, as will be described in greater detail below.

Actuator 532 may be formed from any suitable material including but not limited to metal, plastic, etc. In the illustrated embodiment, actuator 532 is formed from metal, e.g., sheet metal, and includes a generally elongated configuration having proximal and distal ends 532a, 532b, respectively (FIGS. 65 and 67).

Distal end 532b includes a leading edge 533 that is configured to engage a corresponding trailing edge 518a (FIGS. 65 and 75) of pusher 518. In embodiments, such as the illustrated embodiment, leading edge 533 includes a generally arcuate configuration (e.g., a groove) to facilitate contact with trailing edge 518a that includes a complementary arcuate configuration (e.g., a tongue) of leading edge 533. Alternatively, leading edge 533 and trailing edge 518a may be relatively flat, or may have some other shape.

In the final configuration, e.g., a post-fired configuration, leading edge 533 extends a predetermined distance past trailing edge 518a. The predetermined distance that leading edge 533 may extend past trailing edge 518a may range from about 0.050 inches to about 0.070 inches. In other words, actuator 532 has been moved distally by resilient member 567 away from locking lever 540.

A notch 535 is provided on actuator 532 and is defined by a back wall portion 535a that extends orthogonally from a top surface 535b (FIG. 67). Notch 535 is configured to engage a blocking member 536 extending downwardly from a top interior wall provided within cartridge 512 (FIGS. 73 and 75). Blocking member 536 is configured to contact back wall portion 535a to limit distal translation of actuator 532 during a firing sequence such that leading edge 533 extends past trailing edge 518a within the above specified ranges. Moreover, blocking member 536 and top surface 535b may serve to guide actuator 532 as actuator 532 is translated between wedge members 513b, 513c.

A generally elongated finger portion 531 of suitable configuration is provided at proximal end 532a and extends proximally therefrom to move lockout assembly 530 into a pre-fired configuration when cartridge 512 is coupled to jaw member 508, see FIGS. 64 and 67. In the illustrated embodiment, a distal end 531a of finger portion 531 extends inwardly from proximal end 532a to laterally offset the finger portion 531 from proximal end 532a. Alternatively, finger portion 531 may be provided on an interior sidewall 532c (FIG. 67) of actuator 532. Finger portion 531 is offset from proximal end 532a to align and couple with lockout assembly 530 when cartridge 512 is coupled to jaw member 508 (see FIGS. 63-64).

Figure 62:
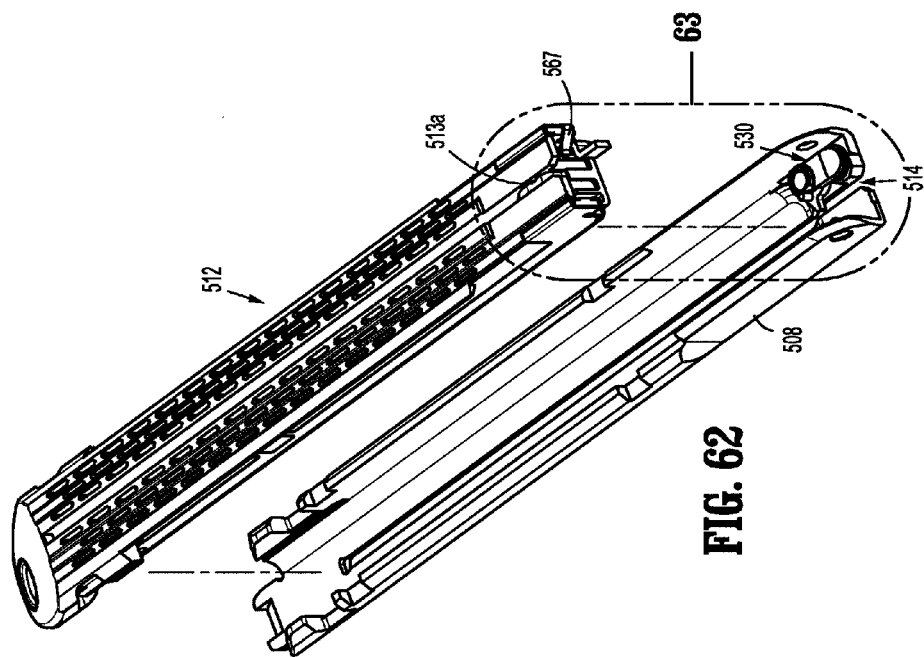
FIG. 62 is an exploded, perspective view of the cartridge assembly of FIG. 60 with parts separated.

With reference to FIGS. 60, 62-64, 66 and 68 lockout assembly 530 is illustrated. As noted above, lockout assembly 530 is configured to lock out the working end 501 to prevent misfiring thereof when cartridge 512 is not coupled to jaw member 508 or when a spent cartridge 512 is coupled to jaw member 508. With this purpose in mind, lockout assembly 530 is operably positioned at a proximal end of jaw 508 and located distal of pivot assembly 550 (FIGS. 62-63). Lockout assembly 530 includes three main components, a locking lever 540 (FIG. 68), a mounting member 560 and a spring clip 570.

Figure 66:
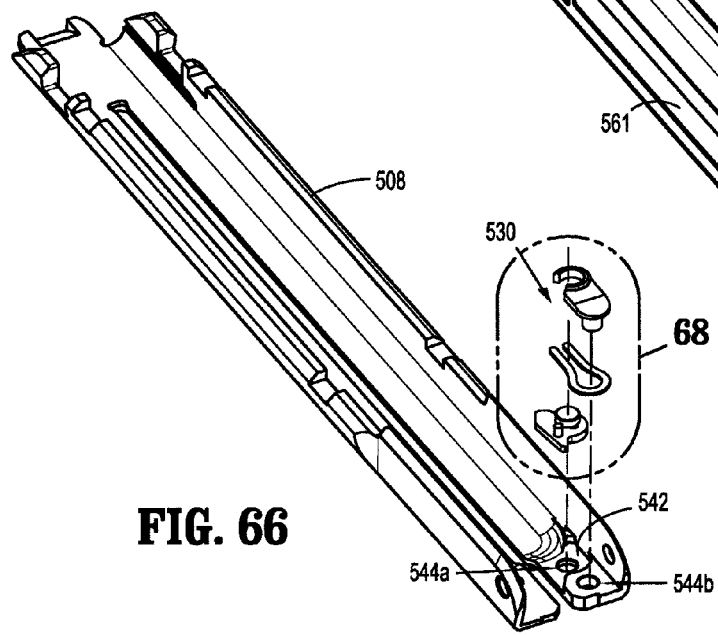
FIG. 66 is an exploded, perspective view of a jaw member of the reload with parts separated.
Figure 71:
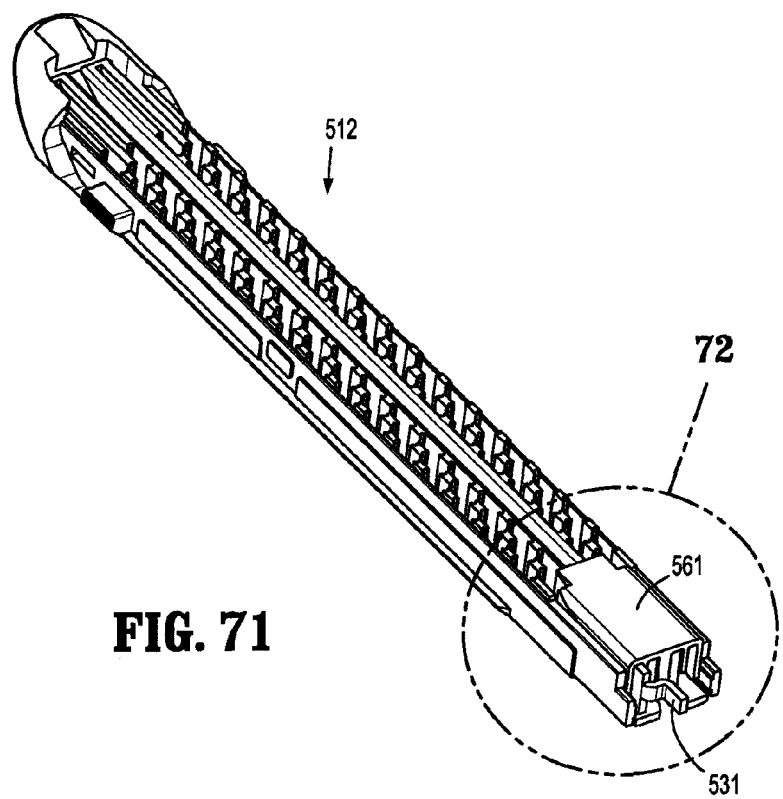
FIG. 71 is a perspective view of the cartridge shown with a portion of a cover removed.
Figure 72:
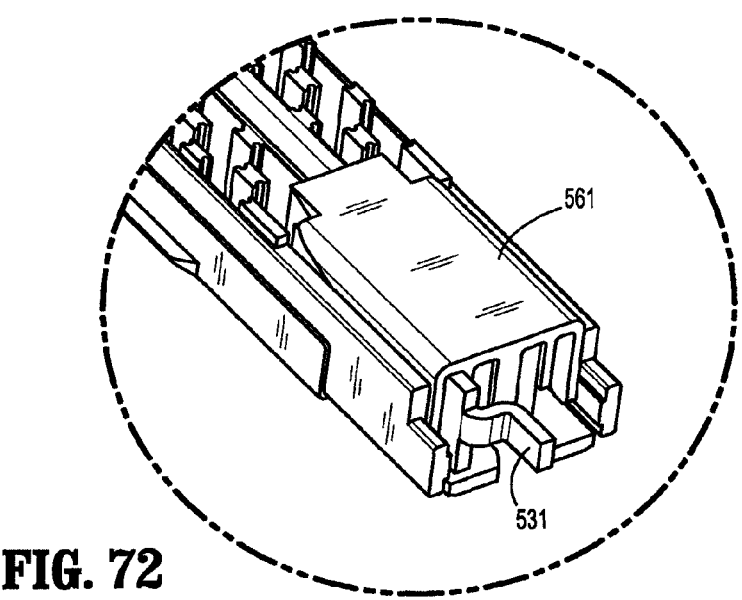
FIG. 72 is an enlarged area of detail of FIG. 71.

Continuing with reference to FIG. 68, locking lever 540 includes a base portion 540a of suitable configuration that is configured to seat within a recess 542 provided at a proximal end of jaw member 508, see FIGS. 64 and 66 for example. A bottom surface of base portion 540a is provided with a generally circumferential protuberance (not explicitly shown) that is configured to be received within a corresponding aperture 544a (as best seen in FIG. 66) that is provided within recess 542 and defined through a bottom wall portion of jaw member 508. In an assembled configuration, the protuberance is configured to allow rotation of locking lever 540 within recess 542 when locking lever 540 is contacted by finger portion 531, see FIGS. 62-64.

A generally arcuate cutout 540b is provided on base portion 540a and includes a tip 540c configured to contact a corresponding sidewall 542a that helps define recess 542 (see FIGS. 64 and 67). Moreover, a boss 540d of suitable configuration extends in a generally orthogonal direction from base portion 540a and is configured to contact finger portion 531. Specifically, when cartridge 512 is coupled to jaw member 508, finger portion 531 of actuator 532 contacts boss 540d and rotates locking lever 540 until boss 540d contacts a trailing edge 564 of mounting member 560 and tip 540c contacts sidewall 542a of recess 542 (FIG. 64). Moreover, tip 540c is configured to contact and slide against a bottom portion 503a of drive beam members 503 (FIG. 73) after finger portion 531 of actuator 532 is disengaged from boss 540d, as will be described in more detail below.

A protrusion 540e is provided on base portion 540a and is supported by a post 540f that extends from base portion 540a (FIGS. 68-70). Protrusion 540e includes a generally circumferential configuration and is configured to rotatably engage a corresponding opening 562 provided on mounting member 560 for securing locking lever 540 within recess 542. Post 540f includes a generally oblong configuration and is configured to be received between spaced-apart leg portions 571a, 571b of spring clip 570 (as best seen in FIGS. 69-70A) so as to allow rotation thereof including locking lever 540 within aperture 544a. Specifically, leg portions 571a, 571b are configured to bias post 540f and, thus, locking lever 540 into a locked out configuration. More specifically, when cartridge 512 is coupled to jaw member 508, finger portion 531 contacts boss 540d and urges boss 540d proximally, which, in turn, partially rotates post 540f into contact with and against the biasing force provided by leg portions 571a, 571b (FIG. 70B). When finger portion 531 moves out of contact with boss 540d, tip 540c is urged into contact with and slides against bottom portion 503a of drive beam members 503 until such time that the working end 501 is moved proximally past tip 540c and back to the retracted configuration. Once the working end 501 is moved to the retracted configuration, tip 540c of locking member 540 is moved back to the locked out configuration. The biasing force provided by leg portions 571a, 571b on post 540f prevents the working end 501 from moving past tip portion 540c. That is, the biasing force provided by leg portions 571a, 571b on post 540f is greater than the force utilized to fire and/or translate the working end 501 distally and, therefore, leg portions 571a, 571b do not move apart from one another as a result of contact between the working end 501 and tip portion 540c as the working end 501 is moved distally (FIG. 70a).

Leg portions 571a, 571b meet at a generally arcuate proximal end 572 of spring clip 570 (FIGS. 68-70). The arcuate configuration of proximal end 572 provides a suitable spring constant and is configured to allow leg portions 571a, 571b flex or move a predetermined distance away from one another when post 540f contacts leg portions 571a, 571b. An aperture 576 of suitable configuration is provided adjacent proximal end 572 and is configured to receive therethrough a corresponding protrusion 563 that is provided on a bottom surface of mounting member 560 (FIG. 68).

Mounting member 560 includes a generally elongated configuration having opening 562 at a distal end thereof and protrusion 563 at a proximal end thereof to mount locking lever 540 to jaw member 508 (FIG. 68). Specifically, protrusion 540e is positioned within aperture 562 and protrusion 563 is positioned through aperture 576 and through an aperture 544b provided within recess 542 adjacent aperture 544a (see FIG. 66).

In use, locking lever 540 is, initially, in a locked out configuration (FIGS. 62-63) with tip 540c positioned across the knife channel 514 to prevent distal translation of the working end 501. Thereafter, cartridge 512 may be coupled to jaw member 508. In doing so, finger portion 531 contacts and pushes boss 540d proximally to partially rotate locking lever 540 within recess 542. Locking lever 540 rotates within recess 542 until boss 540d contacts trailing edge 564 and tip portion 540c contacts sidewall 542c (FIGS. 73-74). At this time, post 540f moves leg portions 571a, 571b away from one another and is biased by the force provided therefrom (FIG. 70B). Concomitantly, spring 567 biases actuator 532 distally against pusher 518 (see FIG. 63 in combination with FIG. 74).

With locking lever 540 and actuator 532 in the pre-fired configuration, the working end 501 including actuation sled 515 may be fired to staple and, subsequently, sever the stapled tissue. When fired, the working end 501 including sled 515 are moved distally and wedge 513c contacts pusher 518 so as to allow actuator 532 to move a predetermined distance distally in a manner as described hereinabove. Distal translation of actuator 532 allows locking lever 540 to move back to the locked-out configuration (FIGS. 75-76). Specifically, when the working end 501 is moved proximally past locking lever 540 to the retracted configuration, locking lever 540 against the bias of spring clip 570 is moved back to the locked out configuration. Once in the retracted configuration, the working end 501 is locked out from translating distally past tip portion 540c as a result of the biasing force provided on post 540f by leg portions 571a, 571b.

With reference to FIGS. 77-92, a reload 606 includes a locking mechanism according to an embodiment of the instant disclosure and is configured for use with surgical stapling apparatuses 100, 200 is illustrated.

With reference initially to FIGS. 77-78, reload 606 includes a lockout assembly 630 and an actuator 632 that collectively are configured to lock out the working end 601 to prevent misfiring thereof subsequent to cartridge 612 being coupled to jaw member 608. Actuator 632 is provided at a proximal end of cartridge 612 and is configured to selectively engage lockout assembly 630 that is provided at a proximal end of jaw member 508 (see FIGS. 78-81 for example).

A notch 603a of suitable configuration is defined at a distal end of drive beam members 603 adjacent the working end 601 (FIG. 78). Notch 603a includes a proximal wall 603b that is configured to contact at least a portion of a locking lever 640 of lockout assembly 630 (see FIG. 92 for example) when locking lever 640 is in the locked out configuration.

Continuing with reference to FIGS. 78-81 and 85, actuator 632 operably couples to cartridge 612 and is configured to selectively engage locking lever 640. Actuator 632 includes a generally elongated configuration having proximal and distal ends 632a, 632b, respectively. Distal end 632b includes a protuberance 634 that projects inwardly and is configured to contact a cam feature 616 that is disposed on actuation sled 615 adjacent a top surface of a central cam wedge 613 (FIG. 85). A tab 636 of suitable configuration is provided on a bottom surface 634c of actuator 632 and is configured to movably seat within a corresponding aperture 622a having a complementary configuration provided at a proximal end of cartridge 612 (see FIG. 80 in combination with FIG. 85). Specifically, tab 636 is configured to move in a generally sideways or lateral direction when protuberance 634 is contacted by cam feature 616 as actuation sled 615 is moved distally.

A support structure 638 is provided on bottom surface 632c adjacent proximal end 632a and includes a beam portion 638a and post portion 638b (FIG. 84). Beam portion 638a is configured to be received within a recess 642 that is provided at a proximal end of cartridge 612 (FIG. 84). Beam portion 638a includes a generally elongated configuration and includes a detent 637 at a distal end thereof (FIG. 84). Detent 637 is positioned proximally with respect to tab 636 and is received within a corresponding aperture 632b that is provided at a proximal end of cartridge 612 adjacent aperture 622b (FIGS. 78 and 85). Detent 637 is configured to couple actuator 632 to cartridge 612 so as to allow tab 636 to move within aperture 622a in a manner as described above. Specifically, contact between cam member 616 and protuberance 634 causes actuator 632 to pivot about detent 637, which, in turn, causes tab 636 to move sideways within aperture 622a. Post portion 638b extends in a generally orthogonal direction from bottom surface 632c and is configured to contact and rotate locking member 640 into an unlocked configuration when cartridge 612 is coupled to jaw member 608. Moreover, as actuator 632 pivots about detent 637, post portion 638b moves out of contact with locking lever 640 and allows locking lever 640 to return to the locked out configuration (FIGS. 87-88 and 91-92).

Figure 81:
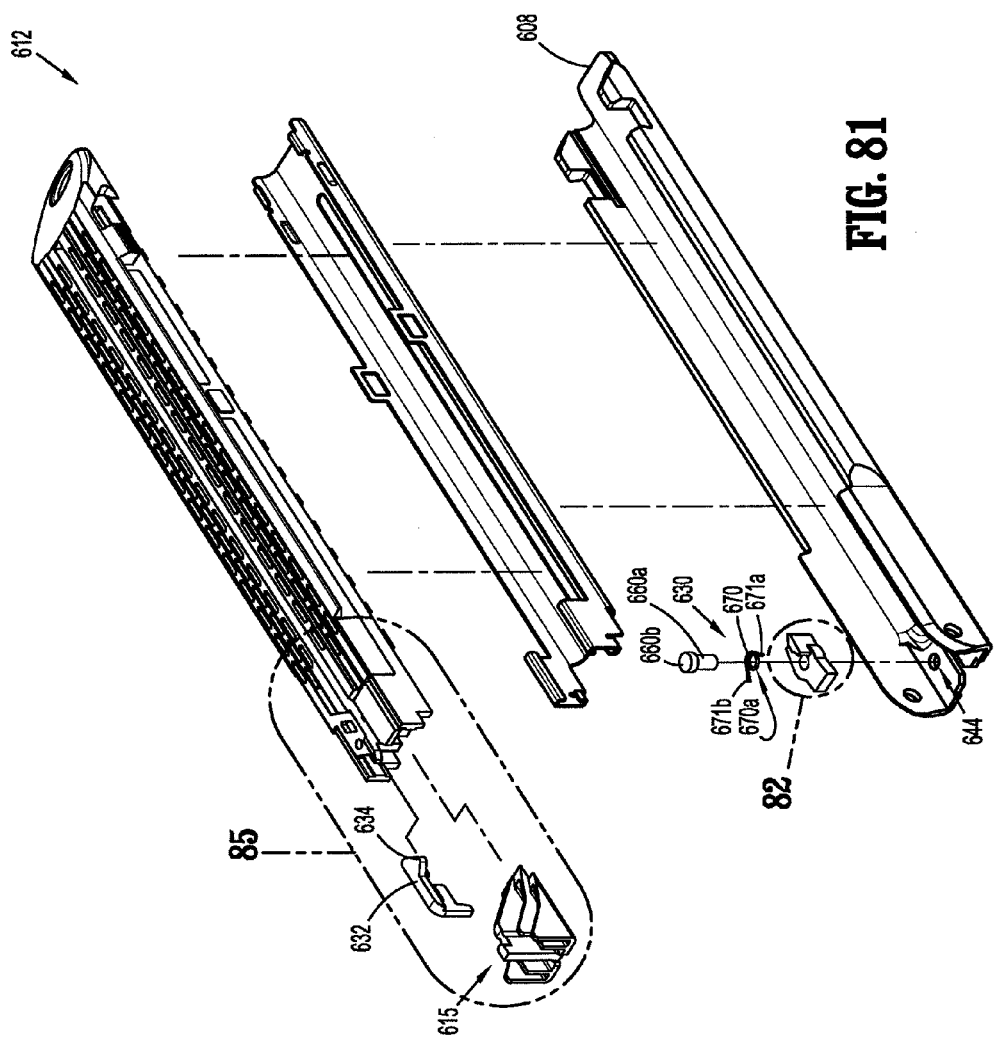
FIG. 81 is an exploded, perspective view the jaw member with parts separated.
Figure 86:
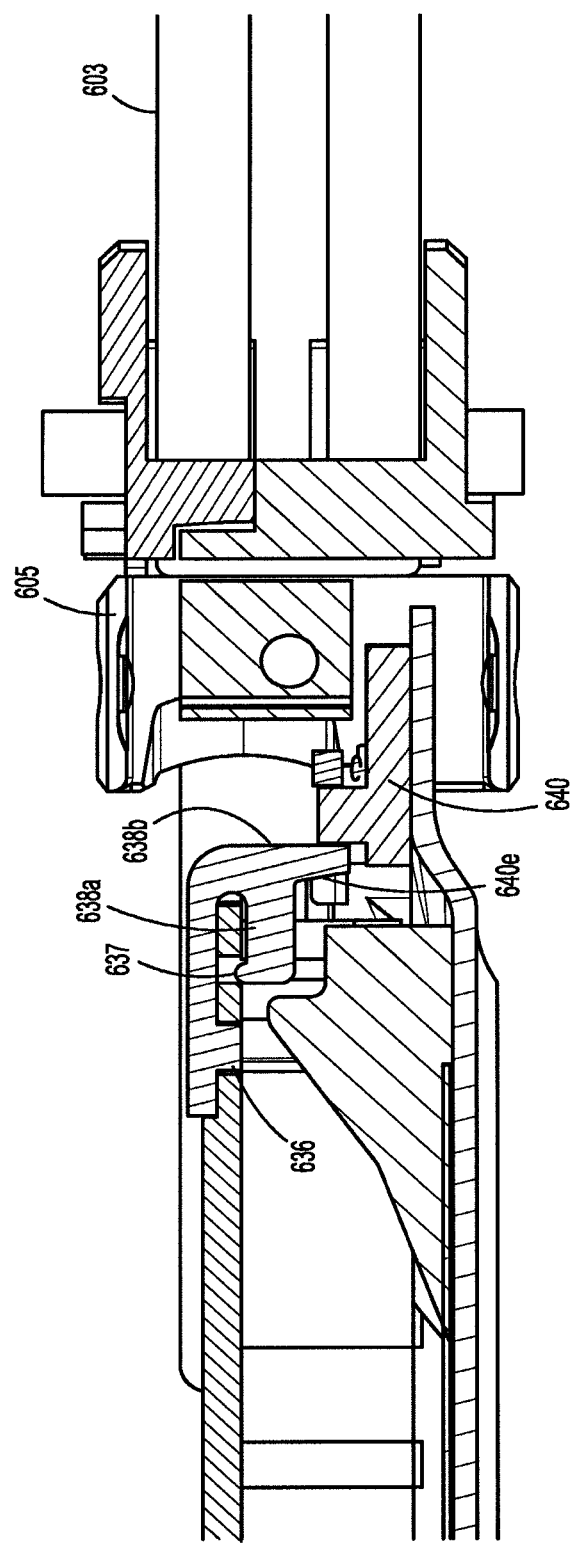
FIG. 86 is a partial, cross sectional view of a distal end of the reload.

Lockout assembly 632 includes locking lever 640, a spring 670 and a mounting member, e.g., a rivet 660, see FIG. 81 for example. Spring 670 may be any suitable type of spring including coil, torsion, etc. In the illustrated embodiment, spring 670 is in the form of a torsion spring and includes two leg members 671a, 671b that are wound and joined to one another to form a central aperture 670a (FIG. 81) of suitable configuration. Central aperture 670a is aligned with an aperture 641 defined through locking member 640 and is configured to receive rivet 660 therethrough to couple locking lever 640 to jaw member 608. Leg portions 671a, 671b are configured to bias locking lever 640 in the locked out configuration. Specifically, one or both of leg portions 671a, 671b (e.g., leg portions 671a) is configured to contact a pivot member 643 that is provided on locking lever 640 to bias locking lever 640 in the locked out configuration (see FIGS. 78, 88, 90 and 92). A top portion 660b of rivet 660 is configured to couple spring 670 and locking lever 640 to one another (FIG. 78).

With reference to FIGS. 82-83, locking lever 640 is illustrated. Locking lever 640 includes a generally rectangular configuration having proximal and distal ends 640a, 640b, respectively. Pivot member 643 extends in a generally orthogonal direction from a top surface 640c of locking member 640 and includes proximal and distal sidewalls 640d, 640e that are joined by a medial sidewall portion 640f. Proximal sidewall 640d includes a generally arcuate configuration and is positioned adjacent top portion 660b of rivet 660 to facilitate rotation of locking lever 640 about rivet 660. Distal sidewall 640e is angled to facilitate contact with post portion 638b of actuator 632 when cartridge 612 is being coupled to jaw member 608.

Figure 90:
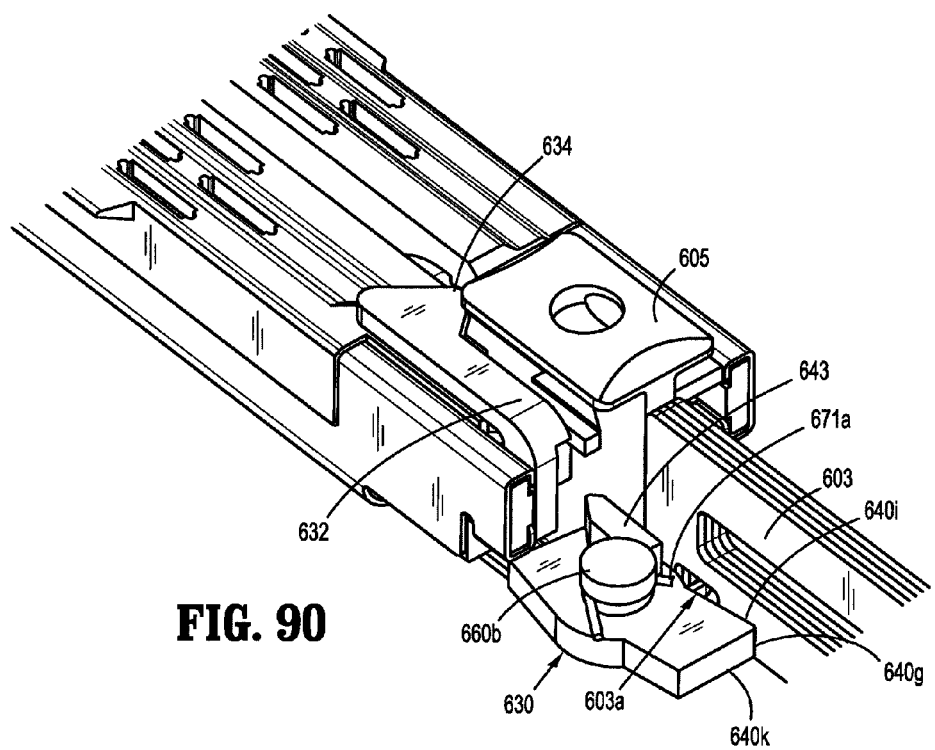
FIG. 90 is a partial, perspective view of the cartridge with parts removed in the pre-fired configuration.
Figure 91:
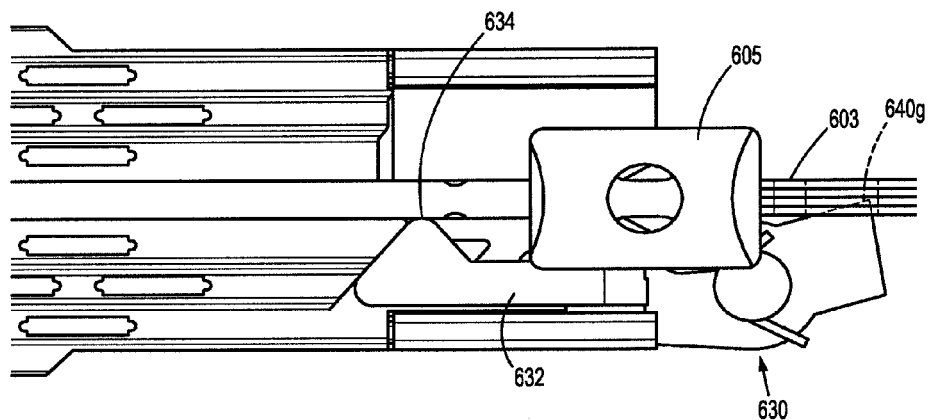
FIG. 91 is a partial, top elevational view of the cartridge with parts removed in a post-fired configuration.
Figure 92:
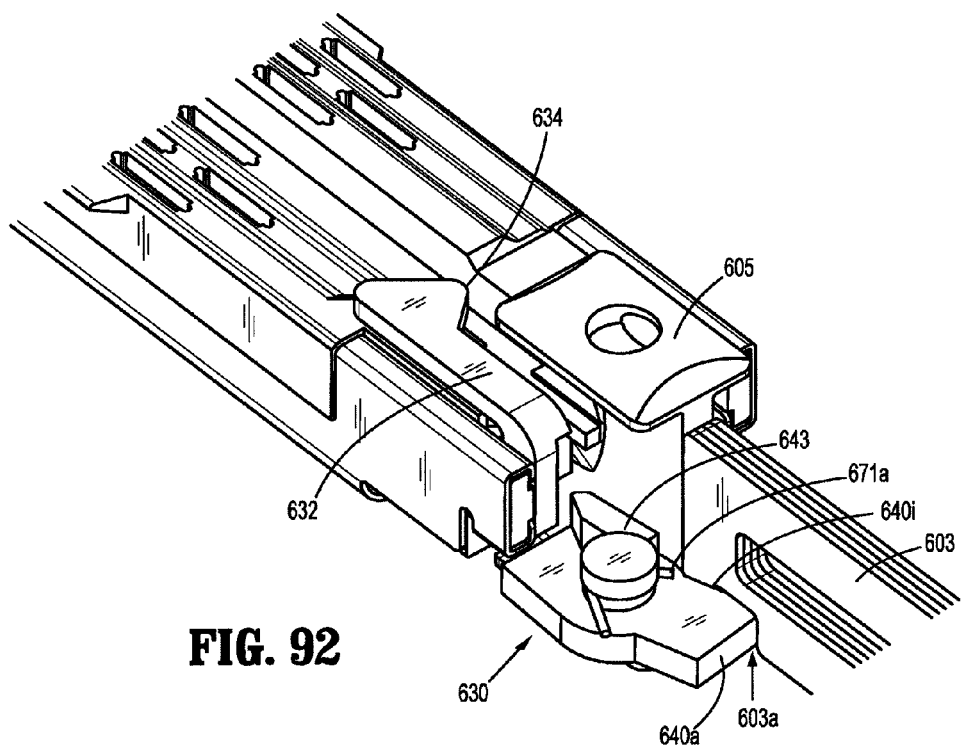
FIG. 92 is a partial, perspective view of the cartridge with parts removed in the post-fired configuration.

Continuing with reference to FIGS. 82-83, top surface 640c extends a predetermined distance from a bottom surface (not explicitly shown) of locking lever 640 so as to allow post portion 638b of actuator 632 to slide along top surface 640c and contact distal wall 640e when cartridge 612 is being coupled to jaw member 608 (FIG. 78). Proximal end 640a includes a proximal wall 640k having a relatively flat configuration and a rounded inside corner portion 640g that is configured to slide along a lower portion of drive beam members 603 as the working end 601 is translated distally and/or proximally (FIG. 90). Proximal wall 640k is configured to selectively engage notch 603a. Corner portion 640g meets an inner sidewall 640i having a proximal and distal sidewall portions 640j, 640h, respectively. Proximal sidewall portion 640j includes a relatively flat configuration and extends distally to meet distal sidewall portion 640h which includes a bowed or concave configuration. This bowed configuration of distal sidewall portion 640h facilitates proximal translation of the working end 601 past locking lever 640 as the working end 601 is moved back to the retracted configuration.

Figure 87:
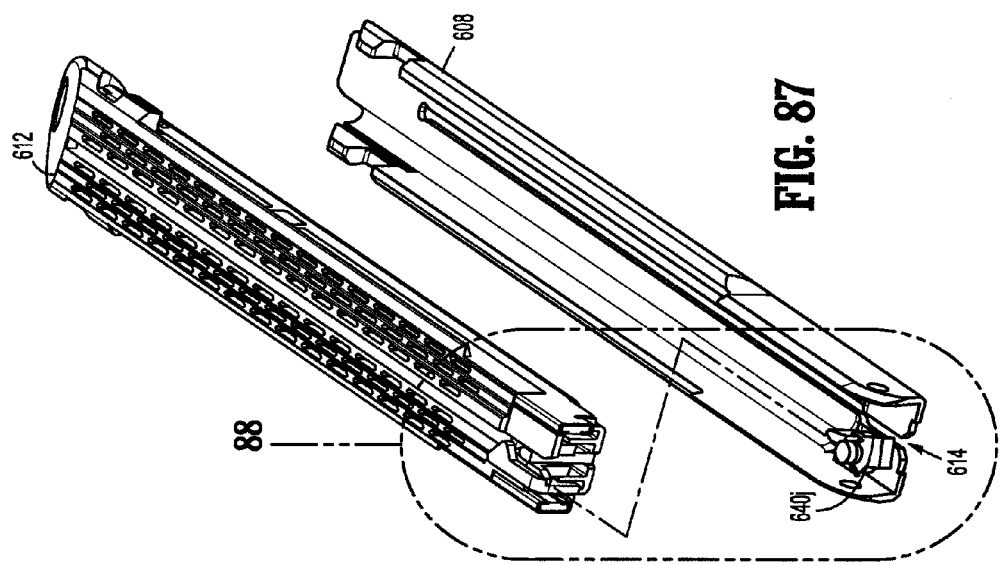
FIG. 87 is a perspective view of the jaw member and cartridge uncoupled from one another.

In use, locking lever 640 is, initially, biased inwardly to the locked out configuration to prevent distal translation of the working end 601 (FIG. 87). Specifically, proximal wall 640k and inner sidewall 640i are positioned adjacent the working end 601 and distal with respect to notch 603a so as to be able to engage notch 603a if the working end 601 is moved a predetermined distance distally (see FIGS. 91-92). That is, locking lever 640 is biased inwardly against the bottom portion of drive beam members 603 so that proximal wall 640k and/or inner sidewall 640i can engage notch 603a as the working end 601 is moved distally.

Figure 88:
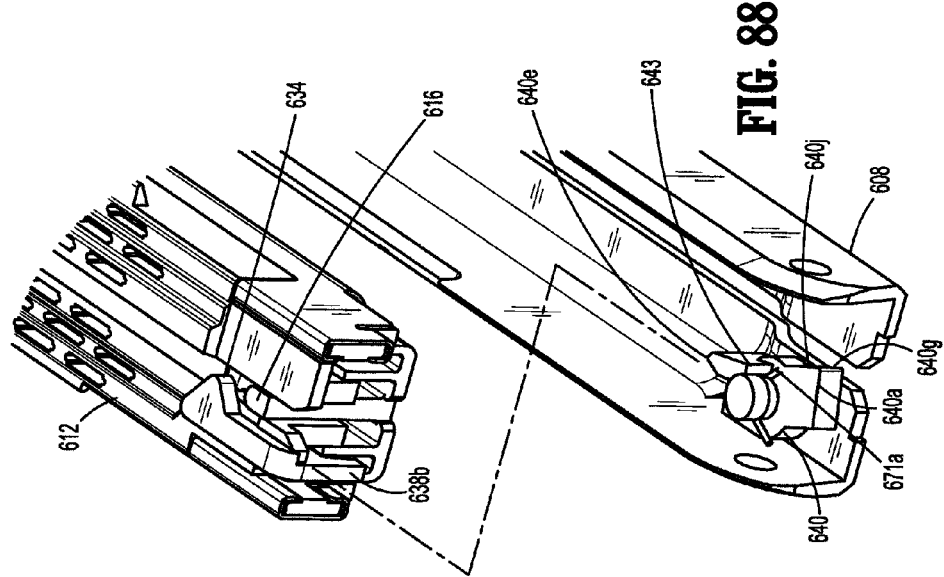
FIG. 88 is an enlarged area of detail of FIG. 87.

Thereafter, cartridge 612 may be coupled to jaw member 608. In doing so, post 638b contacts distal sidewall 640e and pushes pivot member 643 proximally to partially rotate locking lever 640 out of the locked out configuration and away from notch 303a (FIGS. 79-80 and 88).

Figure 89:
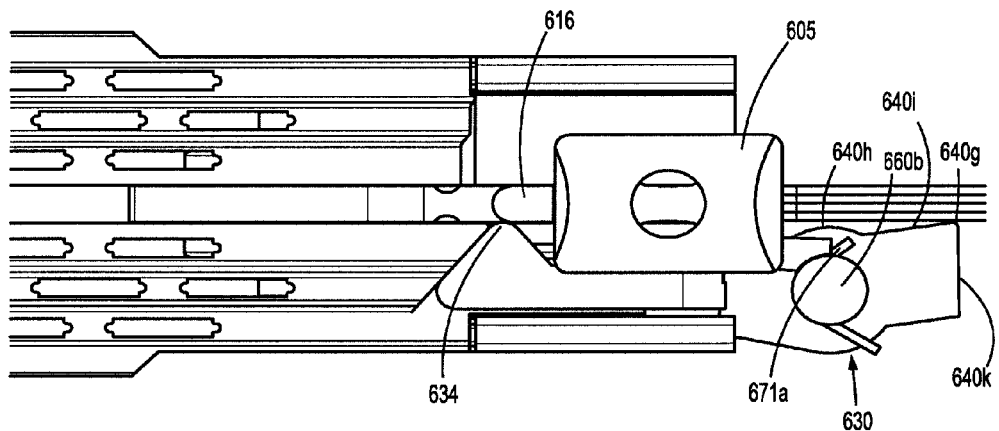
FIG. 89 is a partial, top elevational view of the cartridge with parts removed in a pre-fired configuration.

With locking lever 640 in the pre-fired configuration, the working end 601 including actuation sled 615 may be fired to staple and, subsequently, sever the stapled tissue. When fired, the working end 601 including actuation sled 615 move a predetermined distance distally such that cam feature 616 contacts protuberance 634 so as to pivot actuator 632 about detent 637, which, in turn, causes tab 636 to move inwardly within aperture 622a (FIGS. 89-90). As a result of thereof, post 638b slides across distal sidewall 640e and moves out of contact therewith, which, in turn, causes locking lever 640 to pivot inwardly about rivet 660 and against the bottom portion of drive beam members 603 into the locked out configuration. In accordance with the instant disclosure, at the time cam feature 616 contacts protuberance 634, notch 603a will be positioned distally of inner sidewall 640i so as to allow complete translation of the working end 601 through knife channel 614 (see FIG. 90).

With locking lever 640 in the locked out configuration, the working end 601 may be moved proximally back to the retracted configuration, wherein notch 603a is again positioned proximally with respect to locking lever 640. Once in the retracted configuration, the working end 601 is locked out from translating distally past locking lever 640 while the spent cartridge is attached to jaw member 608.

With reference to FIGS. 93-104, a reload 706 (for illustrative purposes being shown without a shaft coupled thereto) includes a locking mechanism according to an embodiment of the instant disclosure and is configured for use with surgical stapling apparatuses 100, 200 is illustrated.

Figure 93:
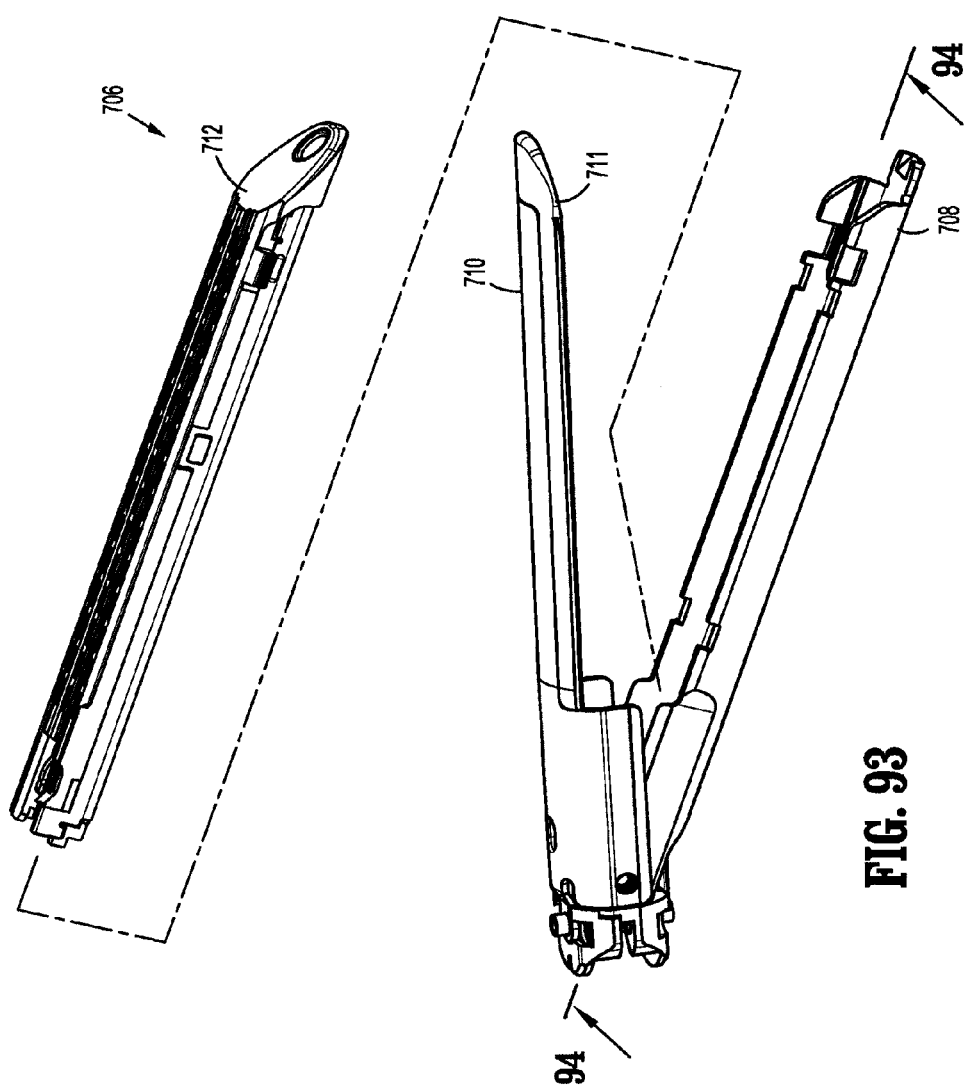
FIG. 93 is a perspective view of a reload with parts removed and including a drive lockout mechanism according to another embodiment of the present disclosure.
Figure 94:
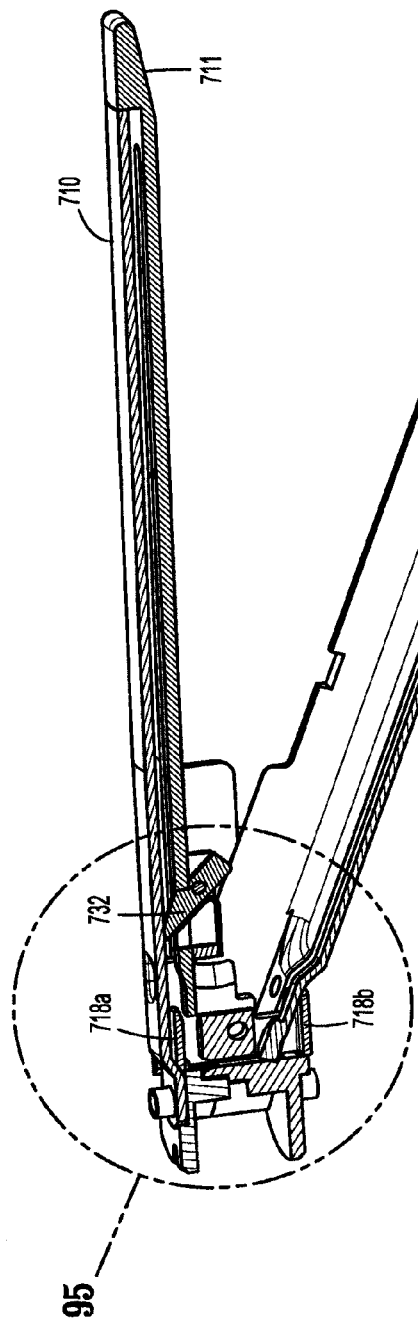
FIG. 94 is a partial, cross-sectional view taken along line section 94-94 shown in FIG. 93.
Figure 95:
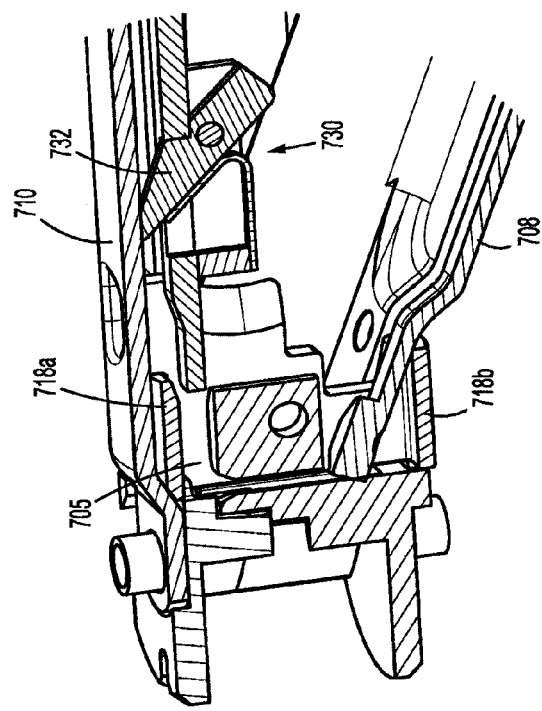
FIG. 95 is an enlarged area of detail of FIG. 94.
Figure 102:
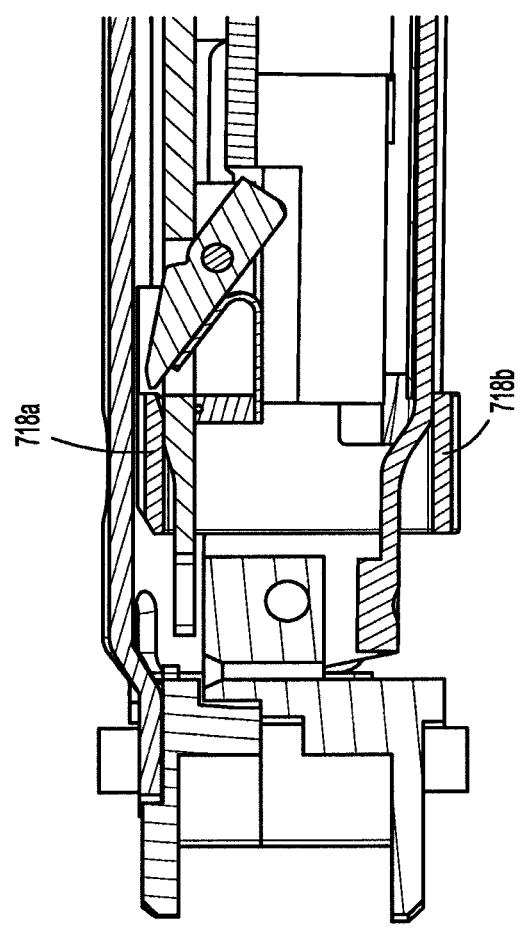
FIG. 102 is a partial, cross-sectional view of the jaw members in an approximated and post-fired configuration with the knife in a retracted configuration.

With reference initially to FIGS. 93-95, a jaw member 710 includes an anvil 711 and is coupled to a jaw member 708 configured to selectively couple to a cartridge 712. An actuation sled 715 is provided in cartridge 712 and includes a central support wedge 713. When cartridge 712 is coupled to jaw member 708, and jaw members 708, 710 are in an approximated configuration, central support wedge 713 is configured to contact a pawl 732 of a lock out assembly 730 that is operably coupled to jaw member 710 (see FIG. 100).

Referring to FIG. 96, jaw member 710 includes a proximal end 710a that is configured to cover a proximal end 711a of anvil 710. In an assembled configuration, proximal end 710a extends a predetermined distance from proximal end 711a of anvil so as to allow pawl 732 to pivot through a knife channel 714 defined through anvil 711. Knife channel 714 extends along a length of anvil 711 and is configured to receive a top flange 718a of knife 705 so as to allow proximal and distal translation of the working end 701. Similarly, a bottom flange 718b of knife 705 is provided through a knife channel (not explicitly shown) that extends through a bottom surface of jaw member 708 (see knife channel 614 above for example).

With reference to FIG. 97, lock out assembly 730 is configured to lock out the working end 701 to prevent misfiring thereof prior to coupling cartridge 712 to jaw member 708, and subsequent to coupling cartridge 712 and firing knife 708, i.e., when cartridge 712 is spent. Lock out assembly 730 includes a bracket 731 of suitable configuration that operably couples to an inner surface (not explicitly shown) of jaw member 710. In the illustrated embodiment, a pivot pin 733, rivet or the like may be utilized to mount bracket 731 to the inner surface of jaw member 710. Alternatively, bracket may be coupled to the inner surface of jaw member 710 via welding (e.g., laser beam or electron beam welding), ultrasonic welding, brazing, soldering or other suitable device or method. Bracket 731 includes a bifurcated configuration having a closed proximal end 731a and an open distal end 731b that is defined by two elongated fingers 734a, 734b that are spaced apart a predetermined distance from one another. Specifically, fingers 734a, 734b are spaced apart from one another a distance that allows pawl 732 to pivot unobstructed between fingers 734a, 734b. In embodiments, distal end 731b may be closed.

With continued reference to FIG. 97, pivot pin 733 extends through a pair of apertures 736 that are defined through fingers 734a, 734, and is coupled to the inner surface of jaw member 710 via one or more suitable coupling methods, e.g., laser beam or electron beam welding. Pivot pin 733 is also positioned through an aperture 738 of suitable configuration that is defined through pawl 732. Pivot pin 733 is operable to allow pawl 732 to pivot thereabout when pawl 732 is contacted by central wedge 713. Pivot pin 733 is positioned distally with respect to resilient member 760 that is provided on bracket 731.

Resilient member 760 may be any suitable resilient member. In the illustrated embodiment, for example, resilient member 760 is formed from a relatively resilient strip of plastic material that has been bent to form a generally "U" shape (FIG. 97). Resilient member 760 is operable to pivot pawl 732 about pivot pin 733. Accordingly, resilient member 760 includes a base portion 761 that couples via one or more suitable coupling methods, e.g., laser beam or electron beam welding, to a bottom surface 731c that extends from proximal end 731a and along fingers 734a, 734b. Base portion 761 meets an arcuate medial portion 762 that serves as a living hinge that meets a flexure portion 763 that couples to pawl 732. Flexure portion 763 provides an upwards biasing force that urges pawl 732 through knife channel 714 when cartridge 712 is not coupled to jaw member 708 (see FIGS. 94-95) and after the working end 701 has been fired (FIGS. 100-101) and moved back to the retracted configuration (see FIG. 102). Moreover, flexure portion 763 flexes about medial portion 762 when pawl 732 is contacted by central wedge 713 (FIGS. 100-101). Coupling base portion 761 along the bottom surface 731c prevents base portion 761 from moving as pawl 732 pivots about pivot pin 733 and flexure portion 763 flexes about medial portion 762.

Continuing with reference to FIG. 97, pawl 732 may be formed from any suitable material including but not limited to metal, plastic, ceramic, etc. In the illustrated embodiment, pawl 732 is formed from metal. Pawl 732 includes a generally elongated configuration having proximal and distal portions 732a, 732b with a generally arcuate recess 732c therebetween. Proximal portion 732a includes a generally rectangular configuration and distal portion 732b extends distally from arcuate recess 732c so as to form a distal tip 732d. A bottom surface 732e of pawl 732 is configured to contact central wedge 713 when cartridge 712 is coupled to jaw member 708.

In use, pawl 732 is, initially, biased upwardly via flexure portion 762 to the locked out configuration to prevent distal translation of the working end 701 (FIGS. 94-95). Thereafter, cartridge 712 may be coupled to jaw member 708. In doing so, central wedge 713 contacts bottom surface 732e of pawl 732 which causes pawl 732 to pivot about pivot pin 733, which, in turn, causes distal tip 732d, against the biasing force of flexure portion 762, to move from within knife channel 714 (FIGS. 98-100).

With pawl 732 in the pre-fired configuration, the working end 701 including actuation sled 715 may be fired to staple and, subsequently, sever the stapled tissue. When fired, the working end 701 including actuation sled 715 move distally and, thus, central wedge 713 moves out of contact with bottom surface 732e (FIGS. 89-90). As a result of thereof, pawl 732 is biased upwardly via flexure portion 762 to the lock out configuration.

With pawl 732 in the locked out configuration, the working end 701 may be moved proximally back to the retracted configuration. As the working end 701 is being moved proximally to the retracted configuration, top flange 718a contacts distal end 732b then distal tip 732d, which, in turn, causes pawl 732 to pivot downwardly about pivot pin 733. Once in the retracted configuration, the working end 701 is locked out from translating distally past pawl 732 while the spent cartridge is still attached to jaw member 708 (see FIG. 102).

Figure 103:
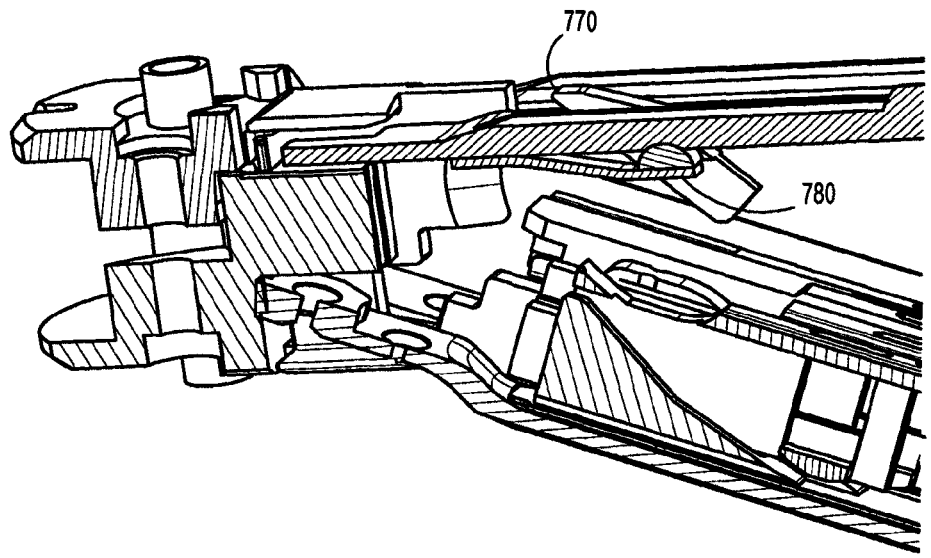
FIG. 103 is a partial, cross-sectional view of reload including a drive lockout mechanism according to another embodiment of the present disclosure.
Figure 104:
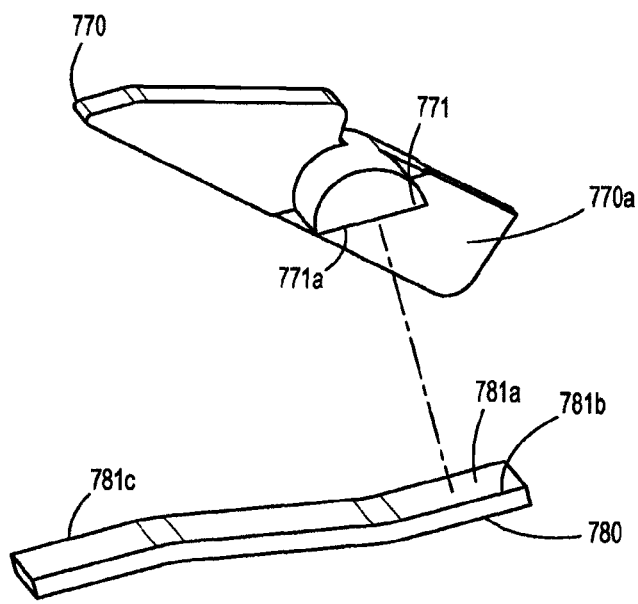
FIG. 104 is an exploded view of a pawl of an anvil with parts separated.
Figures 107, 108:
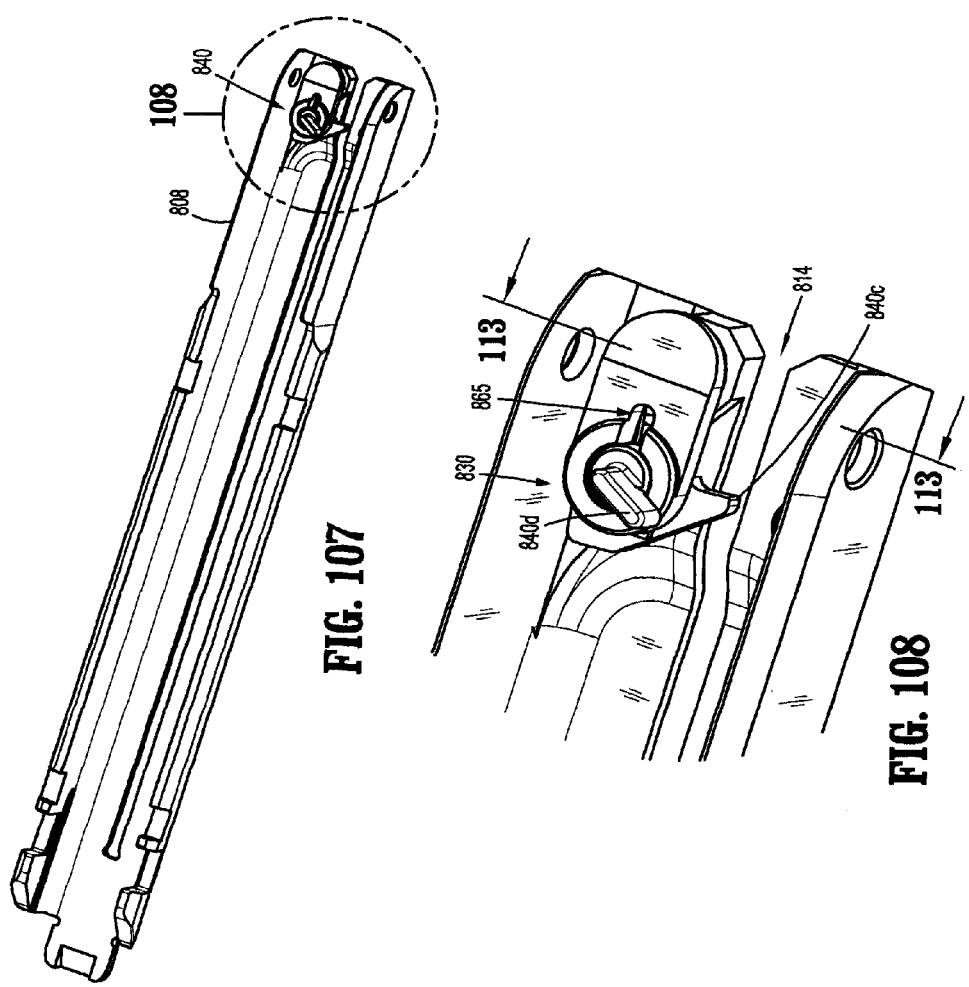
FIG. 107 is a perspective view of a jaw member depicted in FIG. 105.
FIG. 108 is an enlarged area of detail of FIG. 107.

With reference to FIGS. 103-104, a pawl 770 and resilient member 780 may be utilized instead of pawl 732 and resilient member 760. In this embodiment, pivot pin 733 is not utilized. Rather, a generally hemispherical protrusion 771 may extend from either side or both sides of pawl 770. For illustrative purposes, one protrusion 771 is shown extending from a left sidewall 770a of pawl 770.

A relatively flat bottom surface 771a is provided on protrusion 771 and is coupled to a top surface 781a of resilient member 780, e.g., a leaf spring, adjacent a proximal portion 781b thereof. Top surface 781a at a distal portion 781c of resilient member 780 is coupled to an inner top surface of jaw member 710 and a medial portion 781d is configured to flex when central wedge 713 contacts pawl 770. Pawl 770 is functionally the same as pawl 732; therefore, a detailed description of operation of pawl 770 is not described herein.

With reference to FIGS. 105-127, a reload 806 includes a locking mechanism according to an embodiment of the instant disclosure and is configured for use with surgical stapling apparatuses 100, 200 is illustrated.

Figure 109:
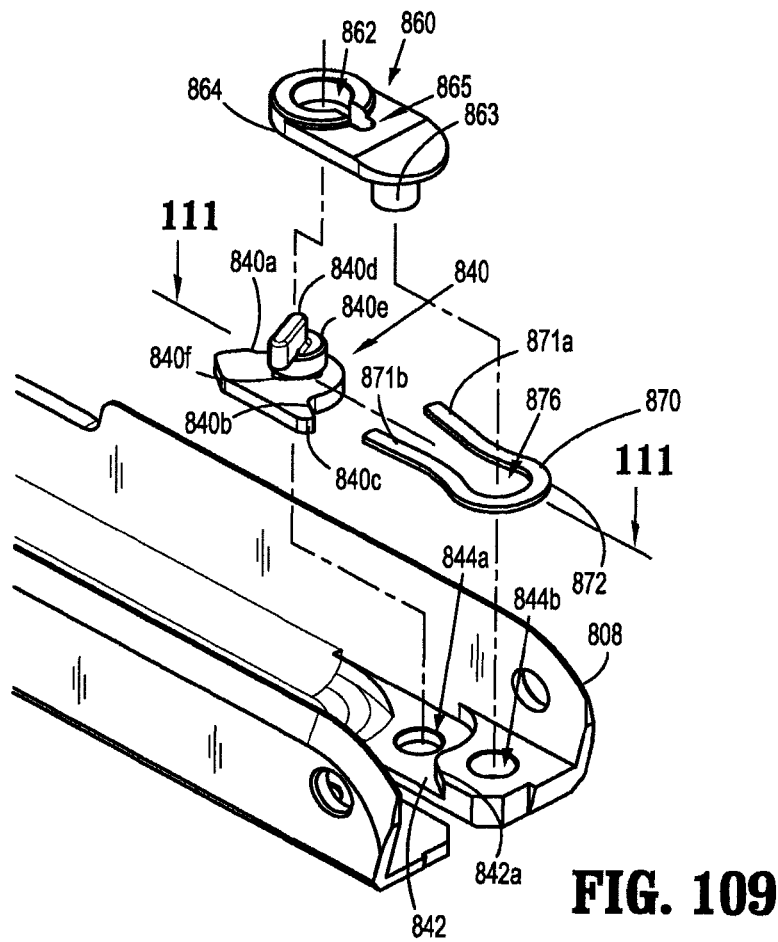
FIG. 109 is a proximal end of the jaw member depicted in FIG. 107 with parts separated.
Figure 110:
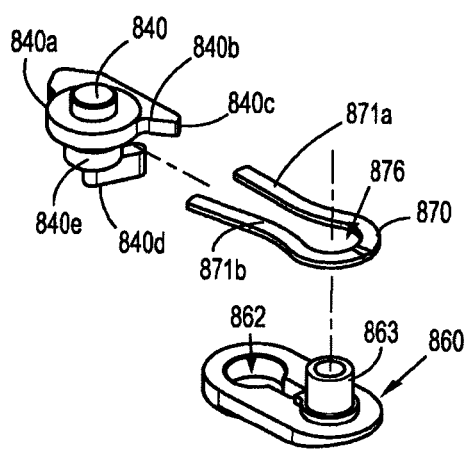
FIG. 110 is an exploded view of a lock out assembly associated with the reload depicted in FIG. 105 with parts separated.

With reference initially to FIGS. 105-113, reload 806 includes a lockout assembly 830 which is similar to lockout assembly 530. Specifically, lockout assembly 830 is operably positioned at a proximal end of jaw member 808 and located distal of the pivot assembly (FIGS. 105-108); only a portion of the pivot assembly coupled to jaw member 808 is illustrated in the Figs. As with lockout assembly 530, lockout assembly 830 is configured to lock out knife 808 (FIG. 106) when a cartridge 812 is not coupled to jaw member 808 or when a spent cartridge 812 is coupled to jaw member 808. To this end, lockout assembly 830 includes three main components, a locking lever 840, a mounting member 860 and a spring clip 870 (FIGS. 109-110).

Continuing with reference to FIGS. 109-110, locking lever 840 includes a base portion 840a of suitable configuration that is configured to seat within a recess 842 provided at a proximal end of jaw member 808. A bottom surface of base portion 840a is provided with a generally circumferential protuberance 840f that is configured to be received within a corresponding aperture 844a that is provided within recess 842 and defined through a bottom wall portion of jaw member 808. In an assembled configuration, protuberance 840f is configured to allow rotation of locking lever 840 within recess 842; in this embodiment, however, rotation is a result of contact with an inwardly extending detent 831 that is provided on an actuator 832 (see FIG. 119).

A generally arcuate cutout 840b is provided on base portion 840a and includes a tip 840c configured to contact a corresponding sidewall 842a that helps define recess 842 (see FIG. 109). Unlike locking lever 540, however, which includes a boss 540d, a latch 840d (FIGS. 109-110) of suitable configuration is provided on a protrusion 840e (which extends from base portion 840a) and is configured to contact detent 831. Specifically, when cartridge 812 is coupled to jaw member 808, detent 831 of actuator 832 contacts latch 840d and rotates locking lever 840 until latch 840d contacts a trailing edge 864 of mounting member 860 and tip 840c contacts sidewall 842a of recess 842 (see FIGS. 123-125).

Figure 111:
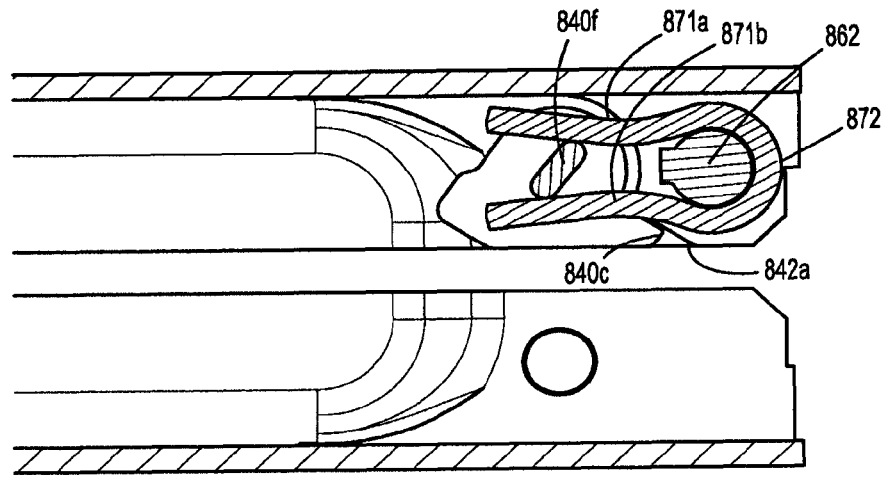
FIG. 111 is a partial, top cross sectional view of a jaw member with the locking member in an unlocked configuration.
Figure 112:
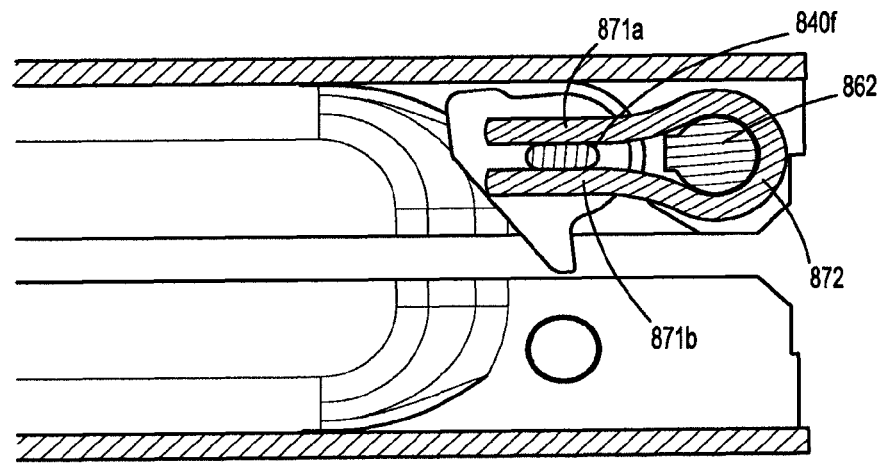
FIG. 112 is a partial, top cross sectional view of a jaw member with the locking member in a locked configuration.
Figure 113:
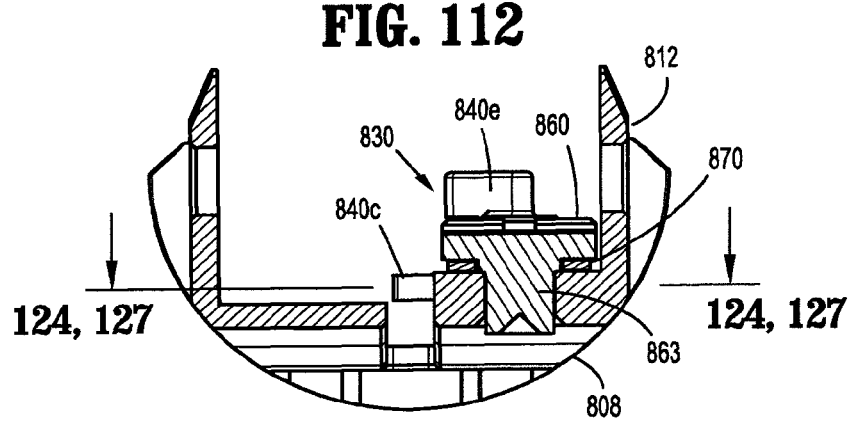
FIG. 113 is a cut-away view taken along line section 113-113 shown in FIG. 112.
Figure 114:
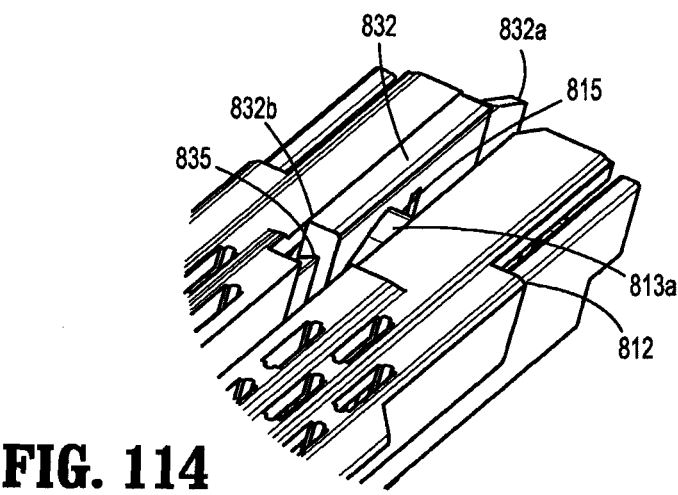
FIG. 114 is a partial, front perspective view of a proximal end of a cartridge configured for use with the reload depicted in FIG. 105.

Protrusion 840e is provided on base portion 840a and is supported by a post 840f that extends from base portion 840a (FIGS. 109-112). Protrusion 840e includes a generally circumferential configuration and is configured to rotatably engage a corresponding opening 862 provided on mounting member 860 for securing locking lever 840 within recess 842. Post 840f includes a generally oblong configuration and is configured to be received between spaced-apart leg portions 871a, 871b of spring clip 870 (as best seen in FIGS. 111-112) so as to allow rotation thereof including locking lever 840 within aperture 844a. Specifically, leg portions 871a, 871b are configured to bias post 840f and, thus, locking lever 840 into a locked out configuration. More specifically, when cartridge 812 is coupled to jaw member 808, detent 831 contacts latch 840d and urges latch 840d proximally, which, in turn, partially rotates post 840f into contact with and against the biasing force provided by leg portions 871a, 871b (FIG. 111). In the locked out configuration, the biasing force provided by leg portions 871a, 871b on post 840f prevents the working end 801 from moving past tip portion 840c. That is, the biasing force provided by leg portions 871a, 871b on post 840f is greater than the force utilized to fire and/or translate the working end 801 distally and, therefore, leg portions 871a, 871b do not move apart from one another as a result of contact between the working end 801 and tip portion 840c as the working end 801 is moved distally.

Leg portions 871a, 871b meet at a generally arcuate proximal end 872 of spring clip 870 (FIG. 109-112). The arcuate configuration of proximal end 872 provides a suitable spring constant and is configured to allow leg portions 871a, 871b flex or move a predetermined distance away from one another when post 840f contacts leg portions 871a, 871b. An aperture 876 (FIGS. 109-110) of suitable configuration is provided adjacent proximal end 872 and is configured to receive therethrough a corresponding protrusion 863 that is provided on a bottom surface of mounting member 860 (FIGS. 109-110).

Mounting member 860 includes a generally elongated configuration having opening 862 at a distal end thereof and protrusion 863 at a proximal end thereof to mount locking lever 840 to jaw member 808 (FIG. 109). Specifically, protrusion 840e is positioned within aperture 862 and protrusion 863 is positioned through aperture 876 and through an aperture 844b provided within recess 842 adjacent aperture 844a (see FIG. 109). A slit 865 having a complementary configuration to latch 840d is provided on mounting member 860 adjacent aperture 862 and is configured to accommodate reception of latch 840d therethrough; alignment of latch 840d with slit 865 enables protrusion 840e to be positioned through aperture 862.

Figure 115:
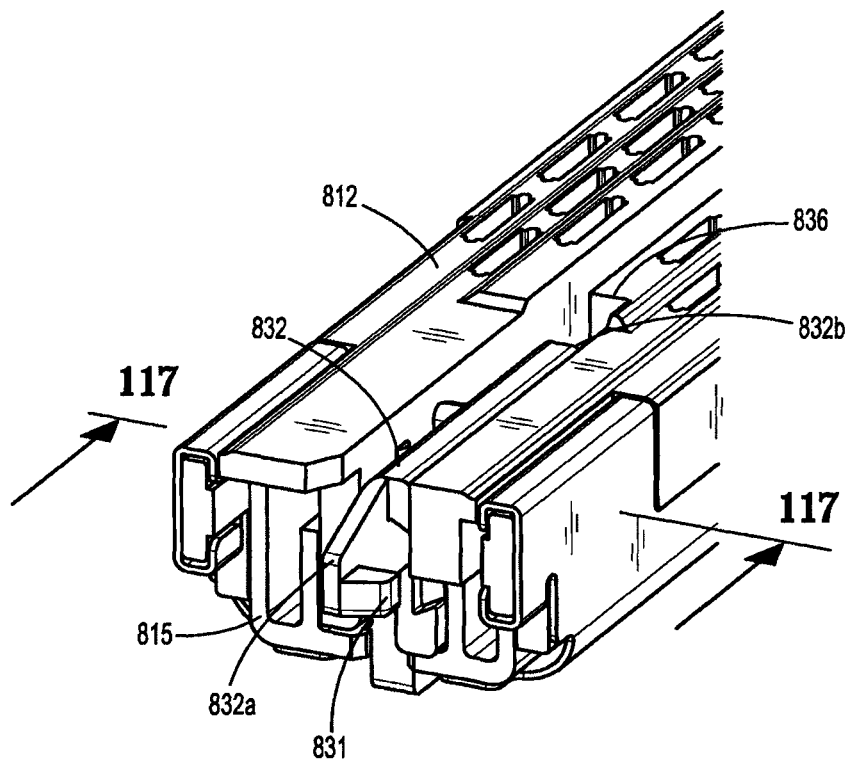
FIG. 115 is a partial, back perspective view of proximal end of the cartridge depicted in FIG. 114.
Figure 116:
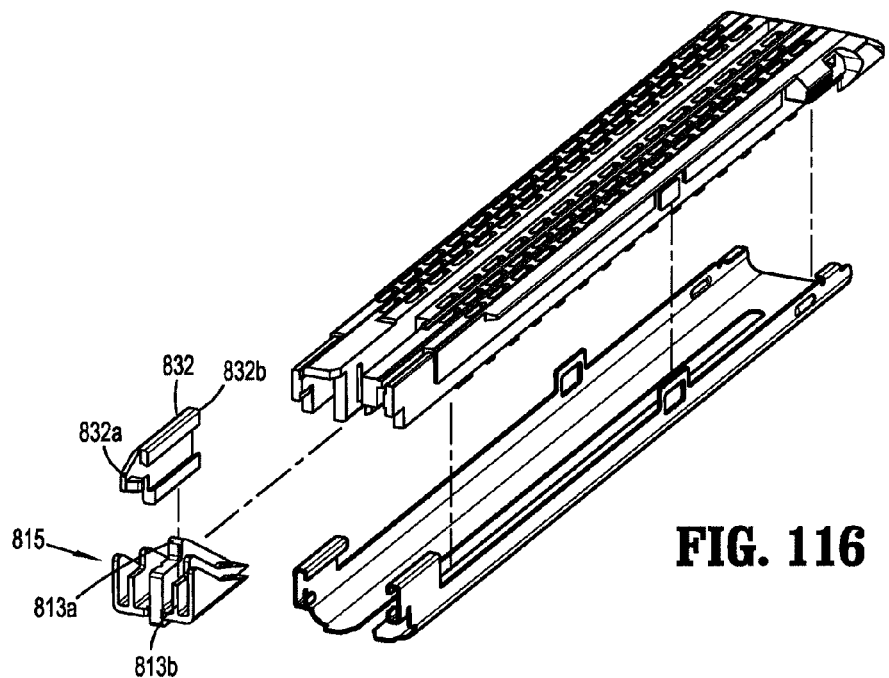
FIG. 116 is an exploded view of the cartridge with parts separated.
Figure 122:
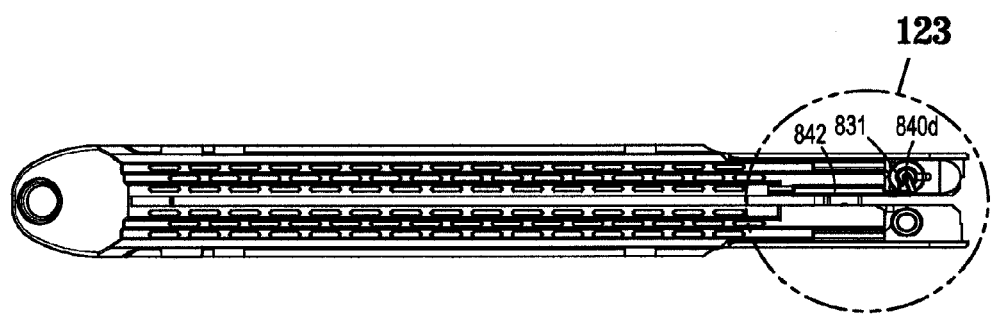
Figure 123:
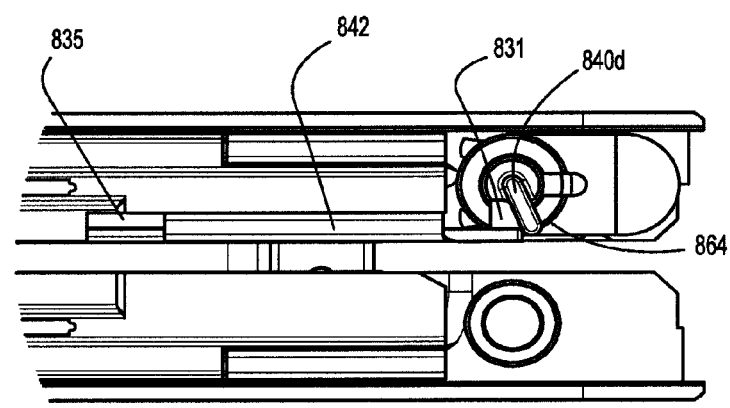
Figure 124:
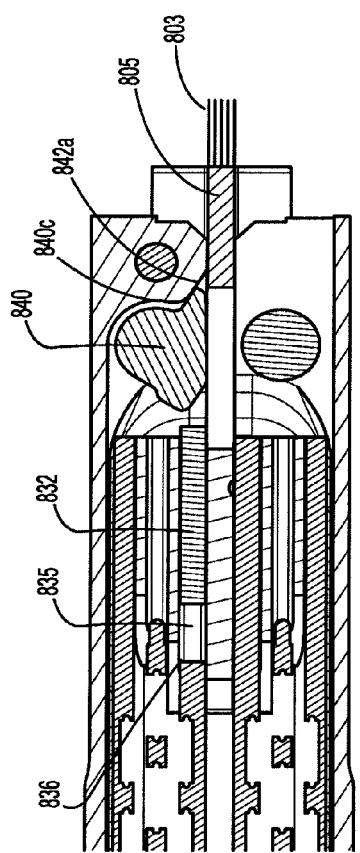
Figure 125:
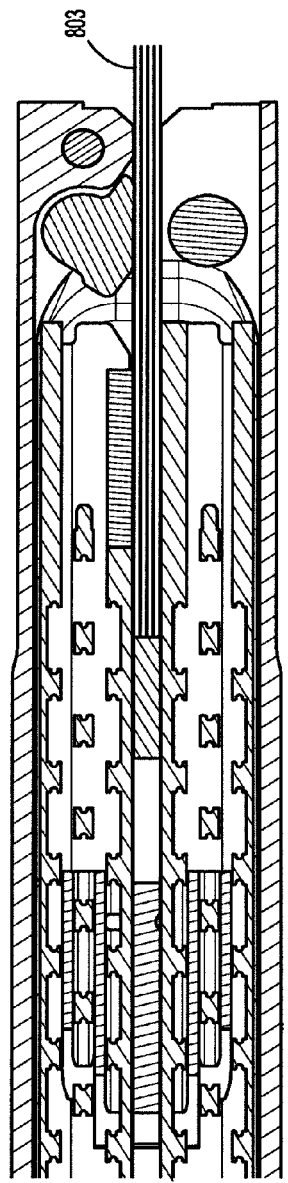

Turning now to FIGS. 114-123, actuator 832 is provided at a proximal end of cartridge 812 (FIG. 114) and is configured to selectively disengage lockout assembly 830 from the locked out configuration to allow firing of the working end 801 (FIG. 123). Actuator 832 may be formed from any suitable material including but not limited to metal, plastic, etc. In the illustrated embodiment, actuator 832 is formed from a relatively rigid plastic material and includes a generally elongated configuration having proximal and distal ends 832a, 832b, respectively (FIG. 115).

Referring to FIGS. 116-119, actuator 832 is positioned between a central support wedge member 813a and side wedge member 813b that is positioned to the right of central support wedge member 813a. Actuator 832 is configured to translate a predetermined distance distally within cartridge 812 as actuation sled 815 is moved through cartridge 812 to eject the plurality of fasteners (not shown). In accordance therewith, actuator 832 releasably couples to actuation sled 815 via one or more suitable coupling method. In the illustrated embodiment, for example, an indent/detent configuration is utilized to releasably couple actuator 832 and actuation sled 815 to one another. Specifically, an indent 833a of suitable configuration is provided on a bottom surface 832c of actuator 832 and is configured to releasably couple to a corresponding detent 833b that is provided in between central support wedge 813a and wedge 813b (see FIGS. 119-121).

Figure 117:
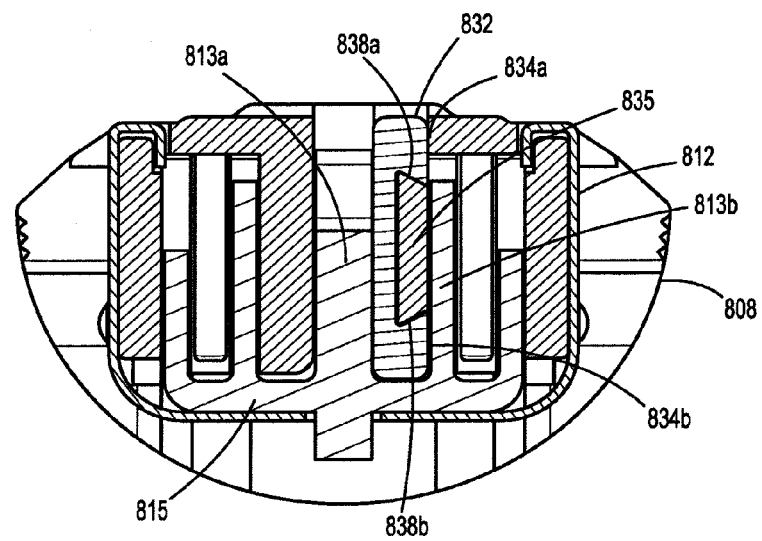
FIG. 117 is a cut-away view taken along line section 117-117 shown in FIG. 115.
Figure 118:
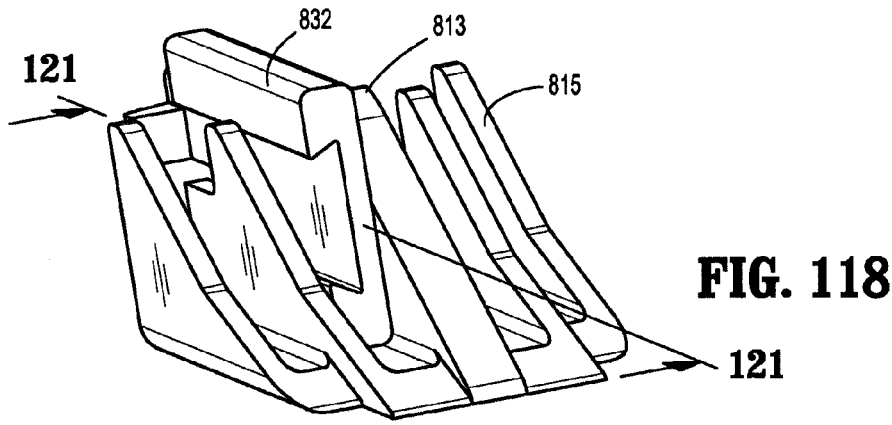
FIG. 118 is a perspective view of an actuation sled associated with the cartridge having an actuator coupled thereto.
Figure 119:
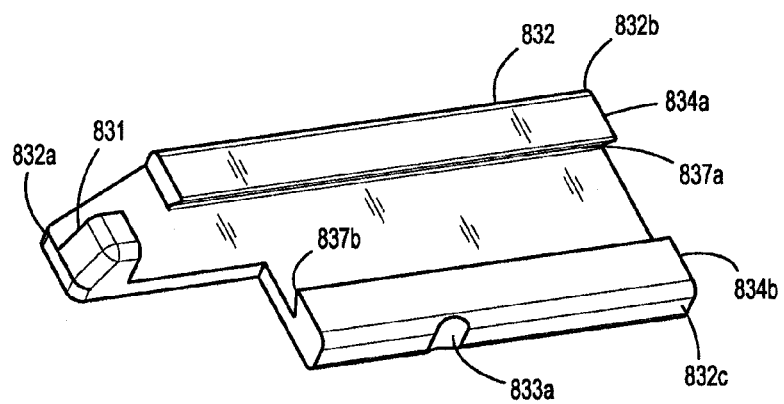
Figure 120:
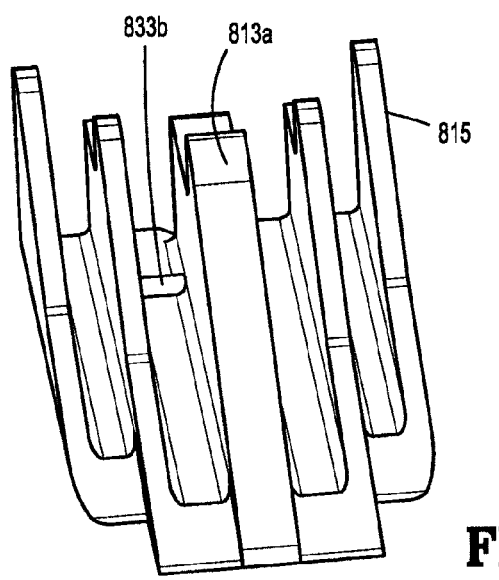
Figure 121:
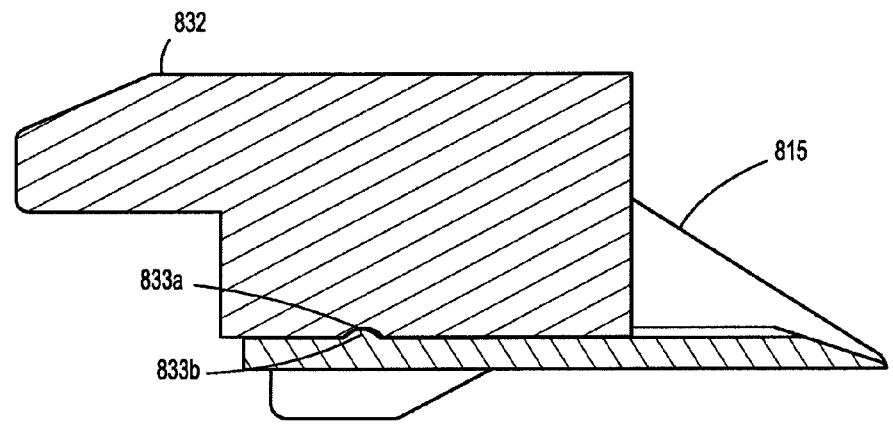

Actuator 832 includes a pair of generally elongated sidewalls 834a, 834b that extend a predetermined length along actuator 832 (FIG. 119). Sidewalls 834a, 834b are spaced apart from one another to receive therein a corresponding stop member 835 of suitable configuration that is provided an interior sidewall 836 within cartridge 812, see FIG. 115 in combination with 117. Interior sidewall 836 including stop member 835 are positioned within cartridge 812 so as to allow distal translation of actuation sled 815 through cartridge 812. Each of sidewalls 834a, 834b includes a respective groove 837a, 837b that is configured to engage corresponding top and bottom projections 838a, 838b of stop member 835 to form a dovetail joint, as best seen in FIG. 117. In accordance with the instant disclosure, when actuation sled 815 translates a predetermined distance past interior sidewall 836, distal end 832b of actuator 832 contacts interior sidewall 836 and grooves 837a, 837b engage top and bottom projections 838a, 838b to prevent distal translation of actuator 832 past interior sidewall 836. Moreover, with grooves 837a, 837b engaged with top and bottom projections 838a, 838b, actuator 832 is secured and prevented from moving within cartridge 812. It should be noted that detent 833*b* is configured to disengage from indent 833*a* after such time that actuator 832 is secured to stop member 835.

Figure 127:
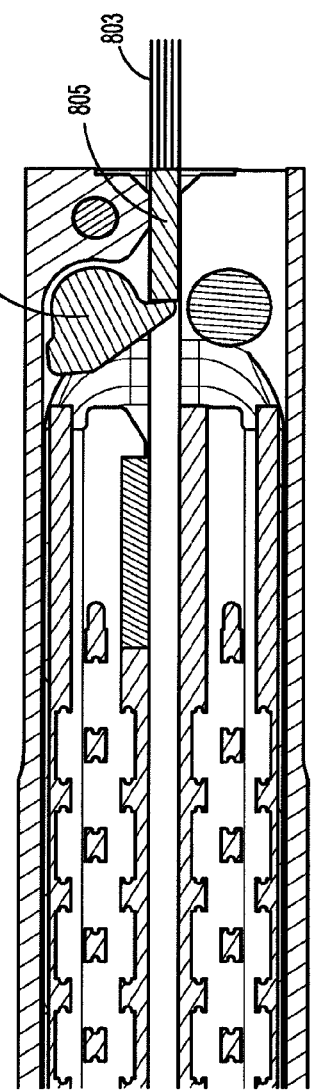

Detent 831 is provided at proximal end 832*a* and extends a predetermined distance inwardly therefrom to move latch 840*d* of lockout assembly 830 into a pre-fired configuration when cartridge 812 is coupled to jaw member 808, see FIGS. 122-123. Detent 831 may be angled (as in the instant embodiment) or otherwise configured to facilitate contact with latch 840*d* (FIG. 123). When detent 831 moves out of contact with latch 840*d*, tip 840*c* is urged into contact with and slides against a bottom portion (not explicitly shown) of drive beam members 803 (FIGS. 124-125 and 127) until such time that the working end 801 is moved proximally past tip 840*c* and back to the retracted configuration (as best seen in FIG. 127). Once the working end 801 is moved to the retracted configuration, tip 840*c* of locking member 840 is moved back to the locked out configuration. The biasing force provided by leg portions 871*a*, 871*b* on post 840*f* prevents the working end 801 from moving past tip portion 840*c*. That is, the biasing force provided by leg portions 871*a*, 871*b* on post 840*f* is greater than the force utilized to fire and/or translate the working end 801 distally and, therefore, leg portions 871*a*, 871*b* do not move apart from one another as a result of contact between the working end 801 and tip portion 840*c* as the working end 801 is moved distally.

In use, locking lever 840 is, initially, in a locked out configuration with tip 840*c* positioned across the knife channel 814 to prevent distal translation of the working end 501 (FIGS. 106-108 and 112). Thereafter, cartridge 812 may be coupled to jaw member 808. In doing so, detent 831 contacts and latch 840*d* proximally to partially rotate locking lever 840 within recess 842. Locking lever 840 rotates within recess 842 until latch 840*d* contacts trailing edge 864 and tip portion 840*c* contacts sidewall 842*a* (FIGS. 111 and 122-123). At this time, post 840*f* moves leg portions 871*a*, 871*b* away from one another and is biased by the force provided therefrom (FIG. 111 for example).

Figure 126:
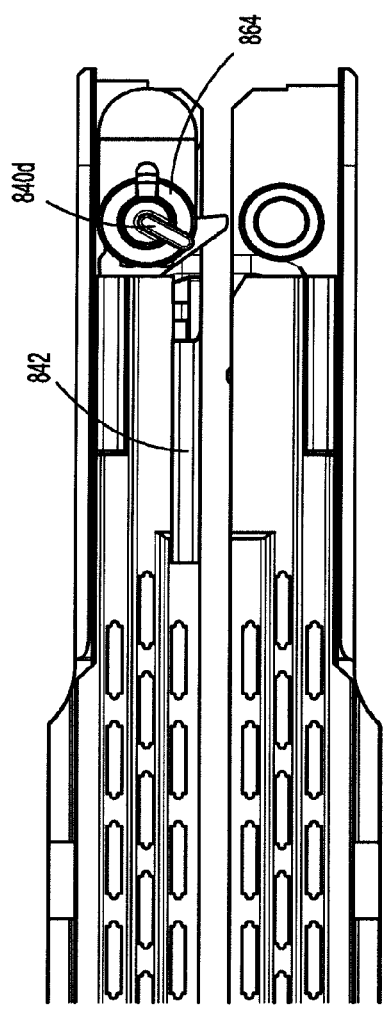

With locking lever 840 and actuator 832 in the pre-fired configuration, the working end 801 including actuation sled 815 may be fired to staple and, subsequently, sever the stapled tissue. When fired, the working end 801 including actuation sled 815 and actuator 832 coupled thereto move distally, which results in actuator 832 contacting stop member 835 in a manner as described hereinabove. Distal translation of actuator 832 causes detent 831 to disengage from latch 840*d* and allows locking lever 840 to move back to the locked-out configuration (FIGS. 126-127). Specifically, when the working end 801 is moved proximally past locking lever 840 to the retracted configuration, locking lever 840 against the bias of spring clip 870 is moved back to the locked out configuration. Once in the retracted configuration, the working end 801 is locked out from translating distally past tip portion 840*c* as a result of the biasing force provided on post 840*f* by leg portions 871*a*, 871*b*.

With reference to FIGS. 128-133, a reload 1006 includes a locking mechanism according to an embodiment of the instant disclosure and is configured for use with surgical stapling apparatuses 100, 200 is illustrated.

Figure 130:
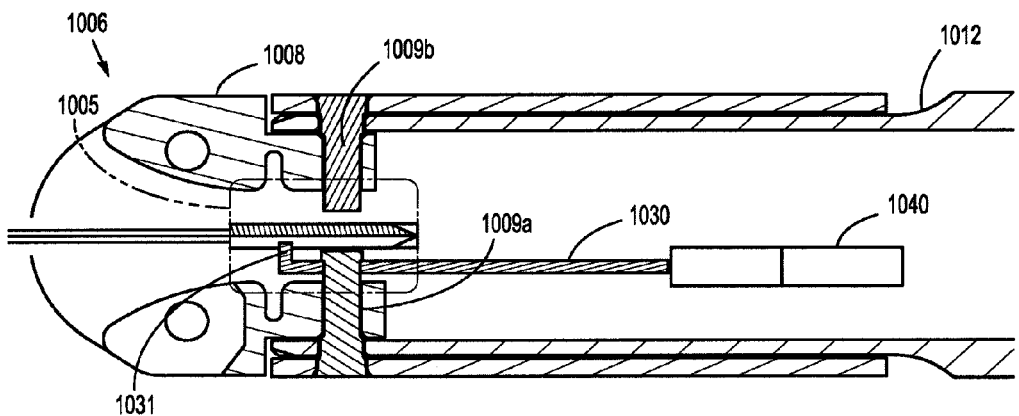

FIG. 130 illustrates a cartridge 1012 installed on a jaw member 1008 with the working end 1001 in a locked out configuration. Unlike the previously disclosed knives, knife 1005 includes a slot 1005*a* of suitable configuration that is defined by respective upper and lower interior walls 1005*c*, 1005*d* and is positioned adjacent a bottom flange 1018*a*. Slot 1005*a* extends horizontally across knife 1005 (FIG. 133) such that knife 1005 can engage and/or disengage from a locking lever 1030 (FIG. 132) and move from a retracted configuration to an extended configuration. A notch 1005*b* of suitable configuration is defined through lower interior wall 1005*d* and is configured to selectively engage a corresponding lateral extension 1031 that is provided on locking lever 1030 to lock out knife 1005 and prevent misfiring thereof (see FIGS. 128 and 132-133). Slot 1005*a* including notch 1005*b* may be formed via one or more suitable processes, e.g., etching or milling process, during a manufacturing process of knife 1005.

With reference to FIG. 132, locking lever 1030 is illustrated including a generally elongated configuration including proximal and distal ends 1030*a*, 1030*b*, respectively. An aperture 1032 of suitable configuration is provided adjacent proximal end 1030*a* and is configured to couple to a rivet 1009*a* that is configured along with an opposing rivet 1009*b* to couple jaw members 1008 and 1010 to one another (FIG. 130). Locking lever 1030 pivots about rivet 1009*a* so as to allow lateral extension 1031 to selectively engage with and disengage from notch 1005*b* (see FIGS. 128-129). A spring (not shown) operably couples to locking lever 1030 and is utilized to bias distal end 1030*b* of locking lever 1030 downwardly and into contact with a blocking member 1040 (FIGS. 128-130).

Blocking member 1040 is provided at a proximal end of an actuation sled (not shown) of the cartridge (not shown) and includes a slanted proximal end 1040*a* that is configured to engage the distal end 1030*b* of the locking lever 1030 when the cartridge is coupled to the jaw member. When the proximal end 1040*a* of the blocking member 1040 engages the distal end 1030*b* of the locking lever 1030, the locking lever 1030 moves downwardly and the lateral extension 1031 moves out of engagement with the notch 1005*b* which allows the working end 1001 to advance through the cartridge.

Figure 128:
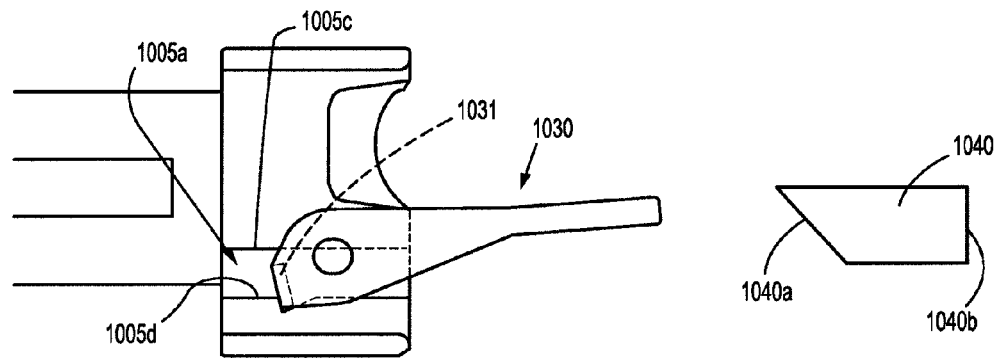
Figure 129:
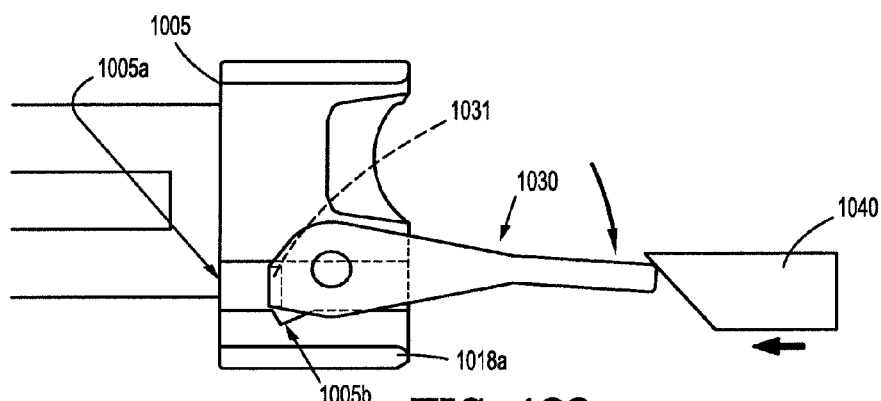

In use, locking lever 1030 is, initially, in a locked out configuration with lateral extension 1031 positioned within the notch 1005*b* of the knife 1005 to prevent distal translation of the working end 1001 (FIG. 128). Thereafter, the cartridge may be coupled to jaw member which causes the proximal end 1040*a* of the blocking member 1040 to engage the distal end 1030*b* of the locking lever 1030 which moves the lateral extension 1031 of the locking lever 1030 out of engagement with the notch 1005*b* which allows the working end 1001 to advance through the cartridge (FIG. 129).

When fired, the working end 1001 engages the blocking member 1040 of the actuation sled to move the working end 1001 and blocking members 1040 including the actuation sled distally through the cartridge. The locking lever 1030 will move back to upward configuration as a result of the blocking member 1040 being advanced through the cartridge. When the working end 1001 is moved back to the retracted configuration, the working end 1001 is locked out from advancing as a result of engagement between the lateral extension 1031 and notch 1005*b* of the knife 1005.

With reference to FIGS. 134-137, a reload 1106 includes a locking mechanism according to an embodiment of the instant disclosure and is configured for use with surgical stapling apparatuses 100, 200 is illustrated. The locking mechanisms utilized by reload 1106 and reload 1006 are substantially similar to one another. Accordingly only those features unique to reload 1106 are described in further detail.

Unlike knife 1005 that includes a notch 1005*b*, a notch 1105*b* of suitable configuration is defined within a slot 1105*a* as opposed to a lower interior wall 1105*d* (see FIG. 137 for example). Slot 1105*b* is configured to selectively engage a proximal end 1130a that is provided on a locking lever 1130 to lock out knife 1105 and prevent misfiring thereof (see FIGS. 134-135).

Locking lever 1130 is configured to move sideways as opposed to up and down as with locking lever 1030. Accordingly, locking lever 1130 is biased outwardly to the right to urge proximal end 1130a into engagement with notch 1150b to lock out knife 1105 (FIG. 135).

A blocking member 1140 is provided on an actuation sled 1115 (shown in phantom) and is configured to engage a distal end 1130b of locking lever 1130 (FIG. 134). Specifically, a proximal portion 1115a of blocking member 1140 is angled and configured to selectively engage distal end 1130b to move distal end 1130b inwardly to the left such that proximal end 1130a moves out of engagement of notch 1105b (FIG. 134). Once proximal end 1130a is moved out of engagement with notch 1105b, knife 1105 may be fired.

In use, locking lever 1130 is, initially, biased to a locked out configuration so that knife 1105 cannot be fired (FIG. 135). Cartridge 1112 may be coupled to jaw 1108. In doing so, proximal portion 1140a of blocking member 1140 moves into contact with distal end 1130b of locking lever 1130 and moves proximal end 1130a of locking lever 1130 out of engagement with notch 1105b (FIG. 134).

With proximal end 1130a disengaged from notch 1105b, knife 1105 may then be fired. As knife 1105 travels distally, it contacts actuation sled 1115, which, in turn, moves proximal end 1140a of blocking member 1140 out of engagement with distal end 1130b locking lever 1130 so as to allow distal end 1130b to move back to the biased configuration and locking lever 1130 back to the locked out configuration. In the locked out configuration, proximal end 1130a is allowed to engage notch 1105b when knife 1105 is in the retracted configuration (FIG. 135).

With reference to FIGS. 138-140, a reload 1206 includes a locking mechanism according to an embodiment of the instant disclosure and is configured for use with surgical stapling apparatuses 100, 200 is illustrated.

A locking lever 1230 is pivotably coupled to a bottom surface 1208a adjacent a channel 1214 of jaw member 1208 at a proximal end thereof adjacent the working end 1201. A pivot pin 1231 is utilized to couple locking lever 1230 to bottom surface 1208a and is configured to allow locking lever 1230 to pivot thereabout from an activated (or locked out) configuration (FIG. 138), wherein the working end 1201 is locked out, to a deactivated configuration wherein the working end 1201 is allowed to move distally through cartridge 1212 (FIG. 140). A detent or protuberance 1232 of suitable configuration is provided on a bottom surface of locking lever 1230 and is configured to contact bottom flange 1218b of the working end 1201 as the working end 1201 is translated distally through cartridge 1212. Protuberance 1232 includes a proximal portion 1234a and a distal portion 1234b that are configured to cam locking lever 1230 such that the working end 1201 may move distally past locking lever 1230 and configured to cam locking lever 1230 such that the working end 1201 may be moved proximally past locking lever 1230. A spring (not explicitly shown) may be utilized to bias locking lever 1230 into the activated configuration. Specifically, the spring, e.g., a torsion spring, is configured to bias locking lever 1230 such that a proximal edge 1233 serves as a stop and contacts bottom flange 1218b when the working end 1201 is moved distally.

A bottom portion 1212a of cartridge 1212 adjacent an actuation sled 1215 (shown in phantom) includes a removable tab portion 1240 that is configured to urge locking lever 1230 into the deactivated configuration when cartridge 1212 is installed (FIG. 139). Tab portion 1240 may be affixed to bottom portion 1212a via any suitable methods. For example, in the illustrated embodiment, tab portion 1240 is perforated and configured to be removed when contacted by the working end 1201 as the working end 1201 is translated distally through cartridge 1212 (FIG. 140).

In use, locking lever 1230 is, initially, in the activated configuration to lock out the working end 1201 to prevent misfire thereof (FIG. 138). Thereafter, cartridge 1212 may be installed. In doing so, bottom portion 1212a including tab portion 1240 is positioned over locking lever 1240 to urge locking lever 1240 into the deactivated configuration (FIG. 139).

The working end 1201 may then be fired. As the working end 1201 is translated distally, bottom flange 1218b contacts proximal portion 1234a which causes protuberance 1232 to move upwards, which, in turn, breaks off (e.g., removes) tab portion 1240 (FIG. 140) from the bottom surface 1212a of cartridge 1212. When tab portion 1240 is removed, locking lever 1230 is urged back to the activated configuration and into the cartridge 1212 (see FIG. 138). The working end 1201 may then be moved back to the retracted configuration. Specifically, bottom portion 1218b contacts distal portion 1234b and cams locking lever 1230 such that the working end 1201 may slide over protuberance 1232 and back to the retracted configuration. In the retracted configuration, the working end 1201 is locked out and prevented from misfiring.

With reference to FIGS. 141-149, a reload 1306 includes a locking mechanism according to an embodiment of the instant disclosure and is configured for use with surgical stapling apparatuses 100, 200 is illustrated.

With reference to FIGS. 141-143, initially, reload 1306 includes a pivot assembly 1350 that includes top and lower portions 1350a, 1350b. Unlike the previously described pivot assemblies, e.g., pivot assembly 150, lower portion 1350b of pivot assembly 1350 includes two leg members 1353a, 1353b that are not identical. Specifically, leg member 1353a extends distally past leg member 1353b and includes an aperture 1354 of suitable configuration that is configured to receive therein a lockout structure 1330. In the illustrated embodiment, aperture 1354 includes a generally square configuration that complements a configuration of lockout structure 1330 (FIGS. 143-144). Aperture 1354 is configured so as to allow locking structure 1330 to move outwardly from an activated (locked out) configuration (FIGS. 142 and 146) to a deactivated (or non-locked out) configuration (FIGS. 147 and 149).

With continued reference to FIGS. 141-143, a cam block 1340 operably couples to a channel 1341 (FIG. 142) that is provided within jaw member 1308. Cam block 1340 is translatable along channel 1341 and is configured to contact lockout structure 1330 when cartridge 1312 is installed (FIGS. 146-147). Cam block 1340 includes a proximal portion 1340a and a distal portion 1340b. Distal portion 1340b includes a generally rectangular configuration having a distal wall 1342 that is configured to contact a proximal end of an actuation sled (not shown) of cartridge 1312 when cartridge 1312 is installed. This contact between the actuation sled and distal wall 1342 moves cam block 1340 proximally and into contact with lockout structure 1330. Specifically, an outer facing, slanted, sidewall 1343 is provided at proximal portion 1340a and is configured to cam a corresponding inner facing, slanted, sidewall 1331 provided on lockout structure 1330 (FIGS. 144-145).

In embodiments, cam block 1340 may be configured to selectively couple to the actuation sled via one or more suitable coupling methods. For example, in an embodiment an indent/detent configuration may be utilized to couple cam block 1340 to the actuation sled when the actuation sled is installed. In this particular embodiment, for example, cam block 1340 may include a detent (not shown) that is configured to couple to a corresponding indent on the actuation sled. Moreover, cam block 1340 may be configured to translate distally when the actuation sled is contacted by the working end 1301 and moved distally through cartridge 1312.

Alternatively, while cam block 1340 has bee described herein as being a separate component of the actuation sled, it is within the purview of the instant disclosure to provide cam block 1340 at a proximal end of the actuation sled. In this particular embodiment, cam block 1340 may be monolithically formed with the actuation sled; or may be a separate component that is coupled to the actuation sled via one or more coupling methods, e.g. ultrasonic welding.

Referring to FIGS. 144-145, lockout structure 1330 includes a base portion 1334 and a generally upright post portion 1332. Base portion 1334 is configured so as to allow sidewall 1343 of cam block 1340 to move beneath lockout structure 1330 and into contact with sidewall 1331 lockout structure 1330 as cam block 1340 is moved proximally. Sidewall 1331 extends diagonally across a bottom surface 1334a of base portion 1334 and is configured so as to allow cam block 1340 to cam lockout structure 1330 outwardly (FIGS. 146-147) as cam block 1340 is moved proximally. A top surface 1334b of base portion 1334 slidably contacts a bottom surface 1352 of leg member 1353b and slides therealong when lockout structure 1330 is moved outwardly, see FIGS. 146-147).

Post portion 1332 extends orthogonally from top surface 1334b of base portion 1334 and includes a generally rectangular configuration (FIGS. 144-145). Post portion 1332 is received through aperture 1354 and includes a top portion 1336 that extends past a top surface of leg member 1353a so as to contact a top flange 1318a of a knife 1305 prior to cartridge 1312 being installed (FIGS. 141-142). Specifically, top portion 1336 includes a notched corner 1338 of suitable configuration defined by sidewalls 1338a, 1338b that are disposed at a 90 degree angle with respect to one another and a bottom wall 1338c from which sidewalls 1338a, 1338b extend. Notched corner 1338 is configured to contact top flange 1318a of knife 1305 to lock out the working end 1301 and prevent misfiring thereof.

In embodiments, a leading corner edge 1338c (shown in phantom in FIG. 144) may be provided and configured to allow the working end 1301 to move proximally past lockout structure 1330 so that the working end 1301 may be moved back to the retracted configuration. In this particular embodiment, a top flange 1318a is configured to contact and slide against leading corner edge 1338c so as to allow the working end 1301 to be moved to the retracted configuration.

A spring 1367, e.g., a coil spring, (FIG. 1367) of suitable configuration is provided within aperture 1354 and is configured to bias lockout structure 1330 inwardly. More particularly, spring 1367 is provided within aperture 1354 and contacts an outer sidewall (not explicitly show) of post portion 1332 to urge lockout structure 1330 inwardly. Coil spring 1367 me be coupled to the outer sidewall of post portion 1332 via any suitable coupling methods. For example, an annular recess of suitable configuration may be provided on the outer wall of post portion 1332 and configured to receive coil spring 1367 therein.

In use, lockout structure 1330 is, initially, in the activated configuration to lock out the working end 1301 to prevent misfire thereof (FIG. 142). Thereafter, cartridge 1312 may be installed. As noted above, actuation sled 1315 and cam block 1340 may be configured to couple to one another when cartridge 1312 is installed. In this particular embodiment, actuation sled 1315 contacts cam block 1340 and couples thereto to move cam block 1340 proximally such that sidewall 1343 of cam block 1340 contacts sidewall 1331 of lockout structure 1330 to move top portion 1336 including notched corner 1338 outwardly and out of contact (and/or out of a path of translation of the working end 1301) with top flange 1318a of the working end 1301 (FIGS. 148-149).

The working end 1301 may then be fired. As the working end 1301 translates distally, it contacts the actuation sled and moves the actuation sled including cam block 1340 coupled thereto distally. As a result thereof, cam block 1340 moves out of contact with lockout structure 1330 and lockout structure 1330 moves back to the locked out configuration as a result of the biasing force against the outer wall of post portion 1332 provided by spring 1367.

The working end 1301 may then be moved proximally past lockout structure 1330 and back to the retracted configuration. Once the working end 1301 is moved back to the retracted configuration, lockout structure 1330 locks out the working end 1301 in a manner as described above.

In embodiments where the actuation sled and cam block 1340 are not configured to couple to one another, e.g., such as when the working end 1301 is not configured for multiple firing, cam block 1340 may remain in contact with lockout structure 1330 when the working end 1301 is fired. In this particular embodiment, cam block 1340 maintains lockout structure 1330 in an outward configuration, e.g., a deactivated configuration.

With reference to FIGS. 150-156, and initially with reference to FIGS. 150-151, a reload 1406 includes a locking mechanism according to an embodiment of the instant disclosure and is configured for use with surgical stapling apparatuses 100, 200 is illustrated.

Unlike the previously described embodiments of reloads that utilize locking mechanisms that are configured to prevent firing without a cartridge or spent cartridge installed, reload 1406 (FIG. 150) utilizes a locking mechanism that prevents misfiring of the working end 1401 only when a spent cartridge is coupled to a jaw member 1408. To this end, jaw member 1408 is configured to couple to a cartridge 1412 that includes a latch 1440 and a locking pin 1430 that collectively are configured to prevent misfiring of the working end 1401 when a spent cartridge 1412 is coupled to jaw member 1408.

Latch 1440 is provided at a proximal end of cartridge 1412 and is coupled thereto via one or more suitable coupling methods (FIGS. 151-153). In the illustrated embodiment, for example, latch 1440 includes a generally elongated configuration having an aperture 1441 of suitable configuration that is configured to receive therethrough a rivet 1442, pin or the like. Rivet 1442 extends through a tissue contacting surface 1421 of cartridge 1412 and couples latch 1440 to cartridge 1412 such that a bottom surface (not explicitly shown) of latch 1440 rests against a top surface 1421a that lies in the same general plane as tissue contacting surface 1421 of cartridge 1412. Moreover, rivet 1442 couples latch 1440 to cartridge 1412 so as to allow latch 1440 to rotate about rivet 1442 when latch 1440 is contacted by a top flange 1418a of knife 1405 (FIG. 154).

A boss 1444 extends a predetermined distance orthogonally from a top surface 1446 of latch 1440 and is configured to contact a leading edge 1419*a* of top flange 1418*a* (FIGS. 151 and 154). Boss 1444 includes a generally circumferential configuration which facilitates contact between leading edge 1419*a* and boss 1444 as the working end 1401 is translated distally.

In an initial configuration, latch 1440 positioned at least partially over recess 1431 to contact locking pin 1430 and maintain locking pin 1430 in a deactivated configuration (FIG. 151). Moreover, contact between leading edge 1419*a* and boss 1444 as the working end 1401 translates distally therepast causes latch 1440 to rotate about rivet 1442 and move out of contact with locking pin 1430 so that locking pin 1430 may move into the locked out configuration. (FIGS. 154-156).

Continuing with reference to FIGS. 151-153, locking pin 1430 is provided at a proximal end of cartridge 1412 adjacent latch 1440 and is received within an aperture 1431 that extends through tissue contacting surface 1421 of cartridge 1412. Locking pin 1430 includes a generally circumferential configuration having a flange 1432 at a bottom end thereof configured to contact an interior top wall of cartridge 1412. A tip 1434 of locking pin 1430 includes a distal end 1430*a* that is chamfered, beveled, slanted, etc., to slidably contact a trailing edge 1419*b* of top flange 1418*a* when the working end 1401 is moved back to the retracted configuration; the chamfered configuration of distal end 1430*a* allows for a smooth transition of the working end 1401 past locking pin 1430 (FIG. 155). Moreover, a proximal end 1430*b* does not include a chamfer and is configured to contact leading edge 1419*a* of the working end 1401 to lock out the working end 1401 and prevent misfiring thereof.

Locking pin 1430, e.g., tip 1434, is movable within aperture 1431 from deactivated configuration (FIG. 151), wherein tip 1434 is flush with the tissue contacting surface 1421 of cartridge 1412 (FIG. 151) to an activated (or locked out) configuration, wherein tip 1434 is disposed a predetermined distance above tissue contacting surface 1421 (FIGS. 154 and 156). In the deactivated configuration of locking pin 1434, the working end 1401 including top flange 1418*a* of the knife 1405 is allowed to translate distally past locking pin 1430.

A spring 1467 (or other suitable device) operably couples to locking pin 1430 adjacent flange 1432 and is configured to upwardly bias locking pin 1430 into the activated configuration (FIGS. 152-153). A protrusion of suitable configuration (not shown) may be provided on a bottom surface of locking pin 1430 and configured to couple to spring 1467 to maintain spring 1467 in contact with locking pin 1430. Alternatively, spring 1467 may be fixedly coupled to locking pin 1430 by one or more suitable fixation methods, e.g., an adhesive.

In use, latch 1440 is, initially, positioned over locking pin 1430 to maintain locking in 1430 in the deactivated configuration (FIG. 151). In the deactivated configuration, the working end 1401 is allowed to move distally past locking pin 1430 to the engage actuation sled.

The working end 1401 may then be fired. As the working end 1401 translates distally, leading edge 1419*a* contacts boss 1444, which, in turn rotates latch 1440 about rivet 1442 and moves out of contact with locking pin 1430 so that locking pin 1430 may move into the locked out configuration. (FIGS. 154-156).

The working end 1401 may then be moved back to the retracted configuration. As noted above, the chamfered configuration of distal end 1430*a* allows for a smooth transition of the working end 1401 past locking pin 1430 (FIG. 155).

Once in the retracted configuration, a proximal end 1430*b* contacts leading edge 1419*a* of the working end 1401 to lock out the working end 1401 and prevent misfiring thereof (FIG. 156).

With reference to FIGS. 157-158, a cartridge assembly 1512 is configured for use with a reload (not explicitly shown) that includes a locking mechanism according to an embodiment of the instant disclosure and is configured for use with surgical stapling apparatuses 100, 200 is illustrated.

One or more mechanical interfaces are provided on a proximal end of an actuation sled 1515 and are configured to selectively engage one or more mechanical interfaces disposed on a knife (not explicitly shown). In the illustrated embodiment, for example, a female end 1530 of suitable configuration is provided adjacent a bottom surface 1515*a* of actuation sled 1515 and is configured to selectively engage a corresponding male end (not explicitly shown) that is operably coupled to the knife. Female end 1530 includes a pair of bifurcated posts 1531*a*, 1531*b* that extend in a generally orthogonal direction relative to bottom surface 1515*a* (FIGS. 157-158) and are aligned with the corresponding male end on the knife. Posts 1531*a*, 1531*b* are spaced apart from one another so that a press or friction fit may be utilized to selectively couple the knife and actuation sled 1515 to one another as the knife is translated distally through a firing sequence. As can be appreciated, actuation sled 1515 may include the male end and the knife may include female end 1530. Moreover, it is within the purview of the instant disclosure to utilize other mechanical interfaces to selectively couple actuation sled 1515 and the knife to one another.

A lockout clip 1540 of suitable configuration is provided on bottom surface 1515*a* of actuation sled 1515 and is configured to selectively engage a cover 1561 of cartridge 1512 (FIGS. 157-158) after the knife is fired and moved back to the retracted configuration. Lockout clip 1540 may be monolithically formed with actuation sled 1515 or may be coupled thereto via one or more suitable coupling methods, e.g., adhesive, ultrasonic welding, etc.

In an embodiment, such as the illustrated embodiment, lockout clip 1540 includes a generally elongated portion 1541 that is utilized to couple to bottom surface 1515*a* of actuation sled 1515; this embodiment is particularly useful when lockout clip 1540 is formed as separate component from actuation sled 1515 and, subsequently, coupled thereto. Alternatively, in embodiments, such as when lockout clip 1540 is monolithically formed with actuation sled 1515, elongated portion 1541 may be eliminated.

A generally arcuate portion 1542 extends distally from elongated portion 1541 to form a living hinge thereabout and includes a lip 1543 that engages cover 1561 (FIG. 158). Alternatively, arcuate portion 1542 including lip 1543 may be formed on bottom surface 1515*a* during a manufacturing process of actuation sled 1515. In either instance, arcuate portion 1542 including lip 1543 are configured such that in a pre-installed configuration, lip 1543 is biased towards elongated portion 1541 and bottom surface 1515*a* of actuation sled 1515 so as not to engage cover 1561 (FIG. 157). In accordance with the instant disclosure, locking clip 1540 (and operable components associated therewith) is/are configured not to impede distal translation of the knife through cartridge 1512.

In use, in a pre-installed configuration, actuation sled 1515 is positioned within cartridge 1521 as shown in FIG. 157. In this configuration, locking clip 1540 is not in a locked out configuration and the knife is free to translate distally through a firing sequence.

The knife may then be fired. As the knife translates distally, the male end on the knife engages female end 1530 (FIGS. 154-156) on actuation sled 1515. Thereafter, the knife including actuation sled 1515 now coupled thereto may be moved proximally past a proximal edge 1562 of cartridge 1512 to the retracted configuration. In doing so, lip 1543 is free to flex away from elongated portion 1542 and bottom surface 1515a of actuation sled to a locked out configuration. In the locked out configuration, lip 1543 is positioned to engage proximal edge 1562 of cover 1512, which, in turn, prevents distal translation and, thus, misfiring of the knife (FIG. 158).

The figures show a replaceable loading unit with surgical stapling jaws that has a shaft (such as a shaft 109) that can be attached to a surgical stapling apparatus. Other configurations are contemplated. For example, the replaceable loading unit can itself have a removable and replaceable cartridge assembly. Alternatively, the jaws of the instrument can be permanently attached and configured to receive a removable and replaceable cartridge.

In any of the embodiments disclosed herein, the instrument housing 102 can be manually operated or powered.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical stapling apparatus, comprising:
   a first jaw member;
   a cartridge configured to selectively couple to the first jaw member, the cartridge defining a channel and having fasteners and a platform area, the platform area defining an aperture;
   a second jaw member having an anvil with staple forming depressions;
   a drive member movable from a retracted position to an advanced position, the drive member being configured to drive the fasteners toward the anvil;
   an actuator rotatably disposed in the aperture of the cartridge and having a head portion at a first end, and a notch at a second end, the actuator being biased by a resilient member from a first position to a second position, the head portion having a tip extending into the channel when the actuator is in the first position; and
   an interlock having an extension and being rotatably disposed adjacent the actuator so that the extension is engaged with the notch when the actuator is in the first position, the interlock moving to a position blocking the channel when the actuator moves to the second position.

2. The surgical stapling apparatus according to claim 1, wherein the drive member has a flange that contacts the head portion when the drive member moves from the retracted position to the advanced position.

3. The surgical stapling apparatus according to claim 2, wherein the actuator is biased in a first direction, towards the second end, so that the head portion moves in a second direction, towards the first end, when contacted by the flange.

4. The surgical stapling apparatus according to claim 3, wherein the actuator moves in the second direction to the second position so that the notch is moved away from the extension.

5. The surgical stapling apparatus according to claim 3, wherein a surface of the head portion has a protuberance for engaging the platform area to move the actuator in the second direction.

6. The surgical stapling apparatus according to claim 1, wherein the actuator has beveled side edges to facilitate rotation of the actuator.

7. The surgical stapling apparatus according to claim 1, wherein the head portion has a cone-like shape.

8. The surgical stapling apparatus according to claim 1, wherein the interlock engages a rivet in the position blocking the channel.

9. The surgical stapling apparatus according to claim 1, wherein the interlock is biased toward the position blocking the channel.

10. The surgical stapling apparatus according to claim 1, wherein the drive member includes a trailing surface, the trailing surface engaging the interlock when the drive member is moved from the advanced position to the retracted position.

11. The surgical stapling apparatus according to claim 1, further comprising one or more motors.

12. The surgical stapling apparatus according to claim 1, further comprising a manually operated trigger.

13. The surgical stapling apparatus according to claim 1, wherein the interlock prevents advancement of the drive member from the retracted position when the actuator is in the second position.

14. A surgical stapling apparatus, comprising:
    a first jaw member;
    a second jaw member;
    a cartridge configured to selectively couple to the first jaw member, the cartridge including a plurality of fasteners and defining a channel and an aperture;
    a knife translatable from a retracted position to an advanced position to drive the plurality of fasteners from the cartridge toward the second jaw member;
    an actuator rotatably supported on the cartridge, the actuator having a tip extending into the channel in a first position of the actuator and positioned outside of the channel in a second position of the actuator, the actuator being biased by a resilient member towards the second position; and
    an interlock having a nonblocking position and a blocking position, the interlock preventing translation of the knife from the retracted position towards the advanced position when the interlock is in the blocking position, wherein the interlock rotates to the blocking position in response to the actuator rotating to the second position.

15. The surgical stapling apparatus according to claim 14, wherein the resilient member is configured to engage the actuator to bias the actuator towards the second position.

* * * * *